US007321023B2

(12) United States Patent
Lal et al.

(10) Patent No.: US 7,321,023 B2
(45) Date of Patent: Jan. 22, 2008

(54) SP16 PROTEIN

(75) Inventors: Preeti G. Lal, Santa Clara, CA (US); Janice Au-Young, Brisbane, CA (US); Roopa Reddy, Sunnyvale, CA (US); Lynn E. Murry, Fayetteville, AR (US); Preete Mathur, Bakersfield, CA (US)

(73) Assignee: Incyte Corporation, Palo Alto, CA (US)

( * ) Notice: Subject to any disclaimer, the term of this patent is extended or adjusted under 35 U.S.C. 154(b) by 951 days.

(21) Appl. No.: 09/968,433

(22) Filed: Oct. 1, 2001

(65) Prior Publication Data

US 2003/0073162 A1 Apr. 17, 2003

Related U.S. Application Data

(63) Continuation-in-part of application No. 09/271,110, filed on Mar. 17, 1999, now abandoned, and a continuation-in-part of application No. 08/966,316, filed on Nov. 7, 1997, now Pat. No. 5,932,445.

(51) Int. Cl.
*C07K 14/435* (2006.01)
*C07H 21/00* (2006.01)

(52) U.S. Cl. .................... 530/350; 536/23.5
(58) Field of Classification Search ............ 530/350; 535/23.5
See application file for complete search history.

(56) References Cited

U.S. PATENT DOCUMENTS

| | | | | |
|---|---|---|---|---|
| 5,194,596 | A * | 3/1993 | Tischer et al. | 530/399 |
| 5,350,836 | A * | 9/1994 | Kopchick et al. | 530/399 |
| 5,994,097 | A * | 11/1999 | Lal et al. | 435/69.1 |
| 6,057,126 | A * | 5/2000 | Munroe et al. | 435/69.1 |
| 6,140,060 | A * | 10/2000 | Chun et al. | 435/7.1 |
| 6,620,615 | B1 * | 9/2003 | Gould-Rothberg | 435/325 |
| 6,737,252 | B2 * | 5/2004 | Hedrick et al. | 435/69.1 |
| 6,835,547 | B1 * | 12/2004 | Gosling et al. | 435/7.2 |
| 6,998,239 | B1 * | 2/2006 | Gosling et al. | 435/7.1 |
| 2001/0016336 | A1 * | 8/2001 | Ellis | 435/69.1 |
| 2004/0203080 | A1 * | 10/2004 | Hedrick et al. | 435/7.9 |

OTHER PUBLICATIONS

Haynes et al. Electrophoresis 19 :1862-1871, 1998.*
Clark et al. British Journal of Cancer, 1999.*
Vukicevic et al., 1996, PNAS USA 93:9021-9026.*
Ji et al., The Journal of Biological Chemistry, vol. 273, No. 28, Jul. 1998, pp. 17299-17302.*
Gershengorn and Osman, Endocrinology, Minireview: Insights into G Protein-Coupled Receptor Function Using Molecular Models, vol. 142, No. 1, pp. 2-10.*
Carey et al., Electrophoresis, Review: Trends in DNA forensic analysis. vol. 23, No. 10, pp. 1386-1397, May 2002.*
Anisowicz et al., Molecular Medicine, vol. 2, No. 5, pp. 624-636, Sep. 1996.*
Gygi et al. (Molecular and Cellular Biology, Mar. 1999, p. 1720-1730).*
Gosling et al., Journal of Immunology, Mar. 2000, vol. 164, pp. 2851-2856.*
Schweickardt et al., Journal of Biological chemistry, Mar. 2000, vol. 275, pp. 9550-9556.*
Watson, S. and Arkinstall, S., in The G-Protein Linked Receptor Facts Book, Academic Press, 1994.*
Muller et al., Nature, Mar. 2001, vol. 410, pp. 50-56.*
Zaballos et al., Journal of Immunology, 1999, vol. 162, No. 10, pp. 5671-5675.*
Chen et al., Molecular and Cellular Proteomics, vol. 1, pp. 304-313, Apr. 2002.*
Anderson et al., Electrophoresis, vol. 18, pp. 533-537, 1997.*
Lian et al., (2001, Blood 98:513-524).*
Fessler et al., (2002, J. Biol. Chem. 277:31291-31302).*
Pearson, W.R. and D.J. Lipman, Improved tools for biological sequence comparison, *Proc. Natl. Acad. Sci. USA*, 85:2444-2448 (1988).
Smith, T.F. and M.S. Waterman, Identification of Common Molecular Subsequences, *J. Mol. Biol.*, 147:195-197 (1981).
Krogh, A. et al., Hidden Markov Models in Computational Biology. Applications to Protein Modeling, *J. Mol. Biol.*, 235:1501-1531 (1994).
Stultz, C.M. et al., Structural analysis based on state-space modeling, *Protein Sci.*, 2:305-314 (1993).
Stosberg, A.D., Structure/function relationship of proteins belonging to the family of receptors coupled to GTP-binding proteins, *Eur. J. Biochem.*, 196:1-10 (1991).
Hardie, G. and S. Hanks, *The Protein Kinase FactsBook. Protein-Serine Kinases*, Academic Press, San Diego, CA, vol. I:7-20 (1995).
McGowan, S.E., Extracellular matrix and the regulation of lung development and repair, *FASEB J.*, 6:2895-2904 (1992).
Engel, J. et al., Domain organizations of extracellular matrix proteins and their evolution, *Development*, S35-42 (1994).
Soltysik-Española, M. et al., Endo16, a Large Multidomain Protein Found on the Surface and ECM of Endodermal Cells during Sea Urchin Gastrulation, Binds Calcium, *Dev. Biol.*, 165:73-85 (1994).
Kragh-Hansen, U., Structure and ligand binding properties of human serum albumin, *Dan. Med. Bull.*, 37:57-84 (1990).
Colombatti, A. and P. Bonaldo, The Superfamily of Proteins With von willebrand Factor Type A-like Domains: One Theme Common to Components of Extracellular Matrix, Hemostasis, Cellular Adhesion, and Defense Mechanisms, *Blood*, 77:2305-2315 (1991).

(Continued)

*Primary Examiner*—Eileen B. O'Hara
(74) *Attorney, Agent, or Firm*—Foley & Lardner LLP

(57) ABSTRACT

The invention provides cDNAs which encodes a signal peptide-containing proteins. It also provides for the use of a cDNA, protein, and antibody in the diagnosis, prognosis, treatment and evaluation of therapies for cancer. The invention further provides vectors and host cells for the production of the protein and transgenic model systems.

3 Claims, 6 Drawing Sheets

OTHER PUBLICATIONS

Lee, J.O., et al., Crystal Structure of the A Domain from the α Subunit of Integrin CR3 (CD11b/CD18), *Cell*, 80:631-638 (1995).

Roman, J., Extracellular Matrix and Lung Inflammation, *Immunol. Res.*, 15:163-178 (1996).

Nielsen, M.D. et al., Differential Regulation of Type I and Type VIII $Ca^{2+}$-stimulated Adenylyl Cyclases by $G_i$-coupled Receptors in Vivo, *J. Biol. Chem.*, 271:33308-33316 (1996).

Hellevuo, K. et al, The Characterization of a Novel Human Adenylyl Cyclase Which Is Present in Brain and Other Tissues, *J. Biol. Chem.*, 270:11581-11589 (1995).

Robson, S.C. et al., Loss of ATP Diphosphohydrolase Activity with Endothelial Cell Activation, *J. Exp. Med.*, 185:153-163 (1997).

Matsuoka, I. et al., (Direct Submission) NCBI Accessioin No. S63848, GI 399710, GI 399711 (Sep. 13, 1993).

* cited by examiner

```
                9                 18                 27                 36                 45                 54
5' NGC GAC GTA CAA CAG ATT GGA GCC ATG GCT TTG GAA CAG AAC CAG TCA ACA GAT
                                   M   A   L   E   Q   N   Q   S   T   D
                63                 72                 81                 90                 99                108
   TAT TAT TAT GAG GAA AAT GAA ATG AAT GGC ACT TAT GAC TAC AGT CAA TAT GAA
   Y   Y   Y   E   E   N   E   M   N   G   T   Y   D   Y   S   Q   Y   E
               117                126                135                144                153                162
   CTG ATC TGT ATC AAA GAA GAT GTC AGA GAA TTT GCA AAA GTT TTC CTC CCT GTA
   L   I   C   I   K   E   D   V   R   E   F   A   K   V   F   L   P   V
               171                180                189                198                207                216
   TTC CTC ACA ATA GTT TTC GTC ATT GGA CTT GCA GGC AAT TCC ATG GTA GTG GCA
   F   L   T   I   V   F   V   I   G   L   A   G   N   S   M   V   V   A
               225                234                243                252                261                270
   ATT TAT GCC TAT TAC AAG AAA CAG AGA ACC AAA ACA GAT GTG TAC ATC CTG AAT
   I   Y   A   Y   Y   K   K   Q   R   T   K   T   D   V   Y   I   L   N
               279                288                297                306                315                324
   TTG GCT GTA GCA GAT TTA CTC CTT CTA TTC ACT CTG CCT TTT TGG GCT GTT AAT
   L   A   V   A   D   L   L   L   L   F   T   L   P   F   W   A   V   N
```

FIGURE 1A

```
GCA GTT CAT GGG TGG GTT TTA GGG AAA ATA ATG TGC AAA ATA ACT TCA GCC TTG
 A   V   H   G   W   V   L   G   K   I   M   C   K   I   T   S   A   L  378

TAC ACA CTA AAC TTT GTC TCT GGA ATG CAG TTT CTG GCT TGT AGC ATA GAC
 Y   T   L   N   F   V   S   G   M   Q   F   L   A   C   S   I   D   432

AGA TAT GTG GCA GTA ACT AAA GTC CCC AGC CAA TCA GGA GTG GGA AAA CCA TGC
 R   Y   V   A   V   T   K   V   P   S   Q   S   G   V   G   K   P   C  486

TGG ATC TGT TTC TGT GTC TGG ATG GCT GCC AGG AAT GAC GTA AAT GCT AGG AAT GCT ATA CCC CAG
 W   I   C   F   C   V   W   M   A   A   R   N   D                         540
(approx)
```

FIGURE 1B

```
     657         666         675         684         693         702
TTT GTA CCC TTT ATT ATG GGG GTG TGC TAC TTT ATC ACA GCA AGG ACA
 F   V   P   F   I   M   G   V   C   Y   F   I   T   A   R   T 711         720         729         738         747         756
CTC ATG AAG ATG CCA AAC ATT AAA ATA TCT CGA CCC CTA AAA GTT CTG CTC ACA
 L   M   K   M   P   N   I   K   I   S   R   P   L   K   V   L   L   T 765         774         783         792         801         810
GTC GTT ATA GTT TTC ATT GTC ACT CAA CTG CCT TAT AAC ATT GTC AAG TTC TGC
 V   V   I   V   F   I   V   T   Q   L   P   Y   N   I   V   K   F   C 819         828         837         846         855         864
CGA GCC ATA GAC ATC TAC TCC CTG ATC ACC AGC TGC AAC ATT GTC ATG AGC AAA CGC
 R   A   I   D   I   Y   S   L   I   T   S   C   N   I   V   M   S   K   R 873         882         891         900         909         918
ATG GAC ATC GCC ATC CAA GTC ACA GAA AGC ATC GCA CTC TTT CAC AGC TGC CTC
 M   D   I   A   I   Q   V   T   E   S   I   A   L   F   H   S   C   L 927         936         945         954         963         972
AAC CCA ATC CTT TAT GTT TTT ATG GGA GCA TCT TTC AAA AAC TAC GTT ATG AAA
 N   P   I   L   Y   V   F   M   G   A   S   F   K   N   Y   V   M   K
```

FIGURE 1C

```
      981          990          999         1008         1017        1026
GTG GCC AAG AAA TAT GGG TCC TGG AGA AGA CAG AGA CAA AGT GTG GAG GAG TTT
 V   A   K   K   Y   G   S   W   R   R   Q   R   Q   S   V   E   E   F 1035         1044         1053         1062         1071        1080
CCT TTT GAT TCT GAG GGT CCT ACA GAG CCA ACC AGT ACT TTT AGC ATT TAA AGG
 P   F   D   S   E   G   P   T   E   P   T   S   T   F   S   I 1089         1098         1107         1116         1125        1134
TAA AAC TGC TCT GCC TTT TGC TTG GAT ACA TAT GAA TGA TGC TTT CCC CTC AAA 1143         1152         1161         1170         1179        1188
TAA AAC ATC TGC ATT ATT CTG AAA CTC AAA TCT CAG ACG CCG TGG TTG CAA CTT 1197         1206         1215         1224         1233        1242
ATA ATA AAG AAT GGG TTG GGG GAA GGA GAA ATA AAA GCC AAG AAG AGG AAA 1251         1260         1269         1278         1287        1296
CAA GAT AAT AAA TGT ACA AAA CAT GAA AAT TAA AAT GAA CAA TAT AGG AAA ATA 1305         1314         1323         1332         1341        1350
ATT GTA ACA GGC ATA AGT GAA TAA CAC TCT GCT GTA ACG AAG AAG AGC TTT GTG
```

FIGURE 1D

```
      1359            1368           1377            1386            1395            1404
GTG ATA ATT TTG TAT CTT GGT TGC AGT GGT GCT TAT ACA AAT CTA CAC AAG TGA 1413            1422           1431            1440            1449            1458
TAA AAT GAC AGA GAA CTA TAT ACA CAC ATT GTA CCA ATT TCA ATT TCC TGG TTT 1467            1476           1485            1494            1503            1512
TGA CAT TAT AGT ATA ATT ATG TAA GAT GGA ACC ATT GGG GAA AAC TGG GTG AAG 1521            1530           1539            1548            1557            1566
GGT ACC CAG GAC CAC TCT GTA CCA TCT TTG TAA CTT CCT GTG AAT TTA TAA TAA 1575            1584           1593            1602            1611            1620
TTT CAA AAT AAA ACA AGT TAA AAA AAC CCA CTA TGC TAT AAG TTA GGC CAT 1629            1638           1647            1656
CTA AAA CAG ATT ATT AAA GAG GTT CAT GTT AAA AGG CAT GC 3'
```

SP16 PROTEIN

This application is a continuation-in-part of U.S. Ser. No. 09/271,110, filed 17 Mar. 1999 (now abandoned), and U.S. Pat. No. 5,932,445, issued 3 Aug. 1999, which matured from U.S. Ser. No. 08/966,316, filed 7 Nov. 1997.

FIELD OF THE INVENTION

This invention relates to signal peptide-containing proteins, their encoding cDNAs, and antibodies which binds the proteins, which can be used in the diagnosis, prognosis, treatment and evaluation of therapies for disorders associated with cell proliferation and cell signaling.

BACKGROUND OF THE INVENTION

Protein transport is a quintessential process for both prokaryotic and eukaryotic cells. Transport of an individual protein usually occurs via an amino-terminal signal sequence which directs, or targets, the protein from its ribosomal assembly site to a particular cellular or extracellular location. Transport may involve any combination of several of the following steps: contact with a chaperone, unfolding, interaction with a receptor and/or a pore complex, addition of energy, and refolding. Moreover, an extracellular protein may be produced as an inactive precursor. Once the precursor has been exported, removal of the signal sequence by a signal peptidase activates the protein.

Although amino-terminal signal sequences vary substantially, many patterns and overall properties are shared. Recently, hidden Markov models (HMMs), statistical alternatives to FASTA and Smith Waterman algorithms, have been used to find shared patterns, specifically consensus sequences (Pearson and Lipman (1988) Proc Natl Acad Sci 85:2444-2448; Smith and Waterman (1981) J Mol Biol 147:195-197). Although they were initially developed to examine speech recognition patterns, HMMs have been used in biology to analyze protein and DNA sequences and to model protein structure (Krogh et al (1994) J Mol Biol 235:1501-1531; Collin et al (1993) Protein Sci 2:305-314). HMMs have a formal probabilistic basis and use position-specific scores for amino acids or nucleotides and for opening and extending an insertion or deletion. The algorithms are quite flexible in that they incorporate information from newly identified sequences to build even more successful patterns. To find signal sequences, multiple unaligned sequences are compared to identify those which encode a peptide of 20 to 50 amino acids with an N-terminal methionine.

Some examples of the protein families which are known to have signal sequences are receptors (nuclear, 4 transmembrane, G protein-coupled and tyrosine kinase), cytokines (chemokines), hormones (growth and differentiation factors), neuropeptides and vasomediators, protein kinases, phosphatases, phospholipases, phosphodiesterases, nucleotide cyclases, matrix molecules (adhesion, cadherin, extracellular matrix molecules, integrin, and selectin), G proteins, ion channels (calcium, chloride, potassium, and sodium), proteases, transporter/pumps (amino acid, protein, sugar, metal and vitamin; calcium, phosphate, potassium, and sodium) and regulatory proteins. Receptors, kinases, and matrix proteins and diseases associated with their dysfunction are described below.

G protein-coupled receptors, GPCRs, are a large group of receptors which transduce extracellular signals. GPCRs include receptors for biogenic amines such as dopamine, epinephrine, histamine, glutamate (metabotropic effect), acetylcholine (muscarinic effect), and serotonin; for lipid mediators of inflammation such as prostaglandins, platelet activating factor, and leukotrienes; for peptide hormones such as calcitonin, C5a anaphylatoxin, follicle stimulating hormone, gonadotropin releasing hormone, neurokinin, oxytocin, and thrombin; and for sensory signal mediators such as retinal photopigments and olfactory stimulatory molecules. The structure of these highly-conserved receptors consists of seven hydrophobic transmembrane regions, an extracellular N-terminus and a cytoplasmic C-terminus. The N-terminus interacts with ligands and the C-terminus interacts with intracellular G proteins to activate second messengers such as cyclic AMP (cAMP), phospholipase C, inositol triphosphate, or ion channel proteins. Three extracellular loops alternate with three intracellular loops to link the seven transmembrane regions. The most conserved parts of these proteins are the transmembrane regions and the first two cytoplasmic loops. A conserved, acidic-Arg-aromatic triplet present in the second cytoplasmic loop may interact with the G proteins. The consensus pattern, [GSTALIVMYWC]-[GSTANCPDE]-{EDPKRH}-x(2)-[LIVMNQGA]-x(2)-[LIVMFT]-[GSTANC]-[LIVMFYW-STAC]-[DENH]-R-[FYWCSH]-x(2)-[LIVM] is characteristic of most proteins belonging to this group (Bolander (1994) *Molecular Endocrinology*, Academic Press, San Diego Calif.; Strosberg (1991) Eur J Biochem 196:1-10).

The kinases comprise the largest known group of proteins, a superfamily of enzymes with widely varied functions and specificities. Kinases regulate many different cell proliferation, differentiation, and signaling processes by adding phosphate groups to proteins. Receptor mediated extracellular events trigger the transfer of these high energy phosphate groups and activate intracellular signaling cascades. Activation is roughly analogous to the turning on a molecular switch, and in cases where signaling is uncontrolled, may be associated with or produce inflammation and cancer.

Kinases are usually named after their substrate, their regulatory molecule, or after some aspect of a mutant phenotype. Almost all kinases contain a similar 250-300 amino acid catalytic domain. The N-terminal domain, which contains subdomains I-IV, generally folds into a two-lobed structure which binds and orients the ATP (or GTP) donor molecule. The larger C terminal lobe, which contains subdomains VIA-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (between 5 and 100 residues) located on either side of, or inserted into loops of, the kinase domain. These amino acid sequences allow the regulation of each kinase as it recognizes and interacts with its target protein. The primary structure of the kinase domain is conserved and contains specific residues and identifiable motifs or patterns of amino acids. The serine threonine kinases represent one family which preferentially phosphorylates serine or threonine residues. Many serine threonine kinases, including those from human, rabbit, rat, mouse, and chicken cells and tissues, have been described (Hardie and Hanks (1995) *The Protein Kinase Facts Books*, Vol I:7-20. Academic Press, San Diego Calif.).

The matrix proteins (MPs) provide structural support, cell and tissue identity, and autocrine, paracrine and juxtacrine properties for most eukaryotic cells (McGowan (1992) FASEB J 6:2895-2904). MPs include adhesion molecules, integrins and selectins, cadherins, lectins, lipocalins, and extracellular matrix proteins (ECMs). MPs possess many different domains which interact with soluble, extracellular molecules. These domains include collagen-like domains, EGF-like domains, immunoglobulin-like domains, fibronectin-like domains, type A domain of von Willebrand factor (vWFA)-like modules, ankyrin repeat modules, RDG or RDG-like sequences, carbohydrate-binding domains, and calcium ion-binding domains.

For example, multidomain or mosaic proteins play an important role in the diverse functions of the ECMs (Engel et al (1994) Development S35-42). ECM proteins (ECMPs) are frequently characterized by the presence of one or more domains which may contain a number of potential intracellular disulphide bridge motifs. For example, domains which match the epidermal growth factor tandem repeat consensus are present within several known extracellular proteins that promote cell growth, development, and cell signaling. Other domains share internal homology and a regular distribution of single cysteines and cysteine doublets. In the serum albumin family, cysteine arrangement generates the characteristic 'double-loop' structure (Soltysik-Espanola et al (1994) Dev Biol 165:73-85) important for ligand-binding (Kragh-Hansen (1990) Danish Med Bull 37:57-84). Other ECMPs are members of the vWFA-like module superfamily, a diverse group of proteins with a module sharing high sequence similarity. The vWFA-like module is found not only in plasma proteins, but also in plasma membrane and ECMPs (Colombatti and Bonaldo (1991) Blood 77:2305-2315). Crystal structure analysis of an integrin vWFA-like module shows a classic "Rossmann" fold and suggests a metal ion-dependent adhesion site for binding protein ligands (Lee et al (1995) Cell 80:631-638).

The diversity, distribution and biochemistry of MPs is indicative of their many, overlapping roles in cell proliferation and cell signaling. MPs function in the formation, growth, remodeling, and maintenance of bone, and in the mediation and regulation of inflammation. Biochemical changes that result from congenital, epigenetic, or infectious diseases affect the expression and balance of MPs. This balance, in turn, affects the activation, proliferation, differentiation, and migration of leukocytes and determines whether the immune response is appropriate or self-destructive (Roman (1996) Immunol Res 15:163-178).

Adenylyl cyclases (AC) are a group of second messenger molecules which actively participate in cell signaling processes. There are at least eight types of mammalian ACs which show regions of conserved sequence and are responsive to different stimuli. For example, the neural-specific type I AC is a $Ca^{++}$-stimulated enzyme whereas the human type VII is unresponsive to $CA^{++}$ and responds to prostaglandin E1 and isoproterenol. Characterization of these ACs, their tissue distribution, and the activators and inhibitors of the different types of ACs is the subject of various investigations (Nielsen et al (1996) J Biol Chem 271:33308-16; Hellevuo et al (1995) J Biol Chem 270:11581-9). AC interactions with kinases and G proteins in the intracellular signaling pathways of all tissues make them interesting candidate molecules for pharmaceutical research.

ATP diphosphohydrolase (ATPDase) is an enzyme expressed and secreted by quiescent endothelial cells and involved in vasomediation. The physiological role of ATPDase is to convert ATP and ADP to AMP. When this conversion occurs in the blood vessels during inflammatory response, it prevents extracellular ATP from causing vascular injury by inhibiting platelet activation and modulating vascular thrombosis (Robson et al (1997) J Exp Med 185:153-63).

The discovery of new signal peptide-containing proteins, their encoding cDNAs, and antibodies which bind the proteins satisfies a long standing need in the art by providing molecules and compositions which can be used in the diagnosis, prognosis, treatment and evaluation of therapies for disorders associated with cell proliferation and cell signaling.

SUMMARY OF THE INVENTION

The present invention is based on the discovery of signal peptide-containing proteins, their encoding cDNAs and antibodies which specifically binds the proteins that are useful in the diagnosis, prognosis, treatment and evaluation of therapies for disorders associated with cell proliferation and cell signaling.

The invention provides an isolated cDNA comprising a nucleic acid molecule selected from SEQ ID NOs:1-15 and 17-78. SEQ ID NO:17 encodes a protein having an amino acid sequence of SEQ ID NO:16. The invention also provides isolated cDNAs comprising SEQ ID NOs:18-78 which have from about 80% to about 100% sequence identity with NOs:1-15 and 17. The invention additionally encompasses a complement of the cDNAs selected from SEQ ID NOs:1-15 and 17-78. In one aspect, the cDNA of SEQ ID NO:17 is a fragment or an oligonucleotide comprising a nucleic acid molecule selected from $A_{24}$ to $G_{44}$, $G_{159}$ to $C_{182}$, $G_{561}$ to $A_{596}$, or $A_{1011}$ and $T_{1046}$.

The invention provides compositions comprising the cDNAs or their complements and a heterologous nucleotide sequence or a labeling moiety which may be used in methods of the invention, on a substrate, or in solution. The invention further provides a vector containing the cDNA, a host cell containing the vector, and a method for using the cDNA to make the human protein. The invention still further provides a transgenic cell line or organism comprising the vector containing a cDNA selected from SEQ ID NOs:1-15 and 17-78. In a second aspect, the invention provides a cDNA or the complement thereof which can be used in methods of detection, screening, and purification. In a further aspect, the cDNA is a single-stranded RNA or DNA molecule, a peptide nucleic acid, a branched nucleic acid, and the like.

The invention provides a method for using a cDNA to detect differential expression of a nucleic acid in a sample comprising hybridizing a cDNA to the nucleic acids, thereby forming hybridization complexes and comparing hybridization complex formation with at least one standard, wherein the comparison indicates differential expression of the cDNA in the sample. In one aspect, the method of detection further comprises amplifying the nucleic acids of the sample prior to hybridization. In another aspect, the method showing differential expression of the cDNA is used to diagnose a cancer.

The invention additionally provides a method for using a composition of the invention to screen a plurality of molecules or compounds to identify or purify at least one ligand which specifically binds the cDNA, the method comprising combining the composition with the molecules or compounds under conditions allowing specific binding, and detecting specific binding to the composition, thereby identifying or purifying a ligand which binds the composition. In one aspect, the molecules or compounds are selected from aptamers, DNA molecules, RNA molecules, peptide nucleic acids, artificial chromosome constructions, peptides, transcription factors, repressors, and regulatory molecules.

The invention provides a purified protein or a portion thereof selected from the group consisting of an amino acid sequence of SEQ ID NO:16, a variant of SEQ ID NO:16, an antigenic epitope of SEQ ID NO:16, and a biologically active portion of SEQ ID NO:16. The invention also provides a composition comprising the purified protein and a labeling moiety or a pharmaceutical carrier. The invention further provides a method of using the protein to treat a subject with cancer comprising administering to a patient in need of such treatment a composition containing the purified protein and a pharmaceutical carrier. The invention still further provides a method for using a protein to screen a library or a plurality of molecules or compounds to identify or purify at least one ligand, the method comprising combining the protein with the molecules or compounds under conditions to allow specific binding and detecting specific binding, thereby identifying or purifying a ligand which specifically binds the protein. In one aspect, the molecules or compounds are selected from DNA molecules, RNA molecules, peptide nucleic acids, peptides, proteins, mimetics, agonists, antagonists, antibodies, immunoglobulins, inhibitors, and drugs. In another aspect, the ligand is used to treat a subject with a cancer.

The invention provides a method of using a protein having the amino acid sequence of SEQ ID NO:16 to screen a plurality of antibodies to identify an antibody which specifically binds the protein comprising contacting isolated antibodies with the protein under conditions to form an antibody:protein complex, and dissociating the antibody from the protein, thereby obtaining antibody which specifically binds the protein.

The invention also provides methods for using a protein having the amino acid sequence of SEQ ID NO:16 to prepare and purify polyclonal and monoclonal antibodies which specifically bind the protein. The method for preparing a polyclonal antibody comprises immunizing a animal with protein under conditions to elicit an antibody response, isolating animal antibodies, attaching the protein to a substrate, contacting the substrate with isolated antibodies under conditions to allow specific binding to the protein, dissociating the antibodies from the protein, thereby obtaining purified polyclonal antibodies. The method for preparing and purifying monoclonal antibodies comprises immunizing a animal with a protein under conditions to elicit an antibody response, isolating antibody producing cells from the animal, fusing the antibody producing cells with immortalized cells in culture to form monoclonal antibody producing hybridoma cells, culturing the hybridoma cells, and isolating from culture monoclonal antibodies which specifically bind the protein.

The invention provides purified polyclonal and monoclonal antibodies which bind specifically to a protein. The invention also provides a method for using an antibody to detect expression of a protein in a sample, the method comprising combining the antibody with a sample under conditions which allow the formation of antibody:protein complexes; and detecting complex formation, wherein complex formation indicates expression of the protein in the sample. In one aspect, the amount of complex formation when compared to standards is diagnostic of cancer.

The invention provides a method for inserting a heterologous marker gene into the genomic DNA of a mammal to disrupt the expression of the endogenous polynucleotide. The invention also provides a method for using a cDNA to produce a model system, the method comprising constructing a vector containing a DNA selected from SEQ ID NOs:1-15 and 17-78 transforming the vector into an embryonic stem cell, selecting a transformed embryonic stem cell, microinjecting the transformed embryonic stem cell into a blastocyst, thereby forming a chimeric blastocyst, transferring the chimeric blastocyst into a pseudopregnant dam, wherein the dam gives birth to a chimeric offspring containing the cDNA in its germ line, and breeding the chimeric mammal to produce a homozygous, model system.

BRIEF DESCRIPTION OF THE FIGURES AND TABLE

FIGS. 1A-1E show the amino acid sequence of SP16 (SEQ ID NO:16) and a nucleic acid sequence of its encoding cDNA (SEQ ID NO:17). The alignment was produced using MACDNASIS PRO software (Hitachi Software Engineering, South San Francisco Calif.).

FIG. 2 shows the amino acid sequence alignment between SP-16 (2547002; SEQ ID NO:16) and bovine GPCR (GI 399711; SEQ ID NO:79) produced using the MEGALIGN program of LASERGENE software (DNASTAR, Madison Wis.).

Table 1 shows the sequence identification numbers, reference, Incyte Clone number, cDNA library, NCBI sequence identifier and GenBank description for each of the signal peptide-containing proteins encoded by the cDNAs.

DESCRIPTION OF THE INVENTION

It is understood that this invention is not limited to the particular machines, materials and methods described. It is also to be understood that the terminology used herein is for the purpose of describing particular embodiments and is not intended to limit the scope of the present invention which will be limited only by the appended claims. As used herein, the singular forms "a", "an", and "the" include plural reference unless the context clearly dictates otherwise. For example, a reference to "a host cell" includes a plurality of such host cells known to those skilled in the art.

Unless defined otherwise, all technical and scientific terns used herein have the same meanings as commonly understood by one of ordinary skill in the art to which this invention belongs. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"Array" refers to an ordered arrangement of at least two cDNAs or antibodies on a substrate. At least one of the cDNAs or antibodies represents a control or standard, and the other, a cDNA or antibody of diagnostic or therapeutic interest. The arrangement of two to about 40,000 cDNAs or of two to about 40,000 monoclonal or polyclonal antibodies on the substrate assures that the size and signal intensity of each labeled hybridization complex, formed between each cDNA and at least one nucleic acid, or antibody:protein complex, formed between each antibody and at least one protein to which the antibody specifically binds, is individually distinguishable.

The "complement" of a cDNA of the Sequence Listing refers to a nucleic acid molecule which is completely complementary to the cDNA over its full length and which will hybridize to the cDNA or an mRNA under conditions of maximal stringency.

"cDNA" refers to an isolated polynucleotide, nucleic acid molecule, or any fragment or complement thereof. It may have originated recombinantly or synthetically, may be double-stranded or single-stranded, represents coding and noncoding 3' or 5' sequence, and generally lacks introns.

A "composition" refers to the polynucleotide and a labeling moiety, a purified protein and a pharmaceutical carrier or a labeling moiety, an antibody and a labeling moiety, and the like.

"Derivative" refers to a cDNA or a protein that has been subjected to a chemical modification. Derivatization of a cDNA can involve substitution of a nontraditional base such as queosine or of an analog such as hypoxanthine. Derivatization of a protein involves the replacement of a hydrogen by an acetyl, acyl, alkyl, amino, formyl, or morpholino group. Derivative molecules retain the biological activities of the naturally occurring molecules but may confer advantages such as longer lifespan or enhanced activity.

"Differential expression" refers to an increased or up-regulated or a decreased or down-regulated expression as detected by presence, absence or at least two-fold change in the amount or abundance of a transcribed messenger RNA or translated protein in a sample.

Disorders associated with cell proliferation and cell signaling include cancers, genetic, and immune conditions. Each disorder is associated with expression of a signal peptide-containing protein or its specific encoding cDNA. These disorders include, but are not limited to, adenofibromatous hyperplasia as a prognostic of prostate cancer, asthma, arthritis, breast cancers such as ductal, lobular, and adeno-carcinomas, Huntington's disease, mucinous cystadenoma of the ovary, renal cell cancer, schizophrenia stomach tumor, testicular seminoma, transitional cell carcinoma of the bladder, and uterine adenosquamous carcinoma.

"Fragment" refers to a chain of consecutive nucleotides from about 50 to about 4000 base pairs in length. Fragments may be used in PCR or hybridization technologies to identify related nucleic acid molecules and in binding assays to screen for a ligand. Such ligands are useful as therapeutics to regulate replication, transcription or translation.

A "hybridization complex" is formed between a cDNA and a nucleic acid of a sample when the purines of one molecule hydrogen bond with the pyrimidines of the complementary molecule, e.g., 5'-A-G-T-C-3' base pairs with 3'-T-C-A-G-5'. Hybridization conditions, degree of complementarity and the use of nucleotide analogs affect the efficiency and stringency of hybridization reactions.

"Labeling moiety" refers to any visible or radioactive label than can be attached to or incorporated into a cDNA or protein. Visible labels include but are not limited to anthocyanins, green fluorescent protein (GFP), β glucuronidase, luciferase, Cy3 and Cy5, and the like. Radioactive markers include radioactive forms of hydrogen, iodine, phosphorous, sulfur, and the like.

"Ligand" refers to any agent, molecule, or compound which will bind specifically to a polynucleotide or to an epitope of a protein. Such ligands stabilize or modulate the activity of polynucleotides or proteins and may be composed of inorganic and/or organic substances including minerals, cofactors, nucleic acids, proteins, carbohydrates, fats, and lipids.

"Oligonucleotide" refers a single-stranded molecule from about 18 to about 60 nucleotides in length which may be used in hybridization or amplification technologies or in regulation of replication, transcription or translation. Equivalent terms are amplimer, primer, and oligomer.

An "oligopeptide" is an amino acid sequence from about five residues to about 15 residues that is used as part of a fusion protein to produce an antibody.

"Portion" refers to any part of a protein used for any purpose; but especially, to an epitope for the screening of ligands or for the production of antibodies.

"Post-translational modification" of a protein can involve lipidation, glycosylation, phosphorylation, acetylation, racemization, proteolytic cleavage, and the like. These processes may occur synthetically or biochemically. Biochemical modifications will vary by cellular location, cell type, pH, enzymatic milieu, and the like.

"Probe" refers to a cDNA that hybridizes to at least one nucleic acid in a sample. Where targets are single-stranded, probes are complementary single strands. Probes can be labeled with reporter molecules for use in hybridization reactions including Southern, northern, in situ, dot blot, array, and like technologies or in screening assays.

"Protein" refers to a polypeptide or any portion thereof. A "portion" of a protein refers to that length of amino acid sequence which would retain at least one biological activity, a domain identified by PFAM or PRINTS analysis or an antigenic epitope of the protein identified using Kyte-Doolittle algorithms of the PROTEAN program (DNASTAR).

"Purified" refers to any molecule or compound that is separated from its natural environment and is from about 60% free to about 90% free from other components with which it is naturally associated.

"Sample" is used in its broadest sense as containing nucleic acids, proteins, antibodies, and the like. A sample may comprise a bodily fluid; the soluble fraction of a cell preparation, or an aliquot of media in which cells were grown; a chromosome, an organelle, or membrane isolated or extracted from a cell; genomic DNA, RNA, or cDNA in solution or bound to a substrate; a biopsy, a cell; a tissue; a tissue print; a fingerprint, buccal cells, skin, or hair; and the like.

"Similarity" refers to the quantification (usually percentage) of nucleotide or residue matches between at least two sequences aligned using a standard algorithm such as Smith-Waterman alignment (Smith and Waterman (1981) J Mol Biol 147:195-197) or BLAST2 (Altschul et al (1997) Nucleic Acids Res 25:3389-3402). BLAST2 may be used in a reproducible way to insert gaps in one of the sequences in order to optimize alignment and to achieve a more meaningful comparison between them. Particularly in proteins, similarity is greater than identity in that conservative substitutions (for example, valine for leucine or isoleucine) are counted in calculating the reported percentage. Substitutions which are considered to be conservative are well known in the art.

"Specific binding" refers to a special and precise interaction between two molecules which is dependent upon their structure, particularly their molecular side groups. For example, the intercalation of a regulatory protein into the major groove of a DNA molecule or the binding between an epitope of a protein and an agonist, antagonist, or antibody.

"Substrate" refers to any rigid or semi-rigid support to which cDNAs or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

A "transcript image" is a profile of gene transcription activity in a particular tissue at a particular time.

"Variant" refers to molecules that are recognized variations of a cDNA or a protein encoded by the cDNA. Splice variants may be determined by BLAST score, wherein the score is at least 100, and most preferably at least 400. Allelic variants have a high percent identity to the cDNAs and may differ by about three bases per hundred bases. "Single nucleotide polymorphism" (SNP) refers to a change in a single base as a result of a substitution, insertion or deletion. The change may be conservative (purine for purine) or non-conservative (purine to pyrimidine) and may or may not result in a change in an encoded amino acid or its secondary, tertiary, or quaternary structure.

The Invention

The invention is based on the discovery of signal peptide-containing proteins, individually SP-1 through SP-16, and their encoding or regulating cDNAs, SEQ ID NOs:1-15 and 17 which are characterized in TABLE 1. U.S. Ser. No. 09/271,110, filed 17 Mar. 1999, is incorporated by reference herein in its entirety. The cDNAs and fragments thereof, the proteins and portions thereof, and an antibody which specifically binds each protein can be used directly or as compositions for the diagnosis, prognosis, treatment and evaluation of therapies for disorders associated with cell proliferation and cell signaling.

SP-1 was identified in Incyte Clone 1221102 from the NEUTGMT01 cDNA library using a computer search for amino acid sequence alignments. A cDNA comprising the nucleic acid shown in SEQ ID NO:1 and derived using Incyte Clone 1221102, which encompasses nucleotides 300-514 also found in Incyte clone 5269342F6 (SEQ ID NO:18) which was used on HumanGenomeGEM1 microarray, encodes a GPCR with homology to g1575512, the GPR19 gene. Electronic northern analysis showed the expression of this sequence in neuronal tissues and in stimulated granulocytes. The transcript image found in EXAMPLE VIII supported the northern analysis and showed four-fold, up-regulated expression of the cDNA encoding SP-1 in the brain from a subject diagnosed with Huntington's disease.

SP-2 was identified in Incyte Clone 1457779 from the COLNFET02 cDNA library using a computer search for amino acid sequence alignments. A cDNA comprising the nucleic acid shown in SEQ ID NO:2 and derived from Incyte Clone 1457779, which encompasses nucleotides 1-466 also found in Incyte clone 1457779F6 (SEQ ID NO:22) which was used on LifeGEM1 microarray, encodes an ATP diphosphohydrolase with homology to g1842120. Electronic northern analysis showed the expression of this sequence in fetal colon, and transcript imaging showed that differential expression of SP-2 is diagnostic of stomach tumor.

SP-3 was identified in Incyte Clone 1682433 from the PROSNOT15 cDNA library using a computer search for amino acid sequence alignments. A cDNA comprising the nucleic acid shown in SEQ ID NO:3 and derived from Incyte Clone 1682433, which encompasses nucleotides 1-481 also found in Incyte clone 2444714F6 (SEQ ID NO:26) which was used on LifeGEM1 microarray, encodes a signal peptide-containing protein with homology to g1070391, a transmembrane protein. Electronic northern analysis showed the expression of this sequence in fetal, cancerous or inflamed cells and tissues. Transcript imaging showed that differential expression of SP-3 is diagnostic of ductal carcinoma of the breast.

SP-4 was identified in Incyte Clone 1899132 from the BLADTUT06 cDNA library using a computer search for amino acid sequence alignments. A nucleotide sequence, SEQ ID NO:4, derived from Incyte Clone 1899132, which encompasses nucleotides 272-625 also found in Incyte clone 1899132F6 (SEQ ID NO:31) which was used on LifeGEM1 microarray encodes a signal peptide containing protein with homology to g887602, a *Saccharomyces cerevisiae* protein. Electronic northern analysis showed the expression of this sequence in cancerous and inflamed cells and tissues; transcript imaging showed that differential expression of SP-4 is diagnostic of uterine adenosquamous carcinoma.

SP-5 was identified in Incyte Clone 1907344 from the CONNTUT01 cDNA library using a computer search for amino acid sequence alignments. A nucleotide sequence, SEQ ID NO:5, derived from Incyte Clone 1907344, which encompasses nucleotides 17-450 also found in Incyte clone 2487075F6 (SEQ ID NO:35) which was used on HumanGenomeGEM1 microarray, encodes a signal peptide containing protein with homology to g33715, immunoglobulin light chain. Electronic northern analysis showed the expression of this sequence in cancerous and fetal or infant cells and tissues; transcript imaging showed that differential expression of SP-5 is diagnostic for adenocarcinoma of the breast.

SP-6 was identified in Incyte Clone 1963651 from the BRSTNOT04 cDNA library using a computer search for amino acid sequence alignments. A nucleotide sequence, SEQ ID NO:6, derived from Incyte Clone 1963651, which encompasses nucleotides 651-1090 also found in Incyte clone 1414964F6 (SEQ ID NO:41) which was used on LifeGEM1 microarray, encodes a GPCR with homology to g1657623, orphan receptor RDC1. Although electronic northern analysis showed expression in ductal carcinoma; transcript imaging showed that differential expression of SP6 in ovary is diagnostic for mucinous cystadenoma.

SP-7 was identified in Incyte Clone 1976095 from the PANCTUT02 cDNA library using a computer search for amino acid sequence alignments. A nucleotide sequence, SEQ ID NO:7, derived from Incyte Clone 1976095, which encompasses nucleotides 74-525 also found in Incyte clone 1976095F6 (SEQ ID NO:44) which was used on LifeGEM1 microarray, encodes a signal peptide-containing protein with homology to g2117185, a *Mycobacterium tuberculosis* protein. Electronic northern analysis showed the expression of this sequence in cancerous and inflamed tissues; transcript imaging showed that differential expression of SP-7 in synovium or cartilage is diagnostic for arthritis.

SP-8 was identified in Incyte Clone 2417676 from the HNT3AZT01 cDNA library using a computer search for amino acid sequence alignments. A nucleotide sequence, SEQ ID NO:8, derived from Incyte Clone 2417676, which encompasses nucleotides 2-363 also found in Incyte clone 2890678F6 (SEQ ID NO:49) which was used on HumanGenomeGEM1 microarray, encodes a signal peptide-containing protein with homology to g2150012, a human transmembrane protein. Electronic northern analysis showed this sequence to be expressed in proliferating, cancerous or inflamed tissues; transcript imaging shows that differential expression of SP-8 is diagnostic for testicular seminoma.

SP-9 was identified in Incyte Clone 1805538 from the SINTNOT13 cDNA library using a computer search for amino acid sequence alignments. A nucleotide sequence, SEQ ID NO:9, derived from Incyte Clone 1805538, which encompasses nucleotides 15-419 also found in Incyte clone 2183094F6 (SEQ ID NO:53) which was used on LifeGEM1 microarray, encodes a signal peptide-containing protein with homology to g294502, an extracellular matrix protein. Electronic northern analysis showed this sequence to be expressed in inflamed tissues; transcript imaging showed that differential expression of SP-9 is diagnostic of adenofibromatous hyperplasia and prognostic for prostate cancer.

SP-10 was identified in Incyte Clone 1869688 from the SKINBIT01 cDNA library using a computer search for amino acid sequence alignments. A nucleotide sequence, SEQ ID NO:10, derived from Incyte Clone 1869688, which encompasses nucleotides 1124-1380 also found in Incyte clone 2182042F6 (SEQ ID NO:57) which was used on HumanGenomeGEM1 microarray, encodes a signal peptide-containing protein with homology to g1562, a G3 serine/threonine kinase. Electronic northern analysis showed this sequence to be expressed in proliferating tissues; transcript imaging showed that differential expression of SP-10 is diagnostic of transitional cell carcinoma of the bladder.

SP-11 was identified in Incyte Clone 1880692 from the LEUKNOT03 cDNA library using a computer search for amino acid sequence alignments. A nucleotide sequence, SEQ ID NO:11, derived from Incyte Clone 1880692, which encompasses nucleotides 12-309 also found in Incyte clone 1880692F6 (SEQ ID NO:60) which was used on LifeGEM1 microarray, encodes a signal peptide-containing protein with homology to g1487910, a *C. elegans* protein. Electronic northern analysis showed this sequence to be expressed in cancer and blood cells; transcript imaging showed that differential expression of SP-11 is diagnostic for renal cell cancer.

SP-12 was identified in Incyte Clone 318060 from the EOSIHET02 cDNA library using a computer search for amino acid sequence alignments. A nucleotide sequence, SEQ ID NO:12, derived from Incyte Clone 318060, which encompasses nucleotides 193-1244 also found in Incyte clone 1266985F6 (SEQ ID NO:64) which was used on HumanGenomeGEM1 microarray, encodes a receptor with homology to g606788, an opioid GPCR. Although electronic northern analysis showed this sequence to be expressed in nerve and blood cells; transcript imaging showed that differential expression of SP-12 is diagnostic for adenocarcinoma of the breast.

SP-13 was identified in Incyte Clone 396450 from the PITUNOT02 cDNA library using a computer search for amino acid sequence alignments. A nucleotide sequence, SEQ ID NO:13, derived from Incyte Clone 396450, which encompasses nucleotides 1-277 also found in Incyte clone 396450R6 (SEQ ID NO:65) which was used on LifeGEM1 microarray, encodes a signal peptide-containing protein with homology to g342279, opiomelanocortin. Electronic northern analysis showed this sequence to be expressed in hormone producing cells and tissues and inflamed cells and tissues; transcript imaging showed that differential expression of SP-13 is diagnostic for schizophrenia.

SP-14 was identified in Incyte Clone 506333 from the TMLR3DT02 cDNA library using a computer search for amino acid sequence alignments. A nucleotide sequence, SEQ ID NO:14, derived from Incyte Clone 506333, which encompasses nucleotides 1-514 also found in Incyte clone 506333T6 (SEQ ID NO:68) which was used on LifeGEM1 microarray, encodes a signal peptide-containing protein with homology to g2204110, adenylyl cyclase. Electronic northern analysis showed this sequence to be expressed in cancerous and inflamed cells and tissues; transcript imaging showed that differential expression of SP-14 is diagnostic of breast cancer, in particular lobular carcinoma of the breast.

SP-15 was identified in Incyte Clone 764465 from the LUNGNOT04 cDNA library using a computer search for amino acid sequence alignments. A nucleotide sequence, SEQ ID NO:15, derived from Incyte Clone 764465, which encompasses nucleotides 49-528 also found in Incyte clone 764465R6 (SEQ ID NO:69) which was used on LifeGEM1 microarray, encodes a receptor with homology to GI 1902984, lectin-like oxidized LDL receptor. Electronic northern analysis showed this sequence to be expressed in lung and in fetal liver; transcript imaging confirms the northern analysis and shows that differential expression of SP-15 when used with lung samples is diagnostic for asthma.

SP-16 (SEQ ID NO:16) was identified in Incyte Clone 2547002 from the UTRSNOT11 cDNA library using a computer search for amino acid sequence alignments. A consensus sequence, SEQ ID NO:17, was derived from the extension and assembly of the overlapping nucleic acid sequences of Incyte Clones 2741185T6, 2741185T6F6.comp, and 2741185H1 (BRSTTUT14) and 2547002F6 and 2547002H1(UTRSNOT11), SEQ ID NOs: 72-76, respectively.

In one embodiment, the invention encompasses a polypeptide comprising the amino acid sequence of SEQ ID NO:16, as shown in FIGS. 1A-1E. SP-16 is 350 amino acids in length and has a G protein coupled receptor signature at $S_{125}$GMQFLACISIDRYVAV; three potential N-glycosylation sites at $N_6$, $N_{19}$, and $N_{276}$; a potential glycosaminoglycan attachment site at $S_{148}$; and ten potential phosphorylation sites at $S_{25}$, $T_{74}$, $T_{177}$, $S_{195}$, $T_{223}$, $Y_{269}$, $S_{278}$, $S_{309}$, $S_{323}$, and $S_{330}$. SP-16 has 86% sequence identity with a bovine GPCR (g399711) and shares the GPCR signature, the N-glycosylation, the glycosaminoglycan attachment site, and the first nine of the phosphorylation sites with the bovine receptor (FIG. 2). Fragments of the nucleic acid molecule useful for designing oligonucleotides or to be used directly as hybridization probes to distinguish between these homologous molecules include $A_{24}$ to $G_{44}$, $G_{159}$ to $C_{182}$, $G_{561}$ to $A_{596}$, or $A_{1011}$ to $T_{1046}$. mRNA encoding SP-16 was sparsely expressed in cDNA libraries. Electronic northern analysis (EXAMPLE VIII below) showed expression in breast adenocarcinoma; transcript imaging confirmed the northen analysis and showed that SP-16 is differentially expressed in breast adenocarcinoma and not in matched or normal breast tissues.

cDNA fragments encoding or regulating signal peptide-containing proteins were identified using BLAST2 with default parameters and the ZOOSEQ databases (Incyte Genomics, Palo Alto Calif.). These cDNAs have from about 80% to about 95% sequence identity to the human cDNA as shown in the table below. The first column shows the SEQ $ID_H$ for the human cDNA; the second column, the SEQ $ID_{FR}$ for fragment cDNAs; the third column, the sequence numbers for the fragments; the fourth column, the species; the fifth column, percent identity to the human cDNA; and the sixth column, the nucleotide alignment ($Nt_H$) of the human and fragment cDNAs.

| SEQ $ID_H$ | SEQ $ID_{FR}$ | Clone No. | Species | Identity | $Nt_H$ Alignment |
|---|---|---|---|---|---|
| 1 | 19 | 051293_Mm.1 | Mouse | 80% | 1-518 |
| 1 | 20 | 703901370J1 | Rat | 84% | 1-518 |
| 1 | 21 | 296771_Rn.1 | Rat | 81% | 1-518 |
| 2 | 23 | 023793_Mm.1 | Mouse | 83% | 307-606 |
| 2 | 24 | 701923941H1 | Rat | 84% | 402-606 |
| 2 | 25 | 317489_Rn.1 | Rat | 84% | 402-606 |
| 3 | 27 | 703711491J1 | Dog | 89% | 817-1075 |
| 3 | 28 | 060931_Mm.3 | Mouse | 85% | 95-1099 |
| 3 | 29 | 701926832H1 | Rat | 88% | 801-1033 |
| 3 | 30 | 317017_Rn.1 | Rat | 88% | 801-1033 |
| 4 | 32 | 026438_Mm.1 | Mouse | 84% | 311-861 |

-continued

| SEQ ID$_H$ | SEQ ID$_{FR}$ | Clone No. | Species | Identity | Nt$_H$ Alignment |
|---|---|---|---|---|---|
| 4 | 33 | 70298994H1 | Rat | 86% | 489-731 |
| 4 | 34 | 286037_Rn.1 | Rat | 86% | 341-731 |
| 5 | 36 | 703200737J1 | Monkey | 90% | 280-450 |
| 5 | 37 | 071816_Mf.2 | Monkey | 86% | 280-450 |
| 5 | 38 | 008837_Cf.1 | Dog | 89% | 38-361 |
| 5 | 39 | 700298833H1 | Rat | 92% | 263-450 |
| 5 | 40 | 274060_Rn.1 | Rat | 92% | 263-450 |
| 6 | 42 | 031166_Mm.1 | Mouse | 87% | 201-1803 |
| 6 | 43 | 203462_Rn.3 | Rat | 87% | 776-1261 |
| 7 | 45 | 005653_Mf.1 | Monkey | 90% | 519-700 |
| 7 | 46 | 007876_Cf.1 | Dog | 89% | 134-700 |
| 7 | 47 | 003508_Mm.1 | Mouse | 83% | 98-668 |
| 7 | 48 | 205363_Rn.4 | Rat | 84% | 74-700 |
| 8 | 50 | 008780_Cf.1 | Dog | 93% | 186-296 |
| 8 | 51 | 013606_Mm.1 | Mouse | 86% | 37-357 |
| 8 | 52 | 248462_Rn.1 | Rat | 89% | 110-313 |
| 9 | 54 | 001680_Cf.1 | Dog | 85% | 148-201 |
| 9 | 55 | 021581_Mm.1 | Mouse | 82% | 232-532 |
| 9 | 56 | 283960_Rn.1 | Rat | 86% | 232-307 |
| 10 | 58 | 037196_Mm.1 | Mouse | 90% | 192-1040 |
| 10 | 59 | 215631_Rn.1 | Rat | 88% | 170-651 |
| 11 | 61 | 023463_Cf.1 | Dog | 90% | 93-363 |
| 11 | 62 | 017863_Mm.1 | Mouse | 85% | 179-619 |
| 11 | 63 | 300968_Rn.1 | Rat | 82% | 179-647 |
| 13 | 66 | 019409_Mm.2 | Mouse | 83% | 136-272 |
| 13 | 67 | 216194_Rn.7 | Rat | 84% | 134-272 |
| 15 | 70 | 028681_Mm.2 | Mouse | 80% | 54-215 |
| 15 | 71 | 211274_Rn.1 | Rat | 88% | 56-114 |
| 17 | 77 | 000569_Mm.1 | Mouse | 87% | 789-1091 |
| 17 | 78 | 251020_Rn.1 | Rat | 83% | 180-820 |

It will be appreciated by those skilled in the art that as a result of the degeneracy of the genetic code, a multitude of cDNAs encoding signal peptide-containing proteins, some bearing minimal similarity to the cDNAs of any known and naturally occurring gene, may be produced. Thus, the invention contemplates each and every possible variation of cDNA that could be made by selecting combinations based on possible codon choices. These combinations are made in accordance with the standard triplet genetic code as applied to the polynucleotide encoding naturally occurring signal peptide-containing proteins, and all such variations are to be considered as being specifically disclosed.

The cDNAs of SEQ ID NOs:1-15 and 17-78 may be used in hybridization, amplification, and screening technologies to identify and distinguish among the identical and related molecules in a sample. The cDNAs may also be used to produce transgenic cell lines or organisms which are model systems for cancers and upon which the toxicity and efficacy of potential therapeutic treatments may be tested. Toxicology studies, clinical trials, and subject/patient treatment profiles may be performed and monitored using the cDNAs, proteins, antibodies and molecules and compounds identified using the cDNAs and proteins of the present invention.

Characterization and Use of the Invention cDNA Libraries

In a particular embodiment disclosed herein, mRNA is isolated from cells and tissues using methods which are well known to those skilled in the art and used to prepare the cDNA libraries. The Incyte cDNAs were isolated from cDNA libraries prepared as described in the EXAMPLES. The consensus sequences are chemically and/or electronically assembled from fragments including Incyte cDNAs and extension and/or shotgun sequences using computer programs such as PHRAP (P Green, University of Washington, Seattle Wash.), and the AUTOASSEMBLER application (ABI). After verification of the 5' and 3' sequence, at least one of the representative cDNAs which encode a signal peptide-containing protein is designated a reagent. These reagent cDNAs are also used in the construction of human microarrays and are represented among the sequences on the Human Genome Gem Arrays (Incyte Genomics).

Sequencing

Methods for sequencing nucleic acids are well known in the art and may be used to practice any of the embodiments of the invention. These methods employ enzymes such as the Klenow fragment of DNA polymerase I, SEQUENASE, Taq DNA polymerase and thermostable T7 DNA polymerase (Amersham Pharmacia Biotech (APB), Piscataway N.J.), or combinations of polymerases and proofreading exonucleases such as those found in the ELONGASE amplification system (Life Technologies, Gaithersburg Md.). Preferably, sequence preparation is automated with machines such as the MICROLAB 2200 system (Hamilton, Reno Nev.) and the DNA ENGINE thermal cycler (MJ Research, Watertown Mass.). Machines commonly used for sequencing include the ABI PRISM 3700, 377 or 373 DNA sequencing systems (ABI), the MEGABACE 1000 DNA sequencing system (APB), and the like. The sequences may be analyzed using a variety of algorithms well known in the art and described in Ausubel et al (1997; *Short Protocols in Molecular Biology*, John Wiley & Sons, New York N.Y., unit 7.7) and in Meyers (1995; *Molecular Biology and Biotechnology*, Wiley VCH, New York N.Y., pp. 856-853).

Shotgun sequencing may also be used to complete the sequence of a particular cloned insert of interest. Shotgun strategy involves randomly breaking the original insert into segments of various sizes and cloning these fragments into vectors. The fragments are sequenced and reassembled using overlapping ends until the entire sequence of the original insert is known. Shotgun sequencing methods are well known in the art and use thermostable DNA polymerases, heat-labile DNA polymerases, and primers chosen from representative regions flanking the cDNAs of interest. Incomplete assembled sequences are inspected for identity using various algorithms or programs such as CONSED (Gordon (1998) Genome Res 8:195-202) which are well known in the art. Contaminating sequences, including vector or chimeric sequences, or deleted sequences can be removed or restored, respectively, organizing the incomplete assembled sequences into finished sequences.

Extension of a Nucleic Acid Molecule

The sequences of the invention may be extended using various PCR-based methods known in the art. For example, the XL-PCR kit (ABI), nested primers, and commercially available cDNA or genomic DNA libraries may be used to extend the . For all PCR-based methods, primers may be designed using commercially available software to be about 22 to 30 nucleotides in length, to have a GC content of about 50% or more, and to anneal to a target molecule at temperatures from about 55 C to about 68 C. When extending a sequence to recover regulatory elements, it is preferable to use genomic, rather than cDNA libraries.

Hybridization

The cDNA and fragments thereof can be used in hybridization technologies for various purposes. A probe may be designed or derived from unique regions such as the 5' regulatory region or from a nonconserved region (i.e., 5' or 3' of the nucleotides encoding the conserved catalytic domain of the protein) and used in protocols to identify naturally occurring molecules encoding a signal peptide-containing protein, allelic variants, or related molecules. The probe may be DNA or RNA, may be single-stranded, and should have at least 50% sequence identity to a nucleic acid molecule selected from SEQ ID NOs:1-15 and 17-78. Hybridization probes may be produced using oligolabeling, nick translation, end-labeling, or PCR amplification in the presence of a reporter molecule. A vector containing the cDNA or a fragment thereof may be used to produce an mRNA probe in vitro by addition of an RNA polymerase and labeled nucleotides. These procedures may be conducted using commercially available kits.

The stringency of hybridization is determined by G+C content of the probe, salt concentration, and temperature. In particular, stringency can be increased by reducing the concentration of salt or raising the hybridization temperature. Hybridization can be performed at low stringency with buffers, such as 5×SSC with 1% sodium dodecyl sulfate (SDS) at 60 C, which permits the formation of a hybridization complex between s that contain some mismatches. Subsequent washes are performed at higher stringency with buffers such as 0.2×SSC with 0.1% SDS at either 45 C (medium stringency) or 68 C (high stringency). At high stringency, hybridization complexes will remain stable only where the nucleic acids are completely complementary. In some membrane-based hybridizations, preferably 35% or most preferably 50%, formamide can be added to the hybridization solution to reduce the temperature at which hybridization is performed, and background signals can be reduced by the use of detergents such as Sarkosyl or TRITON X-100 (Sigma-Aldrich, St Louis Mo.) and a blocking agent such as denatured salmon sperm DNA. Selection of components and conditions for hybridization are well known to those skilled in the art and are reviewed in Ausubel (supra) and Sambrook et al (1989) *Molecular Cloning, A Laboratory Manual*, Cold Spring Harbor Press, Plainview N.Y.

Arrays incorporating cDNAs or antibodies may be prepared and analyzed using methods well known in the art. Oligonucleotides or cDNAs may be used as hybridization probes or targets to monitor the expression level of large numbers of genes simultaneously or to identify genetic variants, mutations, and single nucleotide polymorphisms. Monoclonal or polyclonal antibodies may be used to detect or quantify expression of a protein in a sample. Such arrays may be used to determine gene function; to understand the genetic basis of a condition, disease, or disorder; to diagnose a condition, disease, or disorder; and to develop and monitor the activities of therapeutic agents. (See, e.g., Brennan et al (1995) U.S. Pat. No. 5,474,796; Schena et al (1996) Proc Natl Acad Sci 93:10614-10619; Heller et al (1997) Proc Natl Acad Sci 94:2150-2155; Heller et al (1997) U.S. Pat. No. 5,605,662; and deWildt et al (2000) Nature Biotechnol 18:989-994.)

Hybridization probes are also useful in mapping the naturally occurring genomic sequence. The probes may be hybridized to a particular chromosome, a specific region of a chromosome, or an artificial chromosome construction. Such constructions include human artificial chromosomes (HAC), yeast artificial chromosomes (YAC), bacterial artificial chromosomes (BAC), bacterial P1 constructions, or the cDNAs of libraries made from single chromosomes.

Expression

Any one of a multitude of cDNAs encoding a signal peptide-containing protein may be cloned into a vector and used to express the protein, or portions thereof, in host cells. The can be engineered by such methods as DNA shuffling, as described in U.S. Pat. No. 5,830,721, and site-directed mutagenesis to create new restriction sites, alter glycosylation patterns, change codon preference to increase expression in a particular host, produce splice variants, extend half-life, and the like. The expression vector may contain transcriptional and translational control elements (promoters, enhancers, specific initiation signals, and polyadenylated 3' sequence) from various sources which have been selected for their efficiency in a particular host. The vector, cDNA, and regulatory elements are combined using in vitro recombinant DNA techniques, synthetic techniques, and/or in vivo genetic recombination techniques well known in the art and described in Sambrook (supra, ch. 4, 8, 16 and 17).

A variety of host systems may be transformed with an expression vector. These include, but are not limited to, bacteria transformed with recombinant bacteriophage, plasmid, or cosmid DNA expression vectors; yeast transformed with yeast expression vectors; insect cell systems transformed with baculovirus expression vectors; plant cell systems transformed with expression vectors containing viral and/or bacterial elements, or animal cell systems (Ausubel supra, unit 16). For example, an adenovirus transcription/translation complex may be utilized in mammalian cells. After sequences are ligated into the E1 or E3 region of the viral genome, the infective virus is used to transform and express the protein in host cells. The Rous sarcoma virus enhancer or SV40 or EBV-based vectors may also be used for high-level protein expression.

Routine cloning, subcloning, and propagation of s can be achieved using the multifunctional PBLUESCRIPT vector (Stratagene, La Jolla Calif.) or PSPORT1 plasmid (Life Technologies).

Introduction of a into the multiple cloning site of these vectors disrupts the lacZ gene and allows colorimetric screening for transformed bacteria. In addition, these vectors may be useful for in vitro transcription, dideoxy sequencing, single strand rescue with helper phage, and creation of nested deletions in the cloned sequence.

For long term production of recombinant proteins, the vector can be stably transformed into cell lines along with a selectable or visible marker gene on the same or on a separate vector. After transformation, cells are allowed to grow for about 1 to 2 days in enriched media and then are transferred to selective media. Selectable markers, antimetabolite, antibiotic, or herbicide resistance genes, confer resistance to the relevant selective agent and allow growth and recovery of cells which successfully express the introduced sequences. Resistant clones identified either by survival on selective media or by the expression of visible markers may be propagated using culture techniques. Visible markers are also used to estimate the amount of protein expressed by the introduced genes. Verification that the host cell contains the desired cDNA is based on DNA-DNA or DNA-RNA hybridizations or PCR amplification techniques.

The host cell may be chosen for its ability to modify a recombinant protein in a desired fashion.

Such modifications include acetylation, carboxylation, glycosylation, phosphorylation, lipidation, acylation and the like. Post-translational processing which cleaves a "prepro" form may also be used to specify protein targeting, folding, and/or activity. Different host cells available from the ATCC (Manassas Va.) which have specific cellular machinery and characteristic mechanisms for post-translational activities may be chosen to ensure the correct modification and processing of the recombinant protein.

Recovery of Proteins from Cell Culture

Heterologous moieties engineered into a vector for ease of purification include glutathione S-transferase (GST), 6×His, FLAG, MYC, and the like. GST and 6×His are purified using commercially available affinity matrices such as immobilized glutathione and metal-chelate resins, respectively. FLAG and MYC are purified using commercially available monoclonal and polyclonal antibodies. For ease of separation following purification, a sequence encoding a proteolytic cleavage site may be part of the vector located between the protein and the heterologous moiety. Methods for recombinant protein expression and purification are discussed in Ausubel (supra, unit 16) and are commercially available.

Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinyl-benzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full length peptide is synthesized by sequential deprotection, coupling of derivitized amino acids, and washing with dichloromethane and/or N,N-dimethylformamide. The peptide is cleaved between the peptide carboxy terminus and the linker group to yield a peptide acid or amide. These processes are described in the Novabiochem 1997/98 Catalog and Peptide Synthesis Handbook (San Diego Calif. pp. S1-S20). Automated synthesis may also be carried out on machines such as the ABI 431A peptide synthesizer (ABI). A protein or portion thereof may be purified by preparative high performance liquid chromatography and its composition confirmed by amino acid analysis or by sequencing (Creighton (1984) *Proteins, Structures and Molecular Properties*, WH Freeman, New York N.Y.).

Preparation and Screening of Antibodies

Various hosts including, but not limited to, goats, rabbits, rats, mice, and human cell lines may be immunized by injection with a signal peptide-containing protein or any immunogenic portion thereof. Adjuvants such as Freund's, mineral gels, and surface active substances such as lysolecithin, pluronic polyols, polyanions, peptides, oil emulsions, keyhole limpet hemacyanin (KLH), and dinitrophenol may be used to increase immunological response. The oligopeptide, peptide, or portion of protein used to induce antibodies should consist of at least about five amino acids, more preferably ten amino acids, which are identical to a portion of the natural protein. Oligopeptides may be fused with proteins such as KLH in order to produce antibodies to the chimeric molecule.

Monoclonal antibodies may be prepared using any technique which provides for the production of antibodies by continuous cell lines in culture. These include, but are not limited to, the hybridoma technique, the human B-cell hybridoma technique, and the EBV-hybridoma technique. (See, e.g., Kohler et al (1975) Nature 256:495-497; Kozbor et al (1985) J. Immunol Methods 81:31-42; Cote et al (1983) Proc Natl Acad Sci 80:2026-2030; and Cole et al (1984) Mol Cell Biol 62:109-120.)

Alternatively, techniques described for antibody production may be adapted, using methods known in the art, to produce epitope-specific, single chain antibodies. Antibody fragments which contain specific binding sites for epitopes of the protein may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse et al (1989) Science 246:1275-1281.)

A signal peptide-containing protein, or a portion thereof, may be used in screening assays of phagemid or B-lymphocyte immunoglobulin libraries to identify antibodies having the desired specificity. Numerous protocols for competitive binding or immunoassays using either polyclonal or monoclonal antibodies with established specificities are well known in the art. Such immunoassays typically involve the measurement of complex formation between the protein and its specific antibody. A two-site, monoclonal-based immunoassay utilizing monoclonal antibodies reactive to two non-interfering epitopes is preferred, but a competitive binding assay may also be employed (Pound (1998) *Immunochemical Protocols*, Humana Press, Totowa N.J.).

Labeling of Molecules for Assay

A wide variety of reporter molecules and conjugation techniques are known by those skilled in the art and may be used in various nucleic acid, amino acid, and antibody assays. Synthesis of labeled molecules may be achieved using commercially available kits (Promega, Madison Wis.) for incorporation of a labeled nucleotide such as $^{32}$P-dCTP (APB), Cy3-dCTP or Cy5-dCTP (Operon Technologies, Alameda Calif.), or amino acid such as $^{35}$S-methionine (APB). Nucleotides and amino acids may be directly labeled with a variety of substances including fluorescent, chemiluminescent, or chromogenic agents, and the like, by chemical conjugation to amines, thiols and other groups present in the molecules using reagents such as BIODIPY or FITC (Molecular Probes, Eugene Oreg.).

Diagnostics

Nucleic Acid Assays

The cDNAs, fragments, oligonucleotides, complementary RNA and DNA molecules, and PNAs may be used to detect and quantify differential gene expression for diagnostic purposes. Disorders associated with expression of SP-1 through SP-16 include, but are not limited to, adenofibromatous hyperplasia as a prognostic of prostate cancer, asthma, arthritis, breast cancers such as ductal, lobular. and adeno-carcinomas, Huntington's disease, mucinous cystadenoma of the ovary, renal cell cancer, schizophrenia stomach tumor, testicular seminoma, transitional cell carcinoma of the bladder, and uterine adenosquamous carcinoma. The diagnostic assay may use hybridization or quantitative PCR to compare gene expression in a biological or biopsied subject sample to standard samples in order to detect differential gene expression. Qualitative and quantitative methods for this comparison are commercially available and well known in the art.

For example, the cDNA or probe may be labeled by standard methods and added to a biological sample from a subject under conditions for the formation of hybridization complexes. After an incubation period, the sample is washed and the amount of label (or signal) associated with hybridization complexes, is quantified and compared with a standard value. If complex formation in the subject sample is significantly altered (higher or lower) in comparison to either a normal or disease standard, then differential expression indicates the presence of a disorder.

In order to provide standards for establishing differential expression, normal and disease expression profiles are established. This is accomplished by combining a sample taken from normal subjects, either animal or human, with a cDNA under conditions for hybridization to occur. Standard hybridization complexes may be quantified by comparing the values obtained using normal subjects with values from an experiment in which a known amount of a purified sequence is used. Standard values obtained in this manner may be compared with values obtained from samples from patients who were diagnosed with a particular condition, disease, or disorder. Deviation from standard values toward those associated with a particular disorder is used to diagnose that disorder.

Such assays may also be used to evaluate the efficacy of a particular therapeutic treatment regimen in animal studies or in clinical trials or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to years.

Protein Assays

Detection and quantification of a protein using either labeled amino acids or specific polyclonal or monoclonal antibodies which specifically bind the protein are known in the art. Examples of such techniques include two-dimensional polyacrylamide gel electrophoresis, enzyme-linked immunosorbent assays (ELISAs), radioimmunoassays (RIAs), and fluorescence activated cell sorting (FACS). These assays and their quantitation against purified, labeled standards are well known in the art (Ausubel, supra, unit 10.1-10.6). A two-site, monoclonal-based immunoassay utilizing monoclonal antibodies reactive to two non-interfering epitopes is preferred, but a competitive binding assay may be employed. (See, e.g., Coligan et al (1997) *Current Protocols in Immunology*, Wiley-Interscience, New York N.Y.; and Pound, supra.)

Therapeutics

Chemical and structural similarity, in particular annotation and motifs that suggest function, are described for SEQ ID NO:16 in THE INVENTION section and transcript images that suggest function for the proteins encoded or regulated by SEQ ID NO:1-15 are described in EXAMPLE VIII and EXAMPLE IX. In addition, the differential expression of each of the cDNAs was shown to be tissue-specific and associated with a particular disorder in EXAMPLE VIII. Thus, each protein clearly plays a role in at least one of the described disorders (adenofibromatous hyperplasia as a prognostic of prostate cancer, asthma, arthritis, breast cancers such as ductal, lobular, and adeno-carcinomas, Huntington's disease, mucinous cystadenoma of the ovary, renal cell cancer, schizophrenia stomach tumor, testicular seminoma, transitional cell carcinoma of the bladder, and uterine adenosquamous carcinoma) and SP-1 through SP-16 may be used either directly as a therapeutic or as a target for drug discovery.

In one embodiment, increased expression of the protein may be treated by the delivery of an inhibitor, antagonist, antibody and the like or a pharmaceutical composition containing one or more of these molecules. Such delivery may be effected by methods well known in the art and may include delivery by an antibody specifically targeted to the diseased tissue. In another embodiment, decreased expression of the protein late in the disease process may be treated by the delivery of the protein, an agonist, enhancer and the like or a pharmaceutical composition containing one or more of these molecules. Such delivery may be effected by methods well known in the art and may include delivery by an antibody specifically targeted to the diseased tissue.

Any of these compositions may be administered in combination with other therapeutic agents. Selection of the agents for use in combination therapy may be made by one of ordinary skill in the art according to conventional pharmaceutical principles. A combination of therapeutic agents may act synergistically to affect treatment of a particular cancer at a lower dosage of each agent alone.

Modification of Gene Expression Using Nucleic Acids

Gene expression may be modified by designing complementary or antisense molecules (DNA, RNA, or PNA) to the control, 5', 3', or other regulatory regions of the gene encoding a signal peptide-containing protein. Oligonucleotides designed to inhibit transcription initiation are preferred. Similarly, inhibition can be achieved using triple helix base-pairing which inhibits the binding of polymerases, transcription factors, or regulatory molecules (Gee et al In: Huber and Carr (1994) *Molecular and Immunologic Approaches*, Futura Publishing, Mt. Kisco N.Y., pp. 163-177). A complementary molecule may also be designed to block translation by preventing binding between ribosomes and mRNA. In one alternative, a library or plurality of cDNAs may be screened to identify those which specifically bind a regulatory, nontranslated sequence.

Ribozymes, enzymatic RNA molecules, may also be used to catalyze the specific cleavage of RNA. The mechanism of ribozyme action involves sequence-specific hybridization of the ribozyme molecule to complementary target RNA followed by endonucleolytic cleavage at sites such as GUA, GUU, and GUC. Once such sites are identified, an oligonucleotide with the same sequence may be evaluated for secondary structural features which would render the oligonucleotide inoperable. The suitability of candidate targets may also be evaluated by testing their hybridization with complementary oligonucleotides using ribonuclease protection assays.

Complementary nucleic acids and ribozymes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothioate or 2' O-methyl rather than phosphodiesterase linkages within the backbone of the molecule. Modification is inherent in the production of PNAs and can be extended to other nucleic acid molecules. Either the inclusion of nontraditional bases such as inosine, queosine, and wybutosine, or the modification of adenine, cytidine, guanine, thymine, and uridine with acetyl-, methyl-, thio- groups renders the molecule less available to endogenous endonucleases.

Screening and Purification Assays

A cDNA encoding a signal peptide-containing protein may be used to screen a library or a plurality of molecules or compounds for specific binding affinity. The libraries may be aptamers, DNA molecules, RNA molecules, PNAs, peptides, proteins such as transcription factors, enhancers, or repressors, and other ligands which regulate the activity, replication, transcription, or translation of the endogenous gene. The assay involves combining a polynucleotide with a library or plurality of molecules or compounds under conditions allowing specific binding, and detecting specific binding to identify at least one molecule which specifically binds the single-stranded or double-stranded molecule.

In one embodiment, the cDNA of the invention may be incubated with a plurality of purified molecules or compounds and binding activity determined by methods well known in the art, e.g., a gel-retardation assay (U.S. Pat. No. 6,010,849) or a commercially available reticulocyte lysate transcriptional assay. In another embodiment, the cDNA may be incubated with nuclear extracts from biopsied and/or cultured cells and tissues. Specific binding between the cDNA and a molecule or compound in the nuclear extract is initially determined by gel shift assay and may be later confirmed by recovering and raising antibodies against that molecule or compound. When these antibodies are added into the assay, they cause a supershift in the gel-retardation assay.

In another embodiment, the cDNA may be used to purify a molecule or compound using affinity chromatography methods well known in the art. In one embodiment, the cDNA is chemically reacted with cyanogen bromide groups on a polymeric resin or gel. Then a sample is passed over and reacts with or binds to the cDNA. The molecule or compound which is bound to the cDNA may be released from the cDNA by increasing the salt concentration of the flow-through medium and collected.

In a further embodiment, the protein or a portion thereof may be used to purify a ligand from a sample. A method for using a protein or a portion thereof to purify a ligand would involve combining the protein or a portion thereof with a sample under conditions to allow specific binding, detecting specific binding between the protein and ligand, recovering the bound protein, and using a chaotropic agent to separate the protein from the purified ligand.

In a preferred embodiment, a signal peptide-containing protein may be used to screen a plurality of molecules or compounds in any of a variety of screening assays. The portion of the protein employed in such screening may be free in solution, affixed to an abiotic or biotic substrate (e.g. borne on a cell surface), or located intracellularly. For example, in one method, viable or fixed prokaryotic host cells that are stably transformed with recombinant nucleic acids that have expressed and positioned a peptide on their cell surface can be used in screening assays. The cells are screened against a plurality or libraries of ligands, and the specificity of binding or formation of complexes between the expressed protein and the ligand can be measured. Depending on the particular kind of molecules or compounds being screened, the assay may be used to identify DNA molecules, RNA molecules, peptide nucleic acids, peptides, proteins, mimetics, agonists, antagonists, antibodies, immunoglobulins, inhibitors, and drugs or any other ligand, which specifically binds the protein.

In one aspect, this invention comtemplates a method for high throughput screening using very small assay volumes and very small amounts of test compound as described in U.S. Pat. No. 5,876,946, incorporated herein by reference. This method is used to screen large numbers of molecules and compounds via specific binding. In another aspect, this invention also contemplates the use of competitive drug screening assays in which neutralizing antibodies capable of binding the protein specifically compete with a test compound capable of binding to the protein. Molecules or compounds identified by screening may be used in a model system to evaluate their toxicity, diagnostic, or therapeutic potential.

Pharmacology

Pharmaceutical compositions contain active ingredients in an effective amount to achieve a desired and intended purpose and a pharmaceutical carrier. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of protein or inhibitor which ameliorates the symptoms or condition. Therapeutic efficacy and toxicity of such agents may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it may be expressed as the ratio, $LD_{50}/ED_{50}$. Pharmaceutical compositions which exhibit large therapeutic indexes are preferred. The data obtained from cell culture assays and animal studies are used in formulating a range of dosage for human use.

Model Systems

Animal models may be used as bioassays where they exhibit a phenotypic response similar to that of humans and where exposure conditions are relevant to human exposures. Mammals are the most common models, and most infectious agent, cancer, drug, and toxicity studies are performed on rodents such as rats or mice because of low cost, availability, lifespan, reproductive potential, and abundant reference literature. Inbred and outbred rodent strains provide a convenient model for investigation of the physiological consequences of under- or over-expression of genes of interest and for the development of methods for diagnosis and treatment of diseases. A mammal inbred to over-express a particular gene (for example, secreted in milk) may also serve as a convenient source of the protein expressed by that gene.

Toxicology

Toxicology is the study of the effects of agents on living systems. The majority of toxicity studies are performed on rats or mice. Observation of qualitative and quantitative changes in physiology, behavior, homeostatic processes, and lethality in the rats or mice are used to generate a toxicity profile and to assess potential consequences on human health following exposure to the agent.

Genetic toxicology identifies and analyzes the effect of an agent on the rate of endogenous, spontaneous, and induced genetic mutations. Genotoxic agents usually have common chemical or physical properties that facilitate interaction with nucleic acids and are most harmful when chromosomal aberrations are transmitted to progeny. Toxicological studies may identify agents that increase the frequency of structural or functional abnormalities in the tissues of the progeny if administered to either parent before conception, to the mother during pregnancy, or to the developing organism. Mice and rats are most frequently used in these tests because their short reproductive cycle allows the production of the numbers of organisms needed to satisfy statistical requirements.

Acute toxicity tests are based on a single administration of an agent to the subject to determine the symptomology or lethality of the agent. Three experiments are conducted: 1) an initial dose-range-finding experiment, 2) an experiment to narrow the range of effective doses, and 3) a final experiment for establishing the dose-response curve.

Subchronic toxicity tests are based on the repeated administration of an agent. Rat and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Transgenic Animal Models

Transgenic rodents that over-express or under-express a gene of interest may be inbred and used to model human diseases or to test therapeutic or toxic agents. (See, e.g., U.S. Pat. No. 5,175,383 and U.S. Pat. No. 5,767,337.) In some cases, the introduced gene may be activated at a specific time in a specific tissue type during fetal or postnatal development. Expression of the transgene is monitored by analysis of phenotype, of tissue-specific mRNA expression, or of serum and tissue protein levels in transgenic animals before, during, and after challenge with experimental drug therapies.

Embryonic Stem Cells

Embryonic (ES) stem cells isolated from rodent embryos retain the potential to form embryonic tissues. When ES cells are placed inside a carrier embryo, they resume normal development and contribute to tissues of the live-born animal. ES cells are the preferred cells used in the creation of experimental knockout and knockin rodent strains. Mouse ES cells, such as the mouse 129/SvJ cell line, are derived from the early mouse embryo and are grown under culture conditions well known in the art. Vectors used to produce a transgenic strain contain a disease gene candidate and a marker gen, the latter serves to identify the presence of the introduced disease gene. The vector is transformed into ES cells by methods well known in the art, and transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains.

ES cells derived from human blastocysts may be manipulated in vitro to differentiate into at least eight separate cell lineages. These lineages are used to study the differentiation of various cell types and tissues in vitro, and they include endoderm, mesoderm, and ectodermal cell types which differentiate into, for example, neural cells, hematopoietic lineages, and cardiomyocytes.

Knockout Analysis

In gene knockout analysis, a region of a gene is enzymatically modified to include a non-mammalian gene such as the neomycin phosphotransferase gene (neo; Capecchi (1989) Science 244:1288-1292). The modified gene is transformed into cultured ES cells and integrates into the endogenous genome by homologous recombination. The inserted sequence disrupts transcription and translation of the endogenous gene. Transformed cells are injected into rodent blastulae, and the blastulae are implanted into pseudopregnant dams. Transgenic progeny are crossbred to obtain homozygous inbred lines which lack a functional copy of the mammalian gene. In one example, the mammalian gene is a human gene.

Knockin Analysis

ES cells can be used to create knockin humanized animals (pigs) or transgenic animal models (mice or rats) of human diseases. With knockin technology, a region of a human gene is injected into animal ES cells, and the human sequence integrates into the animal cell genome. Transformed cells are injected into blastulae and the blastulae are implanted as described above. Iransgenic progeny or inbred lines are studied and treated with potential pharmaceutical agents to obtain information on treatment of the analogous human condition. These methods have been used to model several human diseases.

Non-Human Primate Model

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human surrogates in vaccine and drug evaluations, and their responses are relevant to human exposures under similar conditions. Cynomolgus and Rhesus monkeys (*Macaca fascicularis* and *Macaca mulatta*, respectively) and Common Marmosets (*Callithrix jacchus*) are the most common non-human primates (NHPs) used in these investigations. Since great cost is associated with developing and maintaining a colony of NHPs, early research and toxicological studies are usually carried out in rodent models. In studies using behavioral measures such as drug addiction, NHPs are the first choice test animal. In addition, NHPs and individual humans exhibit differential sensitivities to many drugs and toxins and can be classified as a range of phenotypes from "extensive metabolizers" to "poor metabolizers" of these agents.

In additional embodiments, the cDNAs which encode the protein may be used in any molecular biology techniques that have yet to be developed, provided the new techniques rely on properties of cDNAs that are currently known, including, but not limited to, such properties as the triplet genetic code and specific base pair interactions.

EXAMPLES

I cDNA Library Construction

The UTRSNOT11 cDNA library was constructed from microscopically normal uterine tissue obtained from a 43-year-old female during a vaginal hysterectomy following diagnosis of uterine leiomyoma. Pathology indicated that the myometrium contained an intramural leiomyoma and a submucosal leiomyoma. The endometrium was proliferative, however, the cervix and fallopian tubes were unremarkable. The right and left ovaries contained corpus lutea. The patient presented with metrorrhagia and deficiency anemia. Patient history included benign hypertension and atherosclerosis. Medications included PROVERA tablets (Pharmacia, Peapack N.J.), iron, and vitamins. Family history included benign hypertension, atherosclerosis, and malignant colon neoplasms.

The frozen tissue was homogenized and lysed in TRIZOL reagent (1 gm tissue/10 ml reagent; Life Technologies) using a POLYTRON homogenizer (PT-3000; Brinkmann Instruments, Westbury N.Y.). After a brief incubation on ice, chloroform was added (1:5 v/v), and the lysate was centrifuged. The upper chloroform layer was removed to a fresh tube, and the RNA was extracted with isopropanol, resuspended in DEPC-treated water, and treated with DNAse for 25 min at 37 C. The RNA was re-extracted three times with acid phenol-chloroform, pH 4.7, and precipitated with 0.3 M sodium acetate and 2.5 volumes ethanol. The mRNA was isolated with the OLIGOTEX kit (Qiagen, Chatsworth Calif.) and used to construct the cDNA library.

The mRNA was handled according to the recommended protocols in the SUPERSCRIPT plasmid system (Life Technologies). The cDNAs were fractionated on a SEPHAROSE CL4B column (APB), and those cDNAs exceeding 400 bp were ligated into pINCY1 plasmid. The plasmid was subsequently transformed into DH5α competent cells (Life Technologies).

II Isolation of cDNA Clones

Plasmid DNA was released from the cells and purified using the REAL PREP 96 plasmid kit (Qiagen). This kit enabled the simultaneous purification of 96 samples in a 96-well block using multi-channel reagent dispensers. The recommended protocol was employed except for the following changes: 1) the bacteria were cultured in 1 ml of sterile TERRIFIC BROTH (BD Biosciences, San Jose Calif.) with carbenicillin at 25 mg/L and glycerol at 0.4%; 2) after incubation for 19 hours, the cultures were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4 C.

III Sequencing

The cDNAs were prepared for sequencing using the MICROLAB 2200 system (Hamilton) in combination with the DNA ENGINE thermal cyclers (MJ Research). The cDNAs were sequenced by the method of Sanger and Coulson (1975; J Mol Biol 94:441-448) using an ABI PRISM 373 or 377 sequencing system (ABI). Most of the isolates were sequenced according to standard ABI protocols and kits with solution volumes of 0.25×-1.0× concentrations or using standard solutions and dyes from APB.

IV Extension of cDNA Sequences

The cDNA sequence may be extended to full length using the Incyte clone, for example, SEQ ID NO:17, 2547002H1. A set of nested deletion sequencing templates was prepared from overnight liquid culture of clone 496071 using the ERASE-A-BASE system (Promega).

Sequencing reactions were performed with the ABI PRISM Dye Terminator cycle sequencing kit with AMPLI-TAQ FS DNA polymerase (ABI). PCR was performed on a DNA ENGINE thermal cycler (MJ Research). Reactions were analyzed on an ABI PRISM 310 genetic analyzer (ABI). Individual sequences were assembled and edited using ABI AutoAssembler software (ABI).

In the alternative, extension is accomplished using oligonucleotide primers synthesized to initiate 5' and 3' extension of the known fragment. These primers are designed using commercially available primer analysis software to be about 22 to 30 nucleotides in length, to have a GC content of about 50% or more, and to anneal to the target sequence at temperatures of about 68 C to about 72 C. Any stretch of nucleotides that would result in hairpin structures and primer-primer dimerizations is avoided.

Selected cDNA libraries are used as templates to extend the sequence. If more than one extension is necessary, additional or nested sets of primers are designed. Preferred libraries have been size-selected to include larger cDNAs and random primed to contain more sequences with 5' or upstream regions of genes. Genomic libraries are used to obtain regulatory elements, especially extension into the 5' promoter binding region.

High fidelity amplification is obtained by PCR using methods such as that taught in U.S. Pat. No. 5,932,451. PCR is performed in 96-well plates using the DNA ENGINE thermal cycler (MJ Research). The reaction mix contains DNA template, 200 mmol of each primer, reaction buffer containing $Mg^{2+}$, $(NH_4)_2SO_4$, and β-mercaptoethanol, Taq DNA polymerase (APB), ELONGASE enzyme (Life Technologies), and Pfu DNA polymerase (Stratagene), with the following parameters for primer pair PCI A and PCI B (Incyte Genomics): Step 1: 94 C, three min; Step 2: 94 C, 15 sec; Step 3: 60 C, one min; Step 4: 68 C, two min; Step 5: Steps 2, 3, and 4 repeated 20 times; Step 6: 68 C, five min; Step 7: storage at 4 C. In the alternative, the parameters for primer pair T7 and SK+ (Stratagene) are as follows: Step 1: 94 C, three min; Step 2: 94 C, 15 sec; Step 3: 57 C, one min; Step 4: 68 C, two min; Step 5: Steps 2, 3, and 4 repeated 20 times; Step 6: 68 C, five min; Step 7: storage at 4 C.

The concentration of DNA in each well is determined by dispensing 100 μl PICOGREEN quantitation reagent (0.25% reagent in 1×TE, v/v; Molecular Probes) and 0.5 μl of undiluted PCR product into each well of an opaque fluorimeter plate (Corning, Acton Mass.) and allowing the DNA to bind to the reagent. The plate is scanned in a Fluoroskan II (Labsystems Oy, Finland) to measure the fluorescence of the sample and to quantify the concentration of DNA. A 5 μl to 10 μl aliquot of the reaction mixture is analyzed by electrophoresis on a 1% agarose minigel to determine which reactions are successful in extending the sequence.

The extended clones are desalted, concentrated, transferred to 384-well plates, digested with CviJI cholera virus endonuclease (Molecular Biology Research, Madison Wis.), and sonicated or sheared prior to religation into pUC18 vector (APB). For shotgun sequences, the digested nucleotide sequences are separated on low concentration (0.6 to 0.8%) agarose gels, fragments are excised, and the agar is digested with AGARACE enzyme (Promega). Extended clones are religated using T4 DNA ligase (New England Biolabs) into pUC18 vector (APB), treated with Pfu DNA polymerase (Stratagene) to fill-in restriction site overhangs, and transfected into E. coli competent cells. Transformed cells are selected on antibiotic-containing media, and individual colonies are picked and cultured overnight at 37 C in 384-well plates in LB/2× carbenicillin liquid media.

The cells are lysed, and DNA is amplified using primers, Taq DNA polymerase (APB) and Pfu DNA polymerase (Stratagene) with the following parameters: Step 1: 94 C, three min; Step 2: 94 C, 15 sec; Step 3: 60 C, one min; Step 4: 72 C, two min; Step 5: steps 2, 3, and 4 repeated 29 times; Step 6: 72 C, five min; Step 7: storage at 4 C DNA is quantified using PICOGREEN quantitation reagent (Molecular Probes) as described above. Samples with low DNA recoveries are reamplified using the conditions described above. Samples are diluted with 20% dimethylsulfoxide (DMSO; 1:2, v/v), and sequenced using DYENAMIC energy transfer sequencing primers and the DYENAMIC DIRECT cycle sequencing kit (APB) or the PRISM BIG-DYE. terminator cycle sequencing kit (ABI).

V Homology Searching of cDNA Clones and Their Deduced Proteins

The cDNAs of the Sequence Listing or their deduced amino acid sequences were used to query databases such as GenBank, SwissProt, BLOCKS, and the like. These databases that contain previously identified and annotated sequences or domains were searched using BLAST or BLAST2 to produce alignments and to determine which sequences were exact matches or homologs. The alignments were to sequences of prokaryotic (bacterial) or eukaryotic (animal, fungal, or plant) origin. Alternatively, algorithms such as the one described in Smith and Smith (1992, Protein Engineering 5:35-51) could have been used to deal with primary sequence patterns and secondary structure gap penalties. All of the sequences disclosed in this application have lengths of at least 49 nucleotides, and no more than 12% uncalled bases (where N is recorded rather than A, C, G, or T).

As detailed in Karlin (supra), BLAST matches between a query sequence and a database sequence were evaluated statistically and only reported when they satisfied the threshold of $10^{-25}$ for nucleotides and $10^{-14}$ for peptides. Homology was also evaluated by product score calculated as follows: the % nucleotide or amino acid identity [between the query and reference sequences] in BLAST is multiplied by the % maximum possible BLAST score [based on the lengths of query and reference sequences] and then divided by 100. In comparison with hybridization procedures used in the laboratory, the stringency for an exact match was set from a lower limit of about 40 (with 1-2% error due to uncalled bases) to a 100% match of about 70.

The BLAST software suite (NCBI, Bethesda Md.; http://www.ncbi.nlm.nih.gov/gorf/bl2.html), includes various sequence analysis programs including "blastn" that is used to align nucleotide sequences and BLAST2 that is used for direct pairwise comparison of either nucleotide or amino acid sequences. BLAST programs are commonly used with gap and other parameters set to default settings, e.g.: Matrix: BLOSUM62; Reward for match: 1; Penalty for mismatch: −2; Open Gap: 5 and Extension Gap: 2 penalties; Gap×drop-off: 50; Expect: 10; Word Size: 11; and Filter: on. Identity is measured over the entire length of a sequence. Brenner et al (1998; Proc Natl Acad Sci 95:6073-6078, incorporated herein by reference) analyzed BLAST for its ability to identify structural homologs by sequence identity and found 30% identity is a reliable threshold for sequence alignments of at least 150 residues and 40%, for alignments of at least 70 residues.

The cDNAs of this application were compared with assembled consensus sequences or templates found in the LIFESEQ GOLD database (Incyte Genomics). Component sequences from cDNA, extension, full length, and shotgun sequencing projects were subjected to PHRED analysis and assigned a quality score. All sequences with an acceptable quality score were subjected to various pre-processing and editing pathways to remove low quality 3'ends, vector and linker sequences, polyA tails, Alu repeats, mitochondrial and ribosomal sequences, and bacterial contamination sequences. Edited sequences had to be at least 50 bp in length, and low-information sequences and repetitive elements such as dinucleotide repeats, Alu repeats, and the like, were replaced by "Ns" or masked.

Edited sequences were subjected to assembly procedures in which the sequences were assigned to gene bins. Each sequence could only belong to one bin, and sequences in each bin were assembled to produce a template. Newly sequenced components were added to existing bins using BLAST and CROSSMATCH. To be added to a bin, the component sequences had to have a BLAST quality score greater than or equal to 150 and an alignment of at least 82% local identity. The sequences in each bin were assembled using PHRAP. Bins with several overlapping component sequences were assembled using DEEP PHRAP. The orientation of each template was determined based on the number and orientation of its component sequences.

Bins were compared to one another, and those having local similarity of at least 82% were combined and reassembled. Bins having templates with less than 95% local identity were split. Templates were subjected to analysis by STITCHER/EXON MAPPER algorithms that determine the probabilities of the presence of splice variants, alternatively spliced exons, splice junctions, differential expression of alternative spliced genes across tissue types or disease states, and the like. Assembly procedures were repeated periodically, and templates were annotated using BLAST against GenBank databases such as GBpri. An exact match was defined as having from 95% local identity over 200 base pairs through 100% local identity over 100 base pairs and a homolog match as having an E-value (or probability score) of $\leq 1 \times 10^{-8}$. The templates were also subjected to frameshift FASTx against GENPEPT, and homolog match was defined as having an E-value of $\leq 1 \times 10^{-8}$. Template analysis and assembly was described in U.S. Ser. No. 09/276,534, filed Mar. 25, 1999.

Following assembly, templates were subjected to BLAST, motif, and other functional analyses and categorized in protein hierarchies using methods described in U.S. Ser. No. 08/812,290 and U.S. Ser. No. 08/811,758, both filed Mar. 6, 1997; in U.S. Ser. No. 08/947,845, filed Oct. 9, 1997; and in U.S. Ser. No. 09/034,807, filed Mar. 4, 1998. Then templates were analyzed by translating each template in all three forward reading frames and searching each translation against the PFAM database of hidden Markov model-based protein families and domains using the HMMER software package (Washington University School of Medicine, St. Louis Mo.; http://pfam.wustl.edu/). The cDNA was further analyzed using MACDNASIS PRO software (Hitachi Software Engineering), and LASERGENE software (DNASTAR) and queried against public databases such as the GenBank rodent, mammalian, vertebrate, prokaryote, and eukaryote databases, SwissProt, BLOCKS, PRINTS, PFAM, and Prosite.

VI Chromosome Mapping

Radiation hybrid and genetic mapping data available from public resources such as the Stanford Human Genome Center (SHGC), Whitehead Institute for Genome Research (WIGR), and Généthon are used to determine if any of the cDNAs presented in the Sequence Listing have been mapped. Any fragment of a cDNA encoding a signal peptide-containing protein that has been mapped result in the assignment of all related fragments and regulatory sequences to the same location. The genetic map locations are described as ranges, or intervals, of human chromosomes. The map position of an interval, in cM (which is roughly equivalent to 1 megabase of human DNA), is measured relative to the terminus of the chromosomal p-arm.

VII Hybridization Technologies and Analyses

Immobilization of cDNAs on a Substrate

The cDNAs are applied to a substrate by one of the following methods. A mixture of cDNAs is fractionated by gel electrophoresis and transferred to a nylon membrane by capillary transfer. Alternatively, the cDNAs are individually ligated to a vector and inserted into bacterial host cells to form a library. The cDNAs are then arranged on a substrate by one of the following methods. In the first method, bacterial cells containing individual clones are robotically picked and arranged on a nylon membrane. The membrane is placed on LB agar containing selective agent (carbenicillin, kanamycin, ampicillin, or chloramphenicol depending on the vector used) and incubated at 37 C for 16 hr. The membrane is removed from the agar and consecutively placed colony side up in 10% SDS, denaturing solution (1.5 M NaCl, 0.5 M NaOH), neutralizing solution (1.5 M NaCl, 1 M Tris, pH 8.0), and twice in 2×SSC for 10 min each. The membrane is then UV irradiated in a STRATALINKER UV-crosslinker (Stratagene).

In the second method, cDNAs are amplified from bacterial vectors by thirty cycles of PCR using primers complementary to vector sequences flanking the insert. PCR amplification increases a starting concentration of 1-2 ng nucleic acid to a final quantity greater than 5 μg. Amplified nucleic acids from about 400 bp to about 5000 bp in length are purified using SEPHACRYL-400 beads (APB). Purified nucleic acids are arranged on a nylon membrane manually or using a dot/slot blotting manifold and suction device and are immobilized by denaturation, neutralization, and UV irradiation as described above. Purified nucleic acids are robotically arranged and immobilized on polymer-coated glass slides using the procedure described in U.S. Pat. No. 5,807, 522. Polymer-coated slides are prepared by cleaning glass microscope slides (Corning, Acton Mass.) by ultrasound in 0.1% SDS and acetone, etching in 4% hydrofluoric acid (VWR Scientific Products, West Chester Pa.), coating with 0.05% aminopropyl silane (Sigma Aldrich) in 95% ethanol, and curing in a 110 C oven. The slides are washed extensively with distilled water between and after treatments. The nucleic acids are arranged on the slide and then immobilized by exposing the array to UV irradiation using a STRATALINKER UV-crosslinker (Stratagene). Arrays are then washed at room temperature in 0.2% SDS and rinsed three times in distilled water. Non-specific binding sites are blocked by incubation of arrays in 0.2% casein in phosphate buffered saline (PBS; Tropix, Bedford Mass.) for 30 min at 60 C; then the arrays are washed in 0.2% SDS and rinsed in distilled water as before.

Probe Preparation for Membrane Hybridization

Hybridization probes derived from the cDNAs of the Sequence Listing are employed for screening cDNAs, mRNAs, or genomic DNA in membrane-based hybridizations. Probes are prepared by diluting the cDNAs to a concentration of 40-50 ng in 45 μl TE buffer, denaturing by heating to 100 C for five min, and briefly centrifuging. The denatured cDNA is then added to a REDIPRIME tube (APB), gently mixed until blue color is evenly distributed, and briefly centrifuged. Five μl of [$^{32}$P]dCTP is added to the tube, and the contents are incubated at 37 C for 10 min. The labeling reaction is stopped by adding 5 μl of 0.2 M EDTA, and probe is purified from unincorporated nucleotides using a PROBEQUANT G-50 microcolumn (APB). The purified probe is heated to 100 C for five min, snap cooled for two min on ice, and used in membrane-based hybridizations as described below.

Probe Preparation for Polymer Coated Slide Hybridization

Hybridization probes derived from mRNA isolated from samples are employed for screening cDNAs of the Sequence Listing in array-based hybridizations. Probe is prepared using the GEMbright kit (Incyte Genomics) by diluting mRNA to a concentration of 200 ng in 9 μl TE buffer and adding 5 μl 5× buffer, 1 μl 0.1 M DTT, 3 μl Cy3 or Cy5 labeling mix, 1 μl RNase inhibitor, 1 μl reverse transcriptase, and 5 μl 1× yeast control mRNAs. Yeast control mRNAs are synthesized by in vitro transcription from noncoding yeast genomic DNA (W. Lei, unpublished). As quantitative controls, one set of control mRNAs at 0.002 ng, 0.02 ng, 0.2 ng, and 2 ng are diluted into reverse transcription reaction mixture at ratios of 1:100,000, 1:10,000, 1:1000, and 1:100 (w/w) to sample mRNA respectively. To examine mRNA differential expression patterns, a second set of control mRNAs are diluted into reverse transcription reaction mixture at ratios of 1:3, 3:1, 1:10, 10:1, 1:25, and 25:1 (w/w). The reaction mixture is mixed and incubated at 37 C for two hr. The reaction mixture is then incubated for 20 min at 85 C, and probes are purified using two successive CHROMA SPIN+TE 30 columns (Clontech, Palo Alto Calif.). Purified probe is ethanol precipitated by diluting probe to 90 μl in DEPC-treated water, adding 2 μl 1 mg/ml glycogen, 60 μl 5 M sodium acetate, and 300 μl 100% ethanol. The probe is centrifuged for 20 min at 20,800×g, and the pellet is resuspended in 12 μl resuspension buffer, heated to 65 C for five min, and mixed thoroughly. The probe is heated and mixed as before and then stored on ice. Probe is used in high density array-based hybridizations as described below.

Membrane-based Hybridization

Membranes are pre-hybridized in hybridization solution containing 1% Sarkosyl and 1× high phosphate buffer (0.5 M NaCl, 0.1 M Na$_2$HPO$_4$, 5 mM EDTA, pH 7) at 55 C for two hr. The probe, diluted in 15 ml fresh hybridization solution, is then added to the membrane. The membrane is hybridized with the probe at 55 C for 16 hr. Following hybridization, the membrane is washed for 15 min at 25 C in 1 mM Tris (pH 8.0), 1% Sarkosyl, and four times for 15 min each at 25 C in 1 mM Tris (pH 8.0). To detect hybridization complexes, XOMAT-AR film (Eastman Kodak, Rochester N.Y.) is exposed to the membrane overnight at −70 C, developed, and examined visually.

Polymer Coated Slide-based Hybridization

Probe is heated to 65 C for five min, centrifuged five min at 9400 rpm in a 5415 C microcentrifuge (Eppendorf Scientific, Westbury N.Y.), and then 18 μl is aliquoted onto the array surface and covered with a coverslip. The arrays are transferred to a waterproof chamber having a cavity just slightly larger than a microscope slide. The chamber is kept at 100% humidity internally by the addition of 140 μl of 5×SSC in a corner of the chamber. The chamber containing the arrays is incubated for about 6.5 hr at 60 C. The arrays are washed for 10 min at 45 C in 1×SC, 0.1% SDS, and three times for 10 min each at 45 C in 0.1×SSC, and dried.

Hybridization reactions are performed in absolute or differential hybridization formats. In the absolute hybridization format, probe from one sample is hybridized to array elements, and signals are detected after hybridization complexes form. Signal strength correlates with probe mRNA levels in the sample. In the differential hybridization format, differential expression of a set of genes in two biological samples is analyzed. Probes from the two samples are prepared and labeled with different labeling moieties. A mixture of the two labeled probes is hybridized to the array elements, and signals are examined under conditions in which the emissions from the two different labels are individually detectable. Elements on the array that are hybridized to equal numbers of probes derived from both biological samples give a distinct combined fluorescence (Shalon WO95/35505).

Hybridization complexes are detected with a microscope equipped with an Innova 70 mixed gas 10 W laser (Coherent, Santa Clara Calif.) capable of generating spectral lines at 488 nm for excitation of Cy3 and at 632 nm for excitation of Cy5. The excitation laser light is focused on the array using a 20× microscope objective (Nikon, Melville N.Y.). The slide containing the array is placed on a computer-controlled X-Y stage on the microscope and raster-scanned past the objective with a resolution of 20 micrometers. In the differential hybridization format, the two fluorophores are sequentially excited by the laser. Emitted light is split, based on wavelength, into two photomultiplier tube detectors (PMT R1477, Hamamatsu Photonics Systems, Bridgewater N.J.) corresponding to the two fluorophores. Filters positioned between the array and the photomultiplier tubes are used to separate the signals. The emission maxima of the fluorophores used are 565 nm for Cy3 and 650 nm for Cy5. The sensitivity of the scans is calibrated using the signal intensity generated by the yeast control mRNAs added to the probe mix. A specific location on the array contains a complementary DNA sequence, allowing the intensity of the signal at that location to be correlated with a weight ratio of hybridizing species of 1:100,000.

The output of the photomultiplier tube is digitized using a 12-bit RTI-835H analog-to-digital (A/D) conversion board (Analog Devices, Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using the emission spectrum for each fluorophore. A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS program (Incyte Genomics).

VIII Transcript Imaging

A transcript image was performed using the LIFESEQ GOLD database (Jun01release, Incyte Genomics). This process allowed assessment of the relative abundance of the expressed polynucleotides in all of the cDNA libraries and reconfirmed the data submitted in U.S. Ser. No. 08/966,316, filed 7 Nov. 1997. Criteria for transcript imaging can be selected from category, number of cDNAs per library, library description, disease indication, clinical relevance of sample, and the like.

All sequences and cDNA libraries in the LIFESEQ database have been categorized by system, organ/tissue and cell type. For each category, the number of libraries in which the sequence was expressed were counted and shown over the total number of libraries in that category. In some transcript images, all normalized or pooled libraries, which have high copy number sequences removed prior to processing, and all mixed or pooled tissues, which are considered non-specific in that they contain more than one tissue type or more than one subject's tissue, can be excluded from the analysis. Treated and untreated cell lines and/or fetal tissue data can also be disregarded or removed where clinical relevance is emphasized. Conversely, fetal tissue may be emphasized wherever elucidation of inherited disorders or differentiation of particular cells or organs from stem cells (such as nerves, heart or kidney) would be furthered by removing clinical samples from the analysis. Transcript imaging can also be used to support data from other methodologies such as microarray analysis.

The transcript images for SEQ ID NOs:1-15 and 17 are shown below. The first column shows library name; the second column, the number of cDNAs sequenced in that library; the third column, the description of the library; the fourth column, absolute abundance of the transcript in the library; and the fifth column, percentage abundance of the transcript in the library.

| | | SEQ ID NO:1 Category: Nervous System (Brain) | | |
|---|---|---|---|---|
| Library | cDNAs | Description of Tissue | Abundance | % Abundance |
| HNT2AGT01 | 5225 | teratoCA line, hNT2, t/RA + MI | 1 | 0.0191 |
| BRAFDIT02 | 5908 | frontal lobe, Huntington's, 57M | 1 | 0.0169 |
| BRAINOM01 | 24452 | brain, infant, 10wF, NORM, WM | 1 | 0.0041 |

In clinically-relevant brain samples, SEQ ID NO:1 is expressed four-fold higher in Huntington's disease with its associated dementia than in normal brain. Even though this GPCR is very sparsely expressed in human tissues; when SEQ ID NO:1 is used in a brain tissue-specific assay, it is diagnostic for Huntington's disease.

| | | SEQ ID NO:2 Category: Digestive System (Stomach) | | |
|---|---|---|---|---|
| Library* | cDNAs | Description of Tissue | Abundance | % Abundance |
| STOMTUT01 | 2696 | stomach adenoCA, 52M, m/STOMNOT02 | 3 | 0.1113 |
| STOMTDE01 | 3971 | stomach, aw/esophagus adenoCA, 61M | 2 | 0.0504 |
| STOMNOT02 | 3156 | stomach, mw/adenoCA, 52M | 1 | 0.0317 |

*Libraries made from normalized and pooled tissues were removed from this analysis SEQ ID NO:2 was greater than two-fold differentially expressed in biopsied sample from the stomach of a subject diagnosed with adenocarcinoma over cytologically normal tissue from the same subject. Expression was not found in any other cytologically normal stomach tissue which included STOMNOT01, STOMNOT08, and STOMTMR02. SEQ ID NO:2, when used in a stomach-specific assay, is diagnostic for adenocarcinoma.

SEQ ID NO:3
Category: Exocrine Glands (Breast)

| Library* | cDNAs | Description of Tissue | Abundance | % Abundance |
|---|---|---|---|---|
| BRSTTUT16 | 3724 | ductal carcinoma, 43F, m/BRSTTMT01 | 2 | 0.0537 |
| BRSTNOR01 | 3107 | breast, mw/BRSTTUT22, lobular CA, 59F | | 0.0322 |
| BRSTTMT02 | 3240 | PF changes, mw/BRSTTUT16, 46F | 1 | 0.0309 |
| BRSTNOT09 | 3920 | PF changes, mw/BRSTTUT08 adenoCA, 45F | 1 | 0.0255 |

*Libraries made from normalized and pooled tissues were removed from this analysis SEQ ID NO:3 is differentially expressed in ductal carcinoma of the breast as compared with its matched cytologically normal BRSTTMT01. In addition, SEQ ID NO:3 was not expressed in BRSTNOT25 and BRSTNOT35, normal breast tissues removed during breast reduction surgeries, and was not as highly expressed in tissues diagnosed with any other disease states or their cytologically normal matched tissues. SEQ ID NO:3, when used in a breast-specific assay including, but not limited to, ductal lavage, is diagnostic for ductal carcinoma.

SEQ ID NO:4
Category: Female Reproductive (Uterus)

| Library | cDNAs | Description of Tissue | Abundance | % Abundance |
|---|---|---|---|---|
| UTRSTUC01 | 1175 | uterus adenosquamousCA, F, pool | 2 | 0.1702 |
| UTRENOT09 | 2791 | uterus, endometrium, aw/cystocele, 38F | 1 | 0.0358 |
| UTRSNOT05 | 6678 | uterus, mw/leiomyoma, 45F | 1 | 0.0150 |
| UTRSTUP05 | 16785 | uterus serous papillary CA, F, pool | 2 | 0.0119 |
| UTRSTUP02 | 22349 | uterus endometrial adenoCA, F, pool | 2 | 0.0089 |

SEQ ID NO:4 is more than five-fold differentially expressed in adenosquamous carcinoma of the uterus. It was not differentially expressed in tissues from subjects diagnosed with cervicitis (UTRCNOP01, UTRCDIE01), endometriosis (UTREDIT07, UTREDIT14), cervical tumor (UTRCTUP01), endometrial adenocarcinoma (UTRSTUP03, UTRSTUP04, UTRSTUP07), or leiomyoma (UTRSTUE01, UTRSTUT04, UTRSTUT05, UTRSTUT07) or in cytologically normal tissues (UTRCNOP01, UTREDME05, UTREDME06, UTREDMF01, UTREDMF02, UTREDMT07, UTRENON03, UTRENOT10, UTRETMC01, UTRETUP01, UTRMTMR02, UTRMTMT01, UTRPNOM01, UTRSNON03, UTRSNOP01, UTRSNOR01, UTRSNOT01, UTRSNOT02, UTRSNOT06, UTRSNOT08, UTRSNOT10, UTRSNOT11, UTRSNOT12, UTRSNOT16, UTRSNOT18, UTRSTDT01, UTRSTMC01, UTRSTME01, UTRSTMR01, and UTRSTMR02). SEQ ID NO:4, when used in a uterus-specific assay, is diagnostic for adenosquamous carcinoma.

SEQ ID NO:5
Category: Exocrine Glands (Breast)

| Library* | cDNAs | Description of Tissue | Abundance | % Abundance |
|---|---|---|---|---|
| BRSTTUT13 | 7631 | breast adenoCA, 46F, m/BRSTNOT33 | 58 | 0.7601 |
| BRSTNOT31 | 3102 | breast, mw/ductal adenoCA, 57F | 11 | 0.3546 |
| BRSTNOT32 | 3766 | nonfibrocyctic breast disease, 46F | 13 | 0.345 |

*Libraries made from normalized or pooled tissues and those containing less than 3000 cDNAs were removed from this analysis.

SEQ ID NO:5 is differentially expressed more than two-fold in adenocarcinoma of the breast when compared to expression in cytologically normal BRSTNOT31, BRSTNOT32 and matched BRSTNOT33. SEQ ID NO:5 was not differentially expressed in BRSTNOT25 and BRSTNOT35, normal breast tissues removed during breast reduction surgeries, and was not as highly expressed in tissues diagnosed with any other disease states or their cytologically normal matched tissues. SEQ ID NO:5, when used in a breast-specific assay including, but not limited to, ductal lavage, is diagnostic for adenocarcinoma.

SEQ ID NO:6
Category: Female Reproductive (Ovary)

| Library* | cDNAs | Description of Tissue | Abundance | % Abundance |
|---|---|---|---|---|
| OVARTUT02 | 3532 | ovary tumor, mucinous cystadenoma, 51F | 2 | 0.0566 |
| OVARNOT07 | 3663 | ovary, mw/follicular cysts, 28F | 1 | 0.0273 |
| OVARNOT13 | 3868 | ovary, aw/ leiomyoma, 47F | 1 | 0.0259 |
| OVARTUT07 | 4386 | ovary tumor, adenoCA, 58F | 1 | 0.0228 |
| OVARNOT02 | 8870 | ovary, aw/cardiomyopathy, 59F | 1 | 0.0113 |

*Libraries made from normalized or pooled tissues were removed from this analysis.

SEQ ID NO:6 is differentially expressed more than two-fold in mucinous cystadenoma of the ovary when compared to expression in cytologically normal OVARNOT07, OVARNOT13, and OVARNOT02 and in ovary tissue from a subject diagnosed with adenocarcinoma. SEQ ID NO:6 when used in a ovary-specific assay, is diagnostic for mucinous cystadenoma.

SEQ ID NO:7
Category: Musculoskeletal System (Cartilage, Synovium)

| Library | cDNAs | Description of Tissue | Abundance | % Abundance |
|---|---|---|---|---|
| CARCTXT02 | 3594 | knee chondrocytes, M/F, t/IL-1 | 4 | 0.1113 |
| SYNOOAT01 | 5674 | synovium, knee, OA, 82F | 5 | 0.0881 |
| SYNONOT01 | 4046 | synovium, 75M* | 3 | 0.0741 |
| SYNORAT03 | 5785 | synovium, wrist, rheuA, 56F | 4 | 0.0691 |
| SYNORAT05 | 3466 | synovium, knee, rheuA, 62F | 2 | 0.0577 |
| SYNORAT04 | 5636 | synovium, wrist, rheuA, 62F | 3 | 0.0532 |
| CARGDIT02 | 3440 | cartilage, OA, M/F | 1 | 0.0291 |
| CARGDIT01 | 7229 | cartilage, OA | 2 | 0.0277 |
| SYNORAB01 | 5053 | synovium, hip, rheuA, 68F | 1 | 0.0198 |

*insufficient clinical data to rule out that this individual did not have some age-related arthritis.

SEQ ID NO:7 is preferentially expressed in IL-1 treated chrondrocytes cultured from knee cartilage, in cartilage and synovia from subjects with rheumatoid and osteoarthritis. It was not expressed in normal control CARGNOT01. SEQ ID NO:7, when used in a tissue-specific assay, is diagnostic for arthritis.

SEQ ID NO:8
Category: Male Reproductive (Testes)

| Library | cDNAs | Description of Tissue | Abundance | % Abundance |
|---|---|---|---|---|
| TESTTUT03 | 3812 | testicular seminoma, 45M | 2 | 0.0525 |

SEQ ID NO:8 was significantly expressed in testicular seminoma; it was not expressed in normal tissue from TESTNOC01, TESTNOF01, TESTNOM01, TESTNON04, TESTNOP01, TESTNOT01, TESTNOT03, TESTNOT04, TESTNOT07, TESTNOT10, and TESTNOT11, or in embryonal carcinomas from TESTTUE02 and TESTTUT02. SEQ ID NO:7, when used in a clinically relevant, testicle-specific assay, is a diagnostic for testicular seminoma.

SEQ ID NO:9
Category: Male Reproductive (Prostate)

| Library | cDNAs | Description of Tissue | Abundance | % Abundance |
|---|---|---|---|---|
| PROSTMT05 | 3234 | AH, mw/PROSTUT16 adenoCA, 55M | 2 | 0.0618 |
| PROSNOT19 | 3678 | AH, mw/PROSTUT13 adenoCA, M | 2 | 0.0544 |
| PROSNOT07 | 3046 | AH, mw/PROSTUT05 adenoCA, 69M | 1 | 0.0328 |
| PROSTMT07 | 3104 | AH, mw/adenoCA, 73M | 1 | 0.0322 |
| PROSDIN01 | 3421 | AH, mw/PROSTUT10 adenoCA, 66M, NORM | 1 | 0.0292 |
| PROSNOT28 | 3814 | AH, mw/PROSTUT16 adenoCA, 55M | 1 | 0.0262 |
| PROSNOT15 | 4133 | AH, mw/PROSTUT10 adenoCA, 66M | 1 | 0.0242 |
| PROSTMY01 | 6460 | AH, mw/PROSTUT16 adenoCA, 55M | 1 | 0.0155 |
| PROSBPT02 | 6583 | AH, mw/adenoCA, 65M | 1 | 0.0152 |

*Libraries made from subtracted or pooled tissues were removed from this analysis.

SEQ ID NO:9 was specifically expressed in prostate tissue cytologically showing adenofibromatous hyperplasia and matched with adenocarcinoma of the prostate (see PROSTUT matches above). It was not expressed in tissues from subjects diagnosed with benign prostatic hyperplasia (PROSBPS05, PROSBPT03, PROSDIP01, PROSDIP02, and PROSDIP03), or prostatic IN (PROETMP06, PROETMP07). SEQ ID NO:9, when used in a prostate-specific assay, is diagnostic for AH and may serve as an early diagnostic marker for prostatic adenocarcinoma.

SEQ ID NO:10
Category: Urinary Tract (Bladder)

| Library* | cDNAs | Description of Tissue | Abundance | % Abundance |
|---|---|---|---|---|
| BLADNOT05 | 3774 | bladder, mw/BLADTUT04 TC CA in situ, 60M | 4 | 0.1060 |
| BLADDIT01 | 3775 | bladder, chronic cystitis, 73M | 1 | 0.0265 |

*Libraries made from normalized tissues were removed from this analysis.

SEQ ID NO:10 showed five-fold differential expression in a cytologically normal bladder library which was matched with transitional cell carcinoma of the bladder. Expression of SEQ ID NO:10 was clearly distinct from that seen in tissue affected by chronic cystitis and was not seen in normal tissues, BLADNOR01, BLADNOT01, BLADNOT03, BLADNOT04, BLADNOT06, and BLADNOT08 or in the tumor libraries, BLADTUE01, BLADTUT02, BLADTUT03, BLADTUT04, BLADTUT05, BLADTUT06, BLADTUT07 and BLADTUT08. SEQ ID NO:10, when used in a bladder-specific assay, serves as an early diagnostic marker for transitional cell carcinoma of the bladder.

SEQ ID NO:11
Category: Urinary Tract (Kidney)

| Library* | cDNAs | Description of Tissue | Abundance | % Abundance |
|---|---|---|---|---|
| KIDNTUT13 | 3771 | renal cell CA, 51F | 2 | 0.0530 |
| KIDNTUT15 | 3941 | renal cell CA, 65M m/KIDNNOT19 | 2 | 0.0507 |
| KIDNNOT19 | 6952 | mw/KIDNTUT15 renal cell CA, 65M | 2 | 0.0288 |
| KIDNTUT14 | 3861 | renal cell CA, 43M, m/KIDNNOT20 | 1 | 0.0259 |

*Libraries made from normalized, subtracted, and pooled tissues were removed from this analysis.

SEQ ID NO:11 is expressed in renal cell cancers and not expressed in cytologically normal kidney libraries (KIDNNOT01, KIDNNOT02, KIDNNOT20, KIDNNOT25, KIDNNOT26, KIDNNOT31, KIDNNOT32) or in KIDPTDE01 from a subject diagnosed with interstitial nephritis. SEQ ID NO:10, when used in a kidney-specific assay, serves as a diagnostic for renal cell cancer.

SEQ ID NO:12
Category: Exocrine Glands (Breast)

| Library* | cDNAs | Description of Tissue | Abundance | % Abundance |
|---|---|---|---|---|
| BRSTTUT15 | 6535 | adenocarcinoma, 46F, m/BRSTNOT17 | 2 | 0.0306 |

SEQ ID NO:12 is expressed in adenocarcinoma of the breast and not expressed in cytologically normal matched tissue. SEQ ID NO:12, when used in a breast-specific assay including, but not limited to, ductal lavage, serves as a diagnostic for adenocarcinoma of the breast.

SEQ ID NO:13
Category: Endocrine Glands (Pituitary Gland)

| Library* | cDNAs | Description of Tissue | Abundance | % Abundance |
|---|---|---|---|---|
| PITUNOT06 | 6165 | pituitary aw/ schizophrenia, COPD, 55M | 808 | 13.1062 |
| PITUNOT02 | 226 | pituitary, 15-75M/F, pool | 4 | 1.7699 |
| PITUNOT01 | 8390 | pituitary, 16-70M/F, pool | 87 | 1.0369 |
| PTTUNOT03 | 2857 | pituitary aw/ colon cancer, 46M | 15 | 0.5250 |
| PITUDIR01 | 5981 | pituitary aw/ AD, mets adenoCA, 70F | 14 | 0.2341 |

*Libraries made from normalized tissues were removed from this analysis.

SEQ ID NO:13 is highly overexpressed in the pituitary gland removed from a schizophenic subject with chronic pulmonary pulmonary disease. Such high expression levels were not seen in pooled normal tissue or in the pituitaries of subjects with cancers and Alzheimer's disease (AD). SEQ ID NO:13, when used in a tissue-specific assay, serves as a diagnostic for schizophrenia.

SEQ ID NO:14
Category: Exocrine Glands (Breast)

| Library* | cDNAs | Description of Tissue | Abundance | % Abundance |
|---|---|---|---|---|
| BRSTTUT22 | 3774 | lobular CA, 59F, in/BRSTNOT16 | 2 | 0.0530 |
| BRSTNOT31 | 3102 | mw/ductal adenoCA, 57F | 1 | 0.0322 |
| BRSTDIT01 | 3394 | PF changes, mw/ intraductal cancer, 48F | 1 | 0.0295 |
| BRSTNOT28 | 3734 | PF changes, 40F | 1 | 0.0268 |
| BRSTNOT09 | 3920 | PF changes, mw/ BRSTTUT08 adenoCA, 45F | 1 | 0.0255 |
| BRSTNOT19 | 4019 | mw/lobular CA, 67F | 1 | 0.0249 |
| BRSTNOT23 | 4056 | NF breast disease, 35F | 1 | 0.0247 |
| BRSTNOT03 | 6777 | PF changes, mw/ BRSTTUT02 adenoCA, 54F | 1 | 0.0148 |
| BRSTNOT02 | 9077 | PF changes, mw/ BRSTTUT01 adenoCA, 55F | 1 | 0.0110 |
| BRSTNOT07 | 10055 | PF changes, mw/ intraductal adenoCA, 43F | 1 | 0.0099 |

*Libraries made from normalized tissues were removed from this analysis.

SEQ ID NO:14 is differentially expressed in breast cancer, in particular, in lobular carcinoma. When used in a breast-specific assay including, but not limited to, ductal lavage, SEQ ID NO:14 serves as a diagnostic for breast cancer.

SEQ ID NO:15
Category: Hemic Immune (Peripheral blood)

| Library* | cDNAs | Description of Tissue | Abundance | % Abundance |
|---|---|---|---|---|
| EOSINOT02 | 2356 | eosinophils, asthma, M/F | 5 | 0.2122 |
| MPHGNOT03 | 7791 | macrophages, M/F | 4 | 0.0513 |
| EOSINOT01 | 2404 | eosinophils, nonallergic, M/F | 1 | 0.0416 |

*Libraries made from treated cell lines were removed from this analysis.

SEQ ID NO:15 is 4-fold differentially expressed in peripheral blood, particularly eosinophils of asthmatics. When used in an assay of a lung sample, SEQ ID NO:15 is a diagnostic for asthma.

SEQ ID NO:17
Category: Exocrine Glands (Breast)

| Library* | cDNAs | Description of Tissue | Abundance | % Abundance |
|---|---|---|---|---|
| BRSTTUT14 | 3951 | breast adenoCA, 62F, m/ | 1 | 0.0253 |
| BRSTNOT14 | | | | |

The transcript image confirms the information obtained in the original northern analysis (7 Nov. 1997). SEQ ID NO:17 is expressed in adenocarcinoma of the breast and not expressed in cytologically normal matched tissue, BRST-NOT14. Expression was absent from BRSTNOT25 and BRSTNOT35, normal breast tissues removed during breast reduction surgeries. When used in a breast-specific assay, including, but not limited to, ductal lavage, and compared with cancerous and normal standards, expression of SEQ ID NO:17 is diagnostic for breast adenocarcinoma.

In assays using normal and cancerous standards and patient samples, the cDNA, an mRNA, or an antibody specifically binding the protein can serve a clinically relevant diagnostic marker for disorders associated with cell proliferation and cell signaling.

IX Northern Analyses

SEQ ID NOs:1-15 and 17 were compared with all the other sequences in the LIFESEQ database (Incyte Genomics, Palo Alto Calif.) using BLAST analysis (Altschul (1993) supra); Altschul(1990) supra). The results of the BLAST analyses were reported in THE INVENTION section above.

Each of the Incyte clones is also used to screen northern blots. A probe is generated by EcoRI digestion of the plasmid containing the cDNA. The restriction digest is fractionated on a 1% agarose gel, a restriction fragment from about 400 to about 1400 nt in length is excised from the gel and purified on a QIAQUICK column (Qiagen). The fragment is comprised of the 5' most region of the insert. The probe is prepared by random priming using the REDIPRIME labeling kit (APB) with REDIVUE [-$^{32}$P]d-CTP (3000 Ci/mmol; APB). Unincorporated radioactivity is removed by column chromatography using a SEPHADEX G-50 NICK column (APB).

Each commercial MTN blot (Clontech) contained approximately 2 ug of poly A+ per lane from various tissues. Otherwise, RNA was electrophoresed on a denaturing formaldehyde, 1.2% agarose gel, blotted on a nylon membrane, and fixed by UV irradiation.

Blots are pre-hybridized in RAPID-HYB hybridization buffer (APB) for 1 hour at 65 C. Hybridizations are performed at 65 C using 0.5×10 cpm/ml probe for 1 hour. Blots are washed for 2×10 minutes in 1×SSC, 0.1% SDS at room temperature followed by 2 stringent washes at 65 C in 0.2×SSC, 0.1% SDS for 10 minutes each. Blots are wrapped in SARAN WRAP plastic film (Dow Chemical, Midland Mich.) and autoradiographed at −70 C using 2 intensifying screens and HYPERFILM-MP (APB).

The northern analysis for SEQ ID NO:17, Incyte clone 2547002, performed Wednesday, 5 Nov. 1997 showed expression in the following libraries of the LIFESEQ database (Incyte Genomics).

| Library | Description |
|---|---|
| HEARNOT06 | heart, 44M |
| HEAPNOT01 | heart, coronary artery, plaque, pool |
| SMCANOT01 | smooth muscle cell line, aorta, M |
| BRSTTUT14 | breast tumor, adenocarcinoma, 62F, mw/ BRSTNOT14 |
| UTRSNOT16 | uterus, endometrium, 48F |
| UTRSNOT11 | uterus, myometrium, 43F |
| UTRSNOT02 | uterus, 34F |
| LPARNOT02 | parotid gland, 70M |

When used in a breast sample specific assay and compared with cancerous and normal standards, SEQ ID NO:17 is diagnostic for breast adenocarcinoma (bold above)

X Complementary Molecules

Molecules complementary to the cDNA, from about 5 (PNA) to about 5000 bp (complement of a cDNA insert), are used to detect or inhibit gene expression. Detection is described in Example VII. To inhibit transcription by preventing promoter binding, the complementary molecule is designed to bind to the most unique 5' sequence and includes nucleotides of the 5' UTR upstream of the initiation codon of the open reading frame. Complementary molecules include genomic sequences (such as enhancers or introns) and are used in "triple helix" base pairing to compromise the ability of the double helix to open sufficiently for the binding of polymerases, transcription factors, or regulatory molecules. To inhibit translation, a complementary molecule is designed to prevent ribosomal binding to the mRNA encoding the protein.

Complementary molecules are placed in expression vectors and used to transform a cell line to test efficacy; into an organ, tumor, synovial cavity, or the vascular system for transient or short term therapy; or into a stem cell, zygote, or other reproducing lineage for long term or stable gene therapy. Transient expression lasts for a month or more with a non-replicating vector and for three months or more if elements for inducing vector replication are used in the transformation/expression system.

Stable transformation of dividing cells with a vector encoding the complementary molecule produces a transgenic cell line, tissue, or organism (U.S. Pat. No. 4,736,866). Those cells that assimilate and replicate sufficient quantities of the vector to allow stable integration also produce enough complementary molecules to compromise or entirely eliminate activity of the cDNA encoding the protein.

XI Protein Expression

Expression and purification of the protein are achieved using either a mammalian or an insect cell expression system. The pUB6/V5-His vector system (Invitrogen, Carlsbad Calif.) is used to express signal peptide-containing proteins in CHO cells. The vector contains the selectable bsd gene, multiple cloning sites, the promoter/enhancer sequence from the human ubiquitin C gene, a C-terminal V5 epitope for antibody detection with anti-V5 antibodies, and a C-terminal polyhistidine (6×His) sequence for rapid purification on PROBOND resin (Invitrogen). Transformed cells are selected on media containing blasticidin.

*Spodoptera frugiperda* (Sf9) insect cells are infected with recombinant *Autographica californica* nuclear polyhedrosis virus (baculovirus). The polyhedrin gene is replaced with the cDNA by homologous recombination and the polyhedrin promoter drives cDNA transcription. The protein is synthesized as a fusion protein with 6×his which enables purification as described above. Purified protein is used in the following activity and to make antibodies.

XII Production of Antibodies

A signal peptide-containing protein is purified using polyacrylamide gel electrophoresis and used to immunize mice or rabbits. Antibodies are produced using the protocols well known in the art and summarized below. Alternatively, the amino acid sequence of signal peptide-containing proteins is analyzed using LASERGENE software (DNASTAR) to determine regions of high antigenicity. An antigenic epitope, usually found near the C-terminus or in a hydrophilic region is selected, synthesized, and used to raise antibodies. Typically, epitopes of about 15 residues in length are produced using an 431 A peptide synthesizer (ABI) using Fmoc-chemistry and coupled to KLH (Sigma-Aldrich) by reaction with N-maleimidobenzoyl-N-hydroxysuccinimide ester to increase antigenicity.

Rabbits are immunized with the epitope-KLH complex in complete Freund's adjuvant. Immunizations are repeated at intervals thereafter in incomplete Freund's adjuvant. After a minimum of seven weeks for mouse or twelve weeks for rabbit, antisera are drawn and tested for antipeptide activity.

Testing involves binding the peptide to plastic, blocking with 1% bovine serum albumin, reacting with rabbit antisera, washing, and reacting with radio-iodinated goat anti-rabbit IgG. Methods well known in the art are used to determine antibody titer and the amount of complex formation.

XIII Purification of Naturally Occurring Protein Using Specific Antibodies

Naturally occurring or recombinant protein is purified by immunoaffinity chromatography using antibodies which specifically bind the protein. An immunoaffinity column is constructed by covalently coupling the antibody to CNBr-activated SEPHAROSE resin (APB). Media containing the protein is passed over the immunoaffinity column, and the column is washed using high ionic strength buffers in the presence of detergent to allow preferential absorbance of the protein. After coupling, the protein is eluted from the column using a buffer of pH 2-3 or a high concentration of urea or thiocyanate ion to disrupt antibody/protein binding, and the protein is collected.

XIV Screening Molecules for Specific Binding with the cDNA or Protein

The cDNA, or fragments thereof, or the protein, or portions thereof, are labeled with $^{32}$P-dCTP, Cy3-dCTP, or Cy5-dCTP (APB), or with BIODIPY or FITC (Molecular Probes, Eugene Oreg.), respectively. Libraries of candidate molecules or compounds previously arranged on a substrate are incubated in the presence of labeled cDNA or protein. After incubation under conditions for either a nucleic acid or amino acid sequence, the substrate is washed, and any position on the substrate retaining label, which indicates specific binding or complex formation, is assayed, and the ligand is identified. Data obtained using different concentrations of the nucleic acid or protein are used to calculate affinity between the labeled nucleic acid or protein and the bound molecule.

XV Two-Hybrid Screen

A yeast two-hybrid system, MATCHMAKER LexA Two-Hybrid system (Clontech Laboratories, Palo Alto Calif.), is used to screen for peptides that bind the protein of the invention. A cDNA encoding the protein is inserted into the multiple cloning site of a pLexA vector, ligated, and transformed into E. coli. cDNA, prepared from mRNA, is inserted into the multiple cloning site of a pB42AD vector, ligated, and transformed into E. coli to construct a cDNA library. The pLexA plasmid and pB42AD-cDNA library constructs are isolated from E. coli and used in a 2:1 ratio to co-transform competent yeast EGY48[p8op-lacZ] cells using a polyethylene glycol/lithium acetate protocol. Transformed yeast cells are plated on synthetic dropout (SD) media lacking histidine (-His), tryptophan (-Trp), and uracil (-Ura), and incubated at 30 C until the colonies have grown up and are counted. The colonies are pooled in a minimal volume of 1×TE (pH 7.5), replated on SD/-His/-Leu/-Trp/-Ura media supplemented with 2% galactose (Gal), 1% raffinose (Raf), and 80 mg/ml 5-bromo-4-chloro-3-indolyl β-d-galactopyranoside (X-Gal), and subsequently examined for growth of blue colonies. Interaction between expressed protein and cDNA fusion proteins activates expression of a LEU2 reporter gene in EGY48 and produces colony growth on media lacking leucine (-Leu). Interaction also activates expression of β-galactosidase from the p8op-lacZ reporter construct that produces blue color in colonies grown on X-Gal.

Positive interactions between expressed protein and cDNA fusion proteins are verified by isolating individual positive colonies and growing them in SD/-Trp/-Ura liquid medium for 1 to 2 days at 30 C. A sample of the culture is plated on SD/-Trp/-Ura media and incubated at 30 C until colonies appear. The sample is replica-plated on SD/-Trp/-Ura and SD/-His/-Trp/-Ura plates. Colonies that grow on SD containing histidine but not on media lacking histidine have lost the pLexA plasmid. Histidine-requiring colonies are grown on SD/Gal/Raf/X-Gal/-Trp/-Ura, and white colonies are isolated and propagated. The pB42AD-cDNA plasmid, which contains a cDNA encoding a protein that physically interacts with the protein, is isolated from the yeast cells and characterized.

XVI Demonstration of Protein Activity

Cell Proliferation

SP can be expressed in a mammalian cell line such as DLD-1 or HCT116 (ATCC; Manassas Va.) by transforming the cells with a eukaryotic expression vector encoding SP. Other eukaryotic expression vectors, such as those mentioned in EXAMPLE XI above, are commercially available, and the techniques to introduce them into cells are well known to those skilled in the art. The effect of SP on cell morphology can be visualized by microscopy; the effect on cell growth can be determined by measuring cell doubling-time; and the effect on tumorigenicity can be assessed by the ability of transformed cells to grow in a soft agar growth assay (Groden et al., (1995) Cancer Res. 55:1531-1539).

Receptor SPs such as those encoded by SEQ ID NOs:17, 15, 12, 6, and 1 can be expressed in heterologous expression systems and their biological activity tested utilizing the purinergic receptor system ($P_{2U}$) as published by Erb et al. (1993; Proc Natl Acad Sci 90:10449-53). Because cultured K562 human leukemia cells lack $P_{2U}$ receptors, they can be transfected with expression vectors containing either normal or chimeric $P_{2U}$ and loaded with fura-a, fluorescent probe for $Ca^{++}$. Activation of properly assembled and functional extracellular SP-transmembrane/intracellular $P_{2U}$ receptors with extracellular UTP or ATP mobilizes intracellular $Ca^{++}$ which reacts with fura-a and is measured spectrofluorometrically. Bathing the transfected K562 cells in microwells containing appropriate ligands will trigger binding and fluorescent activity identifying effectors of SP. The $P_{2U}$ system is also useful for identifying antagonists or inhibitors which block binding and prevent such fluorescent reactions.

All patents and publications mentioned in the specification are incorporated by reference herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of molecular biology or related fields are intended to be within the scope of the following claims.

TABLE 1

| SEQUENCES | DESIGNATION | INCYTE CLONE | LIBRARY | HOMOLOG | GENBANK DESCRIPTOR |
|---|---|---|---|---|---|
| SEQ ID NO:1 | SP-1 | 1221102 | NEUTGMT01 | g1575512 | GPR19 gene |
| SEQ ID NO:2 | SP-2 | 1457779 | COLNFET02 | g1842120 | ATP diphosphohydrolase |
| SEQ ID NO:3 | SP-3 | 1682433 | PROSNOT15 | g1070391 | transmembrane protein |
| SEQ ID NO:4 | SP-4 | 1899132 | BLADTUT06 | g887602 | Saccharomyces cerevisiae protein |
| SEQ ID NO:5 | SP-5 | 1907344 | CONNTUT01 | g33715 | immunoglobulin light chain |
| SEQ ID NO:6 | SP-6 | 1963651 | BRSTNOT04 | g1657623 | orphan receptor RDC1 |
| SEQ ID NO:7 | SP-7 | 1976095 | PANCTUT02 | g2117185 | Mycobacterium tuberculosis protein |
| SEQ ID NO:8 | SP-8 | 2417676 | HNT3AZT01 | g2150012 | human transmembrane protein |
| SEQ ID NO:9 | SP-9 | 1805538 | SINTNOT13 | g294502 | extracellular matrix protein |
| SEQ ID NO:10 | SP-10 | 1869688 | SKINBIT01 | g1562 | G3 serine/threonine kinase |
| SEQ ID NO:11 | SP-11 | 1880692 | LEUKNOT03 | g1487910 | Caenorhabditis elegans protein |
| SEQ ID NO:12 | SP-12 | 318060 | EOSIHET02 | g606788 | opioid receptor |
| SEQ ID NO:13 | SP-13 | 396450 | PITUNOT02 | g342279 | opiomelanocortin |
| SEQ ID NO:14 | SP-14 | 506333 | TMLR3DT02 | g2204110 | adenylyl cyclase type VII |
| SEQ ID NO:15 | SP-15 | 764465 | LUNGNOT04 | g1902984 | lectin-like oxidized LDL receptor |
| SEQ ID NO:16 | SP-16 | 2547007 | UTRSNOT11 | g399711 | bovine GPCR |
| SEQ ID NO:17 | | 2547007 | UTRSNOT11 | | |

What is claimed is:

1. A purified protein comprising the amino acid sequence of SEQ ID NO:16.

2. A purified protein of claim 1 consisting of the amino acid sequence of SEQ ID NO:16.

3. A composition comprising a protein of claim 1 and a labeling moiety or a pharmaceutical carrier.

* * * * *

```
                          SEQUENCE LISTING

<160> NUMBER OF SEQ ID NOS: 79

<210> SEQ ID NO 1
<211> LENGTH: 619
<212> TYPE: DNA
<213> ORGANISM: Homo sapiens
<220> FEATURE:
<221> NAME/KEY: misc_feature
<223> OTHER INFORMATION: Incyte ID No: 1221102

<400> SEQUENCE: 1
ggacaatgaa cattgtccct cggacaaaag tgaaaactat caagatgttc ctcattttaa    60
    atctgttgtt tttgctctcc tggctgcctt ttcatgtagc tcagctatgg cacccccatg   120
    aacaagacta taagaaaagt tcccttgttt tcacagctat cacatggata tcctttagtt   180
    cttcagcctc taaacctact ctgtattcaa tttataatgc caatttcgga gagggatgaa   240
    agagacttttt tgcatgtcct ctatgaaatg ttaccgaagc aatgcctata ctatcacaac   300
    aagttcaagg atggccaaaa aaaactacgt tggcatttca gaaatcccctt ccatggccaa   360
    aactattacc caaagactcg atctatgact catttgacag agaagccaag gaaaaaaagc   420
    ttgcttggcc cattaactca aatccaccaa atacttttgt ccaagttctc attctttcaa   480
    ttgttatgca ccagagatta aaaagcttta actataaaaa cagaagctat ttacatattt   540
    gttttcactc aactttccaa gggaaatgtt ttattttgta aaatgcattc atttgtttac   600
    tgtaaaaaaa aaaaaaaaa                                                619

<210> SEQ ID NO 2
<211> LENGTH: 742
<212> TYPE: DNA
<213> ORGANISM: Homo sapiens
<220> FEATURE:
<221> NAME/KEY: misc_feature
<223> OTHER INFORMATION: Incyte ID No: 1457779

<400> SEQUENCE: 2
cctggagcca ggtgcacagc gcatcgcccg aggctgtcac cgccctgccc cgcccacccc    60
    agctgtcctg gacccagggg cagggagagg ctggacgcca ggtgcgcgga cacagaagcg   120
    tctaagcaca gcttcctcct tgccgctccg ggaagtgggc agccagccca ggaaccagta   180
    ccacctgcac catgggggctg tcccggaagg agcaggtctt cttggccctg ctggggggcct   240
    cgggggtctc aggcctcacg gcactcattc tcctcctggt ggaggccacc agcgtgctcc   300
    tgcccacaga catcaagttt gggatcgtgt ttgatgcggg ctcctcccac acgtccctct   360
    tcctgtatca gtggccggcg aacaaggaga atggcacggg tgtggtcagc caggccctgg   420
    cctgccaggt ggaagggcct ggaatctcct cctacacttc taatgctgca caggctggtg   480
    agagcctgca gggctgcttg gaggaggcgc tggtgctgat cccagaggcc cagcatcgga   540
    aaacacccac gttcctgggg gccacggctg gcatgaggtt gctcagccgg aagaacagct   600
    ctcagggcca gggacatctt tgcagcagtc acccaggtcc tggggccggt ctcccgtgga   660
    cttttggggt gccgagctcc tggccgggca ggccgaagtg gcctttggtt ggatcactgt   720
    caactacggc ttggggacgt tt                                             742

<210> SEQ ID NO 3
```

<211> LENGTH: 1141
<212> TYPE: DNA
<213> ORGANISM: Homo sapiens
<220> FEATURE:
<221> NAME/KEY: misc_feature
<223> OTHER INFORMATION: Incyte ID No: 1682433

<400> SEQUENCE: 3

```
cgctgaaacc ctgggcggcg gcaagctgtg cgacctcttc tgcggccggc ctgggcaggt   60
gtcttcctcg agaggcaggc agggatccc ggacccttat acaggatgct gtgttctttg  120
ctcctttgtg aatgtctgtt gctggtagct ggttatgctc atgatgatga ctggattgac  180
cccacagaca tgcttaacta tgatgctgct tcaggaacaa tgagaaaatc tcaggcaaaa  240
tatggtattt caggggaaaa ggatgtcagt cctgactgt catgtgctga tgaaatatca  300
gaatgttatc acaaacttga ttctttaact tataagattg atgagtgtga aagaaaaag  360
agggaagact atgaaagtca aagcaatcct gttttaagga gatacttaaa taagatttta  420
attgaagctg gaaagcttgg acttcctgat gaaaacaaag gcgatatgca ttatgatgct  480
gagattatcc ttaaaagaga aactttgtta gaaatacaga gtttctcaa tggagaagac  540
tggaaaccag gtgccttgga tgatgcacta agtgatattt taattaattt taagtttcat  600
gattttgaaa catggaagtg gcgattcgaa gattcctttg gagtggatcc atataatgtg  660
ttaatggtac ttctttgtct gctctgcatc gtggttttag tggctaccga gctgtggaca  720
tatgtacgtt ggtacactca gttgagacgt gtttaatca tcagcttct gttcagtttg  780
ggatggaatt ggatgtattt atataagcta gcttttgcac agcatcaggc tgaagtcgcc  840
aagatggagc cattaaacaa tgtgtgtgcc aaaaagatgg actgactgg aagtatctgg  900
gaatggttta gaagttcatg gacctataag gatgacccat gccaaaaata ctatgagctc  960
ttactagtca accctatttg gttggtccca ccaacaaagg cacttgcagt tacattcacc 1020
acatttgtaa cggagccatt gaagcatatt ggaaaaggaa ctggggaatt tattaaagca 1080
ctcatgaagg aaattccagc gctgcttcat cttccagtgc tgataattat ggcattagcc 1140
a                                                                1141
```

<210> SEQ ID NO 4
<211> LENGTH: 898
<212> TYPE: DNA
<213> ORGANISM: Homo sapiens
<220> FEATURE:
<221> NAME/KEY: misc_feature
<223> OTHER INFORMATION: Incyte ID No: 1899132

<400> SEQUENCE: 4

```
tgcgaacctg gcccgtgcgg aaagggcgcg gagagccccg gcgcggagca ggcgggggac   60
ggtattcaga attcgagcgc aggagctccg cttctccacc tgctcccggg gagctattgg  120
gatccagaga atcacccgct gatggttttt gcccaggcct gaaacaacca gagagctacg  180
ggaaaggaag ggcttggctt gccagaggaa ttttccaagt gctcaaacgc caggcttacg  240
gcgcctgtga tccgtccagg aggacaaagt gggatttgaa gatccactcc acttctgctc  300
atggcgggcc agggcctgcc cctgcacgtg gccacactgc tgactgggct gctggaatgc  360
ctgggctttg ctgccgtcct ctttggctgg ccttcactag tgtttgtctt caagaatgaa  420
gattacttta aggatctgtg tggaccagat gctgggccga ttggcaatgc cacagggcag  480
gctgactgca aagcccagga tgagaggttc tcactcatct tcaccctggg gtccttcatg  540
aacaacttca tgacattccc cactggctac atctttgacc ggttcaagac caccgtggca  600
cgcctcatag ccatattttt ctacaccacc gccacactca tcatagcctt cacctctgca  660
ggctcagccg tgctgctctt cctggccatg ccaatgctca ccattggggg aatcctgttt  720
ctcatcacca acctgcagat tgggaaccta tttggccaac accgttcgac catcatcact  780
ctgtacaatg gagcatttga ctcttcctcg gcagtcttcc ttattattaa gcttctttat  840
gaaaaaggca tcagcctcag ggcctgcacc tggcgcctcg agcacgacta tatattgc    898
```

<210> SEQ ID NO 5
<211> LENGTH: 450
<212> TYPE: DNA
<213> ORGANISM: Homo sapiens
<220> FEATURE:
<221> NAME/KEY: misc_feature
<223> OTHER INFORMATION: Incyte ID No: 1907344

<400> SEQUENCE: 5

```
gctcagctgt gggcttagga agcagagcct ggggcatctc caccatggcc tggacccctc   60
tcctcctcca gcttctcacc ctctgctcag ggtcctgggc acagtctgcg ctgacccagg  120
aagcctcggt gtcagggacc gtgggacaga aggtcacct gtccgttct ggaaacaaca  180
acaacattgg aagttatgct gtgggctggt accaacagat ttctcacggt gttctcaaaa  240
ctgtgatatt tggaaattct ccgccctcag gatcccctta ccgcttctct ggctcaaagt  300
ctgggaccac agcctccctg actatctcgg gcctccagcc tgaggacgag gctgattatt  360
attttttcaac atgggactac agactcagtg ctgtggtttt cggcggaagg accaaactga  420
ccgtcctagg tcagcccaag gctgccccct                                    450
```

<210> SEQ ID NO 6

```
<211> LENGTH: 2111
<212> TYPE: DNA
<213> ORGANISM: Homo sapiens
<220> FEATURE:
<221> NAME/KEY: misc_feature
<223> OTHER INFORMATION: Incyte ID No: 1963651
<221> NAME/KEY: unsure
<222> LOCATION: 466, 492, 548, 1337, 1349-1351, 1353-1354, 1362, 1364-1366, 1374,
      1384-1386, 1400, 1423, 1434, 1467, 1485, 1490, 1507, 1547, 1557, 1564, 1569,
      1582, 1584, 1586, 1590, 1593, 1602, 1604, 1609, 1614, 1624, 1636, 1641, 1643,
      1653, 1655, 1672
<223> OTHER INFORMATION: a, t, c, g, or other

<400> SEQUENCE: 6
aagtgctcag cactaaggga gccagcgcac agcacagcca ggaaggcgag cgagcccagc    60
     cagcccagcc agcccagcca gcccggaggt atctgtgaga taggtgctgc tgtcctgggg   120
     aggtagatgc agacagatta actctcaagg tcatttgatt gcccgcctca gaacgatgga   180
     tctgcatctc ttcgactact cagagccagg gaacttctcg gacatcagct ggccatgcaa   240
     cagcagcgac tgcatcgtgg tggacacggt gatgtgtccc aacatgccca acaaaagcgt   300
     cctgctctac acgctctcct tcatttacat tttcatcttc gtcatcggca tgattgccaa   360
     ctccgtggtg gtctgggtga atatccaggc caagaccaca ggctatgaca cgcactgcta   420
     catcttgaac ctggccattg ccgacctgtg ggttgtcctc accatyccag tctgggtggt   480
     cagtctcgtg gmagcacaac cagtggccca tgggcgagct cacgtgcaaa gtcacacacc   540
     tcatcttytc catcaacctc ttcggcagca ttttcttcct cacgtgcatg agcgtgggcc   600
     gctacctctc catcacctac ttcaccaaca cccccagcag caggaagaag atggtacgcc   660
     gtgtcgtctg catcctggtg tggctgctgg ccttctgcgt gtctctgcct gacacctact   720
     acctgaagac cgtcacgtct gcgtccaaca atgagaccta ctgccggtcc ttctaccccg   780
     agcacagcat caaggagtgg ctgatcggca tggagctgat ctccgttgtc ttgggcttg   840
     ccgttccctt ctccattatc gctgtcttct acttcctgct ggccagagcc atctcggcgt   900
     ccagtgacca ggagaagcac agcagccgga agatcatctt ctcctacgtg gtggtcttcc   960
     ttgtctgctg gttgccctac cacgtggcgg tgctgctgga catcttctcc atcctgcact  1020
     acatccctt cacctgccgg ctggagcacg ccctcttcag ggccctgcat gtcacacagt  1080
     gcctgtcgct ggtgcactgc tgcgtcaacc ctgtcctcta cagcttcatc aatcgcaact  1140
     acaggtacga gctgatgaag gccttcatct tcaagtactc ggccaaaaca gggctcacca  1200
     agctcatcga tgcctccaga gtctcagaga cggagtactc tgccttggag cagagcacca  1260
     aatgatctgc cctggagagg tctgggacg ggtttacttg tttttgaaca gggtgatggg  1320
     ccctatggtt ttctagrgca aagcaaagym scyycgggga aycyyratcc cccscttgag  1380
     tccmsmgtga agaggggags acgtgcccca gcttggcatc cawtctctct tggkctcttg  1440
     atgacgcagc tgtcatttgg ctgtaarcaa gtgctgacag ttttscaacr gggcagagct  1500
     gttgtcscac agccagtgcc tgtgccgtca gagcccagct gaggacmggc ttgccckgga  1560
     cctyctgawa agataggatt tyckgkgtty cckgaatttt twawatggkg attkgtattt  1620
     aaawtttaag accttwattt ycycactatt ggkgkacctt ataaatgtat tkgaaagtta  1680
     aatatatttt aaatattgtt tgggaggcat agtgctgaca tatattcaga gtgttgtagt  1740
     tttaaggtta gcgtgacttc agttttgact aaggatgaca ctaattgtta gctgttttga  1800
     aattatatat atataaatat atataaatat ataaatatat gccagtcttg gctgaaatgt  1860
     tttatttacc atagttttat atctgtgtgg tgttttgtac cggcacggga tatgaaacga  1920
     aaactgcttt gtaatgcagt ttgtgacatt aatagtattg taagttaca ttttaaaata  1980
     aacaaaaaac tgttctggac tgcaaatctg cacacacaac gaacagttgc atttcagaga  2040
     gttctctcaa tttgtaagtt attttttttt aataaagatt tttgtttcct aaaaatgcaa  2100
     aaaaaaaaa a                                                        2111

<210> SEQ ID NO 7
<211> LENGTH: 700
<212> TYPE: DNA
<213> ORGANISM: Homo sapiens
<220> FEATURE:
<221> NAME/KEY: misc_feature
<223> OTHER INFORMATION: Incyte ID No: 1976095
<221> NAME/KEY: unsure
<222> LOCATION: 21, 57
<223> OTHER INFORMATION: a, t, c, g, or other

<400> SEQUENCE: 7
gacgccagcg cctgcagagg ntgagcaggg aaaaagccag tgcccagcg gaagacnagc    60
     tcagagctgg tctgccatgg acatcctggt cccactcctg cagctgctgg tgctgcttct   120
     taccctgccc ctgcacctca tggctctgct gggctgctgg cagccctgt gcaaaagcta   180
     cttcccctac ctgatggccg tgctgactcc caagagcaac cgcaagatgg agagcaagaa   240
     acgggagctc ttcagccaga taaaggggct tacaggagcc tccgggaaag tggccctact   300
     ggagctgggc tgcgaaccg gagccaactt tcagttctac ccaccgggct gcagggtcac   360
     ctgcctagac ccaaatcccc actttgagaa gttcctgaca aagagcatgg ctgagaacag   420
     gcacctccaa tatgagcggt ttgtggtggc tcctgagag acatgagac agctggctga   480
     tggctccatg gatgtggtgg tctgcactct ggtgctgtgc tctgtgcaga gcccaaggaa   540
     ggtcctgcag gaggtccgga gagtactgag accggaggt gtgctctttt tctgggagca   600
     tgtggcagaa ccatatgaa gctgggcctt catgtggcag caagttttcg agcccacctg   660
     gaaacacatt gggggatggct tgctgcctca ccagagagac                        700
```

<210> SEQ ID NO 8
<211> LENGTH: 363
<212> TYPE: DNA
<213> ORGANISM: Homo sapiens
<220> FEATURE:
<221> NAME/KEY: misc_feature
<223> OTHER INFORMATION: Incyte ID No: 2417676
<221> NAME/KEY: unsure
<222> LOCATION: 330
<223> OTHER INFORMATION: a, t, c, g, or other

<400> SEQUENCE: 8

```
gggaatttcc cttatctcct tcgcagtgca gctccttcaa cctcgccatg gcctctgccg    60
gaatgcagat cctgggagtc gtcctgacac tgctgggctg ggtgaatggc ctggtctcct   120
gtgccctgcc catgtgtgaag gtgaccgctt tcatcggcaa cagcatcgtg gtgcccagg   180
tggtgtggga gggcctgtgg atgtcctgcg tggtgcagag caccggccag atgcagtgca   240
aggtgtacga ctcactgctg gcgctgccac aggacctgca ggctgcacgt gccctctgtg   300
tcatcgccct ccttgtggcc ctgttcggcn tgctggtcta ccttgctggg gccaagttta   360
cca                                                                  363
```

<210> SEQ ID NO 9
<211> LENGTH: 575
<212> TYPE: DNA
<213> ORGANISM: Homo sapiens
<220> FEATURE:
<221> NAME/KEY: misc_feature
<223> OTHER INFORMATION: Incyte ID No: 1805538
<221> NAME/KEY: unsure
<222> LOCATION: 2, 4
<223> OTHER INFORMATION: a, t, c, g, or other

<400> SEQUENCE: 9

```
cngntcgagg ctaagaggac aggatgaggc ccggcctctc atttctccta gcccttctgt    60
tcttccttgg ccaagctgca ggggatttgg gggatgtggg acctccaatt cccagccccg   120
gcttcagctc tttcccaggt gttgactcca gctccagctt cagctccagc tccaggtcgg   180
gctccagctc cagccgcagc ttaggcagcg gaggttctgt gtcccagttg ttttccaatt   240
tcaccggctc cgtggatgac cgtgggacct gccagtgctc tgtttccctg ccagacacca   300
cctttcccgt ggacagagtg gaacgcttgg aattcacagc tcatgttctt tctcagaagt   360
ttgagaaaga actttccaaa gtgagggaat atgtccaatt aattagtgtg tatgaaaaga   420
aactgttaaa cctaatgtcc gaattgacat catggagaag gataccattt cttacactga   480
actggacttc gagctgatca aggtagaagt gaaggagatg gaaaaactgg tcatacagct   540
gaaggagagt ttggtggaag tcagaaattg ttgac                              575
```

<210> SEQ ID NO 10
<211> LENGTH: 1637
<212> TYPE: DNA
<213> ORGANISM: Homo sapiens
<220> FEATURE:
<221> NAME/KEY: misc_feature
<223> OTHER INFORMATION: Incyte ID No: 1869688
<221> NAME/KEY: unsure
<222> LOCATION: 3, 13, 22, 44, 69, 162, 1220, 1426, 1443, 1458, 1465, 1486, 1488, 1490,
    1517, 1522, 1524-1525, 1533, 1553, 1573, 1584, 1605, 1624, 1631, 1634-1635
<223> OTHER INFORMATION: a, t, c, g, or other

<400> SEQUENCE: 10

```
acncagcctt ttncccgatt cncccttttcc tgccttcggt ttcntcccaa ttcttaccca    60
tccctacna gctgccatcc ctgacaccct tctctcctgg gccacgcagt ccaacctgaa   120
cgggagcggg gaggtatcct ggcaccttcc ttggctctta cnccctcggtt tctcacagcg   180
gggccggcgc cgccatggcg gccgtgtttg atttggatt ggagacggag gaaggcagcg   240
agggcgaggg cgagccagag ctcagccccg cggacgcatg tcccccttgcc gagttgaggg   300
cagctggcct agagcctgtg ggacactatg aagaggtgga gctgactgag accagcgtga   360
acgttggccc agagcgcatc gggccccact gctttgagct gctgcgtgtg ctgggcaagg   420
ggggctatgg caaggtgttc caggtgcgaa aggtgcaagg caccaacttg ggcaaaatat   480
atgccatgaa agtcctaagg aaggccaaaa ttgtgcgcaa tgccaaggac acagcacaca   540
cacgggctga gcggaacatt ctagagtcag tgaagcaccc ctttattgtg gaactggcct   600
atgccttcca gactggtggc aaactctacc tcatccttgg attgcctcag tggtggcgag   660
ctcttcacgc atctgagcg agagggcatc ttcctggaag atacggcctg cttctacctg   720
gctgagatca cgctggccct gggccatctc cactcatcta gcatcatcta cgcggacctc   780
aagccgaga acatcatgct cagcagccag ggccacatca aactgaccga ctttggactc   840
tgcaaggagt ctatccatga gggcgccgtc actcacacct tctgcggcac cattgagtac   900
atggcccctg agattctggt gcgcagtggc cacaaccggg ctgtggactg tggagcctgg   960
ggggccctga tgtacgacat gctcactgga tcgccgccct tcaccgcaga gaaccggaag  1020
```

```
aaaaccatgg ataagatcat caggggcaag ctggcactgc ccccctacct cacccccagat 1080
gcccgggacc ttgtcaaaaa gtttctgaaa cggaatccca gccagcggat tgggggtggc 1140
ccaggggatg ctgctgatgt gcagagacat ccctttttcc ggcacatgaa ttgggacgac 1200
ttctggcctg gcgtgtggan cccccttttca aggccctgtc tgcagtcaga ggagacgtga 1260
gcagtttgat acccgcttca cacggcagac gccggtggac agtcctgatg acacagcctc 1320
agcgagagtg ccaacaaggc cttcctgggg ttacataagt ggcgcgtctg tcctggacag 1380
atcaagaggt tctctttcag cccaagtggg tcaaccaggg ctcaanatag ccccgggtcc 1440
gtnagcccct caagtttncc ctttnagggt tcggccagcc accttncngn gccaaggagt 1500
acttactcaa tctgcanggg gngnnttgac aangccttt ccatcgtccc ctnagggcaa 1560
aattaaaagg gcntgggtta aggntagaac cggtgggta taagntccct tagccgtcct 1620
gggnttaaaa naanntg                                              1637
```

<210> SEQ ID NO 11
<211> LENGTH: 1124
<212> TYPE: DNA
<213> ORGANISM: Homo sapiens
<220> FEATURE:
<221> NAME/KEY: misc_feature
<223> OTHER INFORMATION: Incyte ID No: 1880692

<400> SEQUENCE: 11

```
ggaagagcag cggcgaggcg gcggtggtgg ctgagtccgt ggtggcagag gcgaaggcga 60
cagctctagg ggttggcacc ggccccgaga ggaggatgcg ggtccggata gggctgacgc 120
tgctgctgtg tgcggtgctg ctgagcttgg cctcggcgtc ctcggatgaa gaaggcagcc 180
aggatgaatc cttagattcc aagactactt tgacatcaga tgagtcagta aggaccata 240
ctactgcagg cagagtagtt gctggtcaaa tatttcttga ttcagaagaa tctgaattag 300
aatccctctat tcaagaagag gaagacagcc tcaagagcva agtggggaa agtgtcacag 360
aagatatcag cttctctagag tctccaaatc cagaaaacaa ggactatgaa gagccaaaga 420
aagtacggaa accagctttg accgccattg aaggcacagc catggggag ccctgccact 480
tcccttttct tttcctagat aaggagtatg atgaatgtac atcagatggg agggaagatg 540
gcagactgtg gtgtgctaca acctatgact acaagcaga tgaaaagtgg ggcttttgtg 600
aaactgaaga agaggctgct aagagacggc agatgcagga agcagaaatg atgtatcaaa 660
ctggaacgaa aatccttaat ggaagcaata agaaaagcca aaaaagagaa gcatatcggt 720
atctccaaaa ggcagcaagc atgaaccata ccaagccct ggagagagtg tcatatgctc 780
tttattgg tgattacttg ccacagaata tccaggcagc gagagatg tttgagaagc 840
tgactgagga aggctctccc aagggacaga ctgctcttgg ctttctgtat gcctctgac 900
ttggtgttaa ttcaagtcag gcaaagctc ttgtatta tacatttga gctcttgggg 960
gcaatctaat agcccacatg gttttgggtt acagatactg gctggcatc ggcgtcctcc 1020
agagttgtga atctgccctg actcactatc gtcttgttgc caatcatggt atctatgttt 1080
cccttttac cttttaggaa aaaaataa atggaattaa cttt 1124
```

<210> SEQ ID NO 12
<211> LENGTH: 1452
<212> TYPE: DNA
<213> ORGANISM: Homo sapiens
<220> FEATURE:
<221> NAME/KEY: misc_feature
<223> OTHER INFORMATION: Incyte ID No: 318060
<221> NAME/KEY: unsure
<222> LOCATION: 3, 472, 484, 486, 499, 501-502, 504, 508, 513, 572, 577, 637, 642, 646,
       650, 655, 669, 688, 698, 1288, 1291
<223> OTHER INFORMATION: a, t, c, g, or other

<400> SEQUENCE: 12

```
cancaggtgt ttattagggt cctttttcat taccccagag acagaccag ggctggctac 60
gtgcacagga agtaacgctt gccacatgca taaatacgtg aaggtgcaca ttacatcagc 120
acagattcac aaaacacctc gccttgcaa gaaaactgta gctaggcagc tcccgtcctc 180
agggactcct gccacagacg tcatggagac agcatgagcc tcccccagaac agtcccacg 240
gcctagactc cccagagcag gaggagcagc caggctctg ttgcgagaca gccatcactt 300
cctgttcttt gcaggtgcct aaggtaggtt acctggcaa ggttttgtg gaaaaaatga 360
gttttttcaa tgttgcaggt ctttaatag ttcatctgta ggaagtgcat ttgcaaagtc 420
accaacctgc agcttccatc tgtagaccag gaaggtgat tctctgggtg ancacagcgg 480
ggcntnccct gaggtacana nntncccncc canaccccg cagtgtcctc acagccatca 540
caggctttgg aagtttggct caagcaaggc cnttgcnaag gccccaacc cccttcatgg 600
ttgggcttct gctgtgaaag ccaatccctc ccgttngggg cnagcnaagn tcaangggcc 660
ttaccccang aggccattct tgaagggntt gtaaatnga agcaggaagc tgtgtggaag 720
gagaagctgg tggccacaga agatcctgc tctgcttcat ttacaagcct 780
caagatggct ctgtgtaggg cctgagcttg ctgcccaacg gcgaggatggc ttcacagcag 840
agccagcatg aggggtgggg cctggcaggg cttgcttgag ccaaactgca aagggctgtgg 900
tggctgtgag gacactgcgg gggttggggg ggggcgtctg tacctcaggg gatgccccgc 960
tgtggtcacc cagagaatca ccctcctgg tctacagatg gaagctgcag gttggtgact 1020
ttgcaaatgc acttcctaca gatgaactat taaaagacct gcaacattga aaaaactcat 1080
tttttccacc aaaaccttgg ccaggtaacc tacctaggc aactgcaaag aacaggaagt 1140
gatggctgtc tcgcaacaga gcctgggctg ctcctcctgc tctggggagt ctaggccgtg 1200
gggactgttc tgggggagct catgctgtct ccatgacgtc tgtgcaagga gtccctgagg 1260
```

```
                            -continued acgggagctg cctaagctac agttttttytt sccaaggcgg aggtgttttg tgaatctgtg   1320
ctgatgtaat gtgcaccttc acgtatttat gcatgtggca agcgttactt cctgtgcacg   1380
tagccagccc tgggtctgtc tctggggtaa tgaaaaagga ccctaataaa cacctgctca   1440
ctggctgggt gg                                                        1452
```

<210> SEQ ID NO 13
<211> LENGTH: 280
<212> TYPE: DNA
<213> ORGANISM: Homo sapiens
<220> FEATURE:
<221> NAME/KEY: misc_feature
<223> OTHER INFORMATION: Incyte ID No: 396450
<221> NAME/KEY: unsure
<222> LOCATION: 19, 29, 43, 49, 69, 75, 86, 112, 115, 130, 185, 200, 244, 252, 254, 267, 278
<223> OTHER INFORMATION: a, t, c, g, or other

<400> SEQUENCE: 13

```
ggggaagaag agccgcganc gagagaggnc ggcgagcgtc ccnggcctna gagagcagcc    60
tcccgagana ggcanttgct ggattntcca aaagtatctg cagtggctgt tncancagga   120
gagcctcagn ctgcctggaa gatgccgaga tcgtgctgca gccgctcggg ggccctgttg   180
ctggncttgc tgcttcaggn ctccatggaa gtgcgtggct ggtgcctgga gagcagccag   240
tgtnaggacc tnancaagga aagcaanctg cttgagtnca                         280
```

<210> SEQ ID NO 14
<211> LENGTH: 514
<212> TYPE: DNA
<213> ORGANISM: Homo sapiens
<220> FEATURE:
<221> NAME/KEY: misc_feature
<223> OTHER INFORMATION: Incyte ID No: 506333
<221> NAME/KEY: unsure
<222> LOCATION: 378, 393, 428, 444, 460
<223> OTHER INFORMATION: a, t, c, g, or other

<400> SEQUENCE: 14

```
tgtggagtca gcccagtctg gatgcacagg aggatgctgg cggcacagtg agtgaggcct    60
ggtgccagag ctgtgcggac cccttgttgg ccatggagca gcaggcccag aggccctctc   120
cccagccctg cttgcctgcc tcggagagga cagaggccta ggcccacggg ggagggtgtt   180
ggcagacaga tgccctccag gccctgggc ctccttaacg gcccttaac gacacgcgtg    240
ccaagggtgg aggatgccag ccaaggggcg ctacttcctc aacgagggcg aggagggccc   300
tgaccaagat gcgctctacg agaagtacca gctcaccagc cagcatgggc cgctgctgct   360
cacgctcctg ctggtggncg caatgcctgc gtngccctca tcatattgcc tcagccaggg   420
ggtgagtnaa ggcagcccct gggntcaagt ctcggcccan actttggcaa gtgctatctt   480
ctcttagctc ttctgaaaat gcttatcttc tgta                               514
```

<210> SEQ ID NO 15
<211> LENGTH: 617
<212> TYPE: DNA
<213> ORGANISM: Homo sapiens
<220> FEATURE:
<221> NAME/KEY: misc_feature
<223> OTHER INFORMATION: Incyte ID No: 764465
<221> NAME/KEY: unsure
<222> LOCATION: 537, 578, 598, 606
<223> OTHER INFORMATION: a, t, c, g, or other

<400> SEQUENCE: 15

```
aaactacatt ttgcaaagtc attgaactct gagctcagtt gcagtactcg ggaagccatg    60
caggatgaag atggatacat caccttaaat attaaaactc ggaaaccagc tctcgtctcc   120
gttggccctg catcctcctc ctggtggcgt gtgatggctt tgattctgct gatcctgtgc   180
gtggggatgg ttgtcgggct ggtggctctg gggatttggt ctgtcatgca gcgcaattac   240
ctacaagatg agaatgaaaa tcgcacagga actctgcaac aattagcaaa gcgcttctgt   300
caatatgtgg taaaacaatc agaactaaaa gggcactttc aaaggtcata aatgcagccc   360
ctgtgacaca aactggagta attatggaga tagctgctat gggttcttca ggcacaactt   420
aacatgggaa gagagtaagc agtactgcac tgacatgaat gctactctcc tgaagattga   480
caaccggaac attgtggagt acatcaaagc caggactcat ttaattcgtt tgggtcngat   540
tatctcgcca gaagtcgaat gaggtctgga agtggganga tggctcgggt atctcagnaa   600
atatgnttga gttttttg                                                  617
```

<210> SEQ ID NO 16
<211> LENGTH: 350

```
<212> TYPE: PRT
<213> ORGANISM: Homo sapiens
<220> FEATURE:
<221> NAME/KEY: misc_feature
<223> OTHER INFORMATION: Incyte ID No: 2547002CD1

<400> SEQUENCE: 16

Met Ala Leu Glu Gln Asn Gln Ser Thr Asp Tyr Tyr Tyr Glu Glu
     1               5                  10                  15
    Asn Glu Met Asn Gly Thr Tyr Asp Tyr Ser Gln Tyr Glu Leu Ile
                    20                  25                  30
    Cys Ile Lys Glu Asp Val Arg Glu Phe Ala Lys Val Phe Leu Pro
                    35                  40                  45
    Val Phe Leu Thr Ile Val Phe Val Ile Gly Leu Ala Gly Asn Ser
                    50                  55                  60
    Met Val Val Ala Ile Tyr Ala Tyr Lys Lys Gln Arg Thr Lys
     65                  70                                  75
    Thr Asp Val Tyr Ile Leu Asn Leu Ala Val Ala Asp Leu Leu Leu
                    80                  85                  90
    Leu Phe Thr Leu Pro Phe Trp Ala Val Asn Ala Val His Gly Trp
                    95                 100                 105
    Val Leu Gly Lys Ile Met Cys Lys Ile Thr Ser Ala Leu Tyr Thr
                   110                 115                 120
    Leu Asn Phe Val Ser Gly Met Gln Phe Leu Ala Cys Ile Ser Ile
                   125                 130                 135
    Asp Arg Tyr Val Ala Val Thr Lys Val Pro Ser Gln Ser Gly Val
                   140                 145                 150
    Gly Lys Pro Cys Trp Ile Ile Cys Phe Cys Val Trp Met Ala Ala
                   155                 160                 165
    Ile Leu Leu Ser Ile Pro Gln Leu Val Phe Tyr Thr Val Asn Asp
                   170                 175                 180
    Asn Ala Arg Cys Ile Pro Ile Phe Pro Arg Tyr Leu Gly Thr Ser
                   185                 190                 195
    Met Lys Ala Leu Ile Gln Met Leu Glu Ile Cys Ile Gly Phe Val
                   200                 205                 210
    Val Pro Phe Leu Ile Met Gly Val Cys Tyr Phe Ile Thr Ala Arg
                   215                 220                 225
    Thr Leu Met Lys Met Pro Asn Ile Lys Ile Ser Arg Pro Leu Lys
                   230                 235                 240
    Val Leu Leu Thr Val Val Ile Val Phe Ile Val Thr Gln Leu Pro
                   245                 250                 255
    Tyr Asn Ile Val Lys Phe Cys Arg Ala Ile Asp Ile Ile Tyr Ser
                   260                 265                 270
    Leu Ile Thr Ser Cys Asn Met Ser Lys Arg Met Asp Ile Ala Ile
                   275                 280                 285
    Gln Val Thr Glu Ser Ile Ala Leu Phe His Ser Cys Leu Asn Pro
                   290                 295                 300
    Ile Leu Tyr Val Phe Met Gly Ala Ser Phe Lys Asn Tyr Val Met
                   305                 310                 315
    Lys Val Ala Lys Lys Tyr Gly Ser Trp Arg Arg Gln Arg Gln Ser
                   320                 325                 330
    Val Glu Glu Phe Pro Phe Asp Ser Glu Gly Pro Thr Glu Pro Thr
                   335                 340                 345
    Ser Thr Phe Ser Ile
                   350

<210> SEQ ID NO 17
<211> LENGTH: 1660
<212> TYPE: DNA
<213> ORGANISM: Homo sapiens
<220> FEATURE:
<221> NAME/KEY: misc_feature
<223> OTHER INFORMATION: Incyte ID No: 2547002CB1

<400> SEQUENCE: 17
gcgacgtaca acagattgga gccatggctt tggaacagaa ccagtcaaca gattattatt   60
    atgaggaaaa tgaaatgaat ggcacttatg actacagtca atatgaactg atctgtatca  120
    aagaagatgt cagagaattt gcaaaagttt tcctccctgt attcctcaca atagtttttcg  180
    tcattggact tgcaggcaat tccatggtag tggcaattta tgcctattac aagaaacaga  240
    gaaccaaaac agatgtgtac atcctgaatt tggctgtagc agatttactc cttctattca  300
    ctctgccttt tgggctgtt aatgcagttc atgggtgggt tttagggaaa ataatgtgca  360
    aaataacttc agccttgtac acactaaact ttgtctctgg aatgcagttt ctggcttgta  420
    tcagcataga cagatatgtg gcagtaacta agtccccag ccaatcagga gtgggaaaac  480
    catgctggat catctgtttc tgtgtctgga tggctgccat cttgctgagc ataccccagc  540
    tggttttta cacagtaaat gacaatgcta ggtgcattcc cattttcccc cgctacctag  600
    gaacatcaat gaaagcattg attcaaatgc tagagatctg cattggattt gtagtaccct  660
```

-continued

```
       ttcttattat ggggtgtgc tactttatca cagcaaggac actcatgaag atgccaaaca   720
       ttaaaatatc tcgacccta aagttctgc tcacagtcgt tatagttttc attgtcactc   780
       aactgcctta taacattgtc aagttctgcc gagccataga catcatctac tccctgatca   840
       ccagctgcaa catgagcaaa cgcatggaca tcgccatca agtcacagaa agcatcgcac   900
       tctttcacag ctgcctcaac ccaatccttt atgttttat gggagcatct ttcaaaaact   960
       acgttatgaa agtggccaag aaatatggt cctggagaag acagagacaa agtgtggagg  1020
       agtttccttt tgattctgag ggtcctacag agccaaccag tactttagc atttaaaggt  1080
       aaaactgctc tgcctttgc ttggatacat atgaatgatg ctttccctc aaataaaaca  1140
       tctgcattat tctgaaactc aaatctcaga cgccgtggtt gcaacttata ataaagaatg  1200
       ggttggggga aggggagaa ataaaagcca agaagaggaa acaagataat aaatgtacaa  1260
       aacatgaaaa ttaaaatgaa caatatagga aaataattgt aacaggcata agtgaataac  1320
       actctgctgt aacgaagaag agctttgtgg tgataatttt gtatcttggt tgcagtggtg  1380
       cttatacaaa tctacacaag tgataaaatg acagagaact atatacacac attgtaccaa  1440
       tttcaatttc ctggttttga cattatagta taattatgta agatggaacc attggggaaa  1500
       actgggtgaa gggtacccag gaccactctg taccatcttt gtaacttcct gtgaatttat  1560
       aataatttca aaataaaaca agttaaaaaa aaacccact atgctataag ttaggccatc  1620
       taaaacagat tattaaagag gttcatgtta aaaggcatgc                        1660
```

<210> SEQ ID NO 18
<211> LENGTH: 212
<212> TYPE: DNA
<213> ORGANISM: Homo sapiens
<220> FEATURE:
<221> NAME/KEY: misc_feature
<223> OTHER INFORMATION: Incyte ID No: 5269342F6

<400> SEQUENCE: 18

```
       gttcaaggat ggccaaaaca aactacgttg gcatttcaga atcccgtc catggccaaa    60
       actattacca aagactcgat ctatgactca tttgacagag aagccaagga aaaacagctt  120
       gcttggccca ttaactcaaa tccaccaaat acttttgtct aagttctcat tctttcaatt  180
       gttatgcacc agagattaaa aagctttaac ta                                212
```

<210> SEQ ID NO 19
<211> LENGTH: 707
<212> TYPE: DNA
<213> ORGANISM: Mus musculus
<220> FEATURE:
<221> NAME/KEY: misc_feature
<223> OTHER INFORMATION: Incyte ID No: 051293_Mm.1

<400> SEQUENCE: 19

```
       cgtaatcaat agtgaacatg tttacaaaa cggaagttta gtgaaaacta gtaaatcaa    60
       ttctcactt atagtgaaag cttttaatc tctggcacat aacagtgaaa gacttcttag   120
       aaatcagaca aaagtgtttg gagggttga gttgatgggc caggcgagct tcttctccct   180
       ggcctcccgg tcaaatgagt catagatgga gtctttggtt atggtcctgc tcacgggagg   240
       gatttccgaa atgcccacat agtttcttt ggccatccgt gagctggtcg tgatggtgta   300
       ggcattgctg cggtagcatt tcatcgagga catgcagaat gtctctttca tccctctccg   360
       aaaattggca ttataaatag agtacagagt gggtttcgag ctgaagagc tgaaagatac   420
       ccacgtgact gccgtgaaga caagggagct cttcttgtag tcttgctcat ggggatgcca   480
       gagctgagcc acatggaaag gtagccagga gaacaggaac actaggttca agagcaggaa   540
       catcttgacc gttttcacct ttgtcctggg gacaatgttc atcgtccttc tcagcgtccg   600
       cccgtccgtg cctattctcc agatatactt tatgaccttc tggtaaaaca ggattatgag   660
       gatggaggga atcacgaagc ccaccaagaa gtggatgacg gtatagg              707
```

<210> SEQ ID NO 20
<211> LENGTH: 781
<212> TYPE: DNA
<213> ORGANISM: Rattus norvegicus
<220> FEATURE:
<221> NAME/KEY: misc_feature
<223> OTHER INFORMATION: Incyte ID No: 703901370J1

<400> SEQUENCE: 20

```
       gaagtttagt gaaaactaag taaatcaatt ctctttatag ttaaagctt ttttcttctt    60
       tttttaaatc tctggcacat aacagtgaag gagttcttag aaattagaca aaagtgtttg   120
       gtgggtttga gttgatgggc caggcgagct tcttctccct ggcctcacgg tcaaatgagt   180
       catagatgga gtcttggtta tcgtcctgct cacgggaggg atttccgaaa tgcccacata   240
       gtttctttgg ccatccttga actggtcgtg atggtgtagg cattgctgcg taacatttc    300
       attgaggaca tgcagaaagt ctctttcatc cctctccgaa aattggcgtt ataaatagag   360
       tacagagtgg gtttagaggc cgaagagctg aaagacaccc acgtgactgc tgtgaaaaca   420
       agggagctct tcctgtagtc ttgctcatgg ggatgccaga gctgagccac atgaaaggc    480
       agccaggaga acaggaacac aaggttcaag agcagaaaca tcttgaccgt cttcaccttg   540
       gtcctgggga caatgttcat tgtcctcctc agggtccgcc cgtccgtgcc tattctccag   600
```

```
                   atatacttta tgactttctg gtaaaacagg attatgagga cacgagggaa tcacaaagcc   660
                   caccaagaag tggataacag tataggcagt tccctcccag gagggtggga ggaagtagtt   720
                   acagtggtta tcccagttag agcccgtaga aaacagaaga caggcttcac gaaggctgcg   780
                   t                                                                    781
```

<210> SEQ ID NO 21
<211> LENGTH: 823
<212> TYPE: DNA
<213> ORGANISM: Rattus norvegicus
<220> FEATURE:
<221> NAME/KEY: misc_feature
<223> OTHER INFORMATION: Incyte ID No: 296771_Rn.1

<400> SEQUENCE: 21

```
                   acgcagcctt cgtgaagcct gtcttctgtt ttctacgggc tctaactggg ataaccactg    60
                   taactacttc ctcccaccct cctgggaggg aactgcctat actgttatcc acttcttggt   120
                   gggctttgtg attccctctg tcctcataat cctgttttac cagaaagtca taaagtatat   180
                   ctggagaata ggcacggacg gcggaccct gaggaggaca atgacattg tccccaggac     240
                   caaggtgaag acggtcaaga tgtttctgct cttgaacctt gtgttcctgt tctcctggct   300
                   gcctttccat gtggctcagc tctggcatcc ccatgagcaa gactacagga agagctccct   360
                   tgttttcaca gcagtcacgt gggtgtcttt cagctcttcg gcctctaaac ccactctgta   420
                   ctctatttat aacgccaatt ttcgagagag gatgaaagag actttctgca tgtcctcaat   480
                   gaaatgttac cgcagcaatg cctacaccat tcaaggatgg ccaaaagaaa                540
                   ctatgtgggc atttcggaaa tccctcccgt gagcaggacg ataaccaaag actccatcta   600
                   tgactcattt gaccgtgagg ccagggagaa gaagctcgcc tggcccatca actcaaaccc   660
                   accaaaacact tttgtctaat ttctaagaac tccttcactg ttatgtgcca gagatttaaa   720
                   aaaagaagaa aaaaagcttt aactataaag agaattgatt tacttagttt tcactaaact   780
                   tccttgttgt aaataaaaat caaaatatata aacattgcgg ccg                      823
```

<210> SEQ ID NO 22
<211> LENGTH: 465
<212> TYPE: DNA
<213> ORGANISM: Homo sapiens
<220> FEATURE:
<221> NAME/KEY: misc_feature
<223> OTHER INFORMATION: Incyte ID No: 1457779F6
<221> NAME/KEY: unsure
<222> LOCATION: 416, 454
<223> OTHER INFORMATION: a, t, c, g, or other

<400> SEQUENCE: 22

```
                   cctggagcca ggtgcacagc gcatcgcccg aggctgtcac cgccctgccc cgcccacccc    60
                   agctgtcctg gacccagggg cagggagagg ctggacgcca ggtgcgcgga cacagaagcg   120
                   tctaagcaca gcttcctcct tgccgctccg ggaagtgggc agccagccca ggaaccagta   180
                   ccacctgcac catggggctg tcccggaagg agcaggtctt cttgccctg ctgggggcct     240
                   cggggtctc aggcctcacg gcactcattc tcctcctgtg ggaggccacc agcgtgctcc      300
                   tgcccacaga catcaagttt gggatcgtgt ttgatgcggg ctcctcccac acgtccctct   360
                   tcctgtatca gtggccggcg aacaaggaga atgatgcacggg tgtggtcagc caggcnctgg   420
                   cctgccaggt ggaagggctg gaatctcctc ctanaattct aatgc                    465
```

<210> SEQ ID NO 23
<211> LENGTH: 766
<212> TYPE: DNA
<213> ORGANISM: Mus musculus
<220> FEATURE:
<221> NAME/KEY: misc_feature
<223> OTHER INFORMATION: Incyte ID No: 023793_MM.1

<400> SEQUENCE: 23

```
                   ggcaagatgt aagcctggaa ttaatgagat agagtaaaat tagtagatgc cagagcagca    60
                   gctagagagc agcctgctcc tcccaccaca gccccaggtt caagtaggtg gagacggggt   120
                   gtggaggaca gcaggtgtgc aggtcagaag cagaacttcc tcaagctatc cttgaaagtt   180
                   ggctcccagt gcagctcaga ccctctcacc atgggactct cctgaaagga acgggtcttc   240
                   atggctctgt tgggagttgc agcagcctct ggcctcacca tgctcgtcct catcctggtg   300
                   aaggcaatca atgttctctt gcctgcagac accaagtttg ggattgtgtt tgatgcgtcc   360
                   tcctcccaca catccctgtt tgtgtaccag tggccagcaa acaaggagaa ggcacagga     420
                   gtggtcagcc aggccctgac ttgccagata gaaggacctg gaatctcttc ctatacctct   480
                   gacccgacac aggctgggga agcctgaag agctgcctgg aggaggcgct ggcgttgatc    540
                   ccacaggccc agatcccaga gacgcccaca ttcttgggt ccacagcagg aatgaggctg      600
                   ctcagccaga agaacagctc tcaggcaaga gacatcctag gctgcaagtc tcccagacac   660
                   tcacgcaagt ctcctgtgga ttccggggtg ctaagatctt ggctgggcag atgacggtg     720
                   ccttacggct ggatacacca tcaactatgt ccttgggaat tgctcc                   766
```

<210> SEQ ID NO 24
<211> LENGTH: 239
<212> TYPE: DNA
<213> ORGANISM: Rattus norvegicus
<220> FEATURE:
<221> NAME/KEY: misc_feature
<223> OTHER INFORMATION: Incyte ID No: 701923941H1

<400> SEQUENCE: 24

```
caggagtggt cagccaggcc ctggcttgcc aggtagaagg accgggaatc tcgtcctaca   60
cctctgaccc gacacaggct ggggagagcc tgaagagctg cctgcaggag gcgctggcac  120
tgatcccaca gacccagcat ccagtgacgc ccacattcct ggggccaca  gcaggaatga  180
ggctgctcag ccagaagaac agctctcagg ctcaagacat cctagctgca gtctcccag   239
```

<210> SEQ ID NO 25
<211> LENGTH: 239
<212> TYPE: DNA
<213> ORGANISM: Rattus norvegicus
<220> FEATURE:
<221> NAME/KEY: misc_feature
<223> OTHER INFORMATION: Incyte ID No: 317489_Rn.1

<400> SEQUENCE: 25

```
caggagtggt cagccaggcc ctggcttgcc aggtagaagg accgggaatc tcgtcctaca   60
cctctgaccc gacacaggct ggggagagcc tgaagagctg cctgcaggag gcgctggcac  120
tgatcccaca gacccagcat ccagtgacgc ccacattcct ggggccaca  gcaggaatga  180
ggctgctcag ccagaagaac agctctcagg ctcaagacat cctagctgca gtctcccag   239
```

<210> SEQ ID NO 26
<211> LENGTH: 481
<212> TYPE: DNA
<213> ORGANISM: Homo sapiens
<220> FEATURE:
<221> NAME/KEY: misc_feature
<223> OTHER INFORMATION: Incyte ID No: 2444714F6

<400> SEQUENCE: 26

```
cgctgaaacc ctgggcggcg gcaagctgtg cgacctcttc tgcggccggc ctgggcaggt   60
gtcttcctcg agaggcaggc aggggatccc ggacccttat acaggatgct gtgttctttg  120
ctcctttgtg aatgtctagt gctggtagct ggttatgctc atgatgatga cctgattgat  180
cccacagaca tgcttaacta tgatgctgct tcaggaacaa tgagaaaatc tcaggcaaaa  240
tatggtattt caggggaaaa ggatgtcagt cctgacttgt catgtgctga tgaaatatca  300
gaatgttatc acaaacttga ttctttaact tataagattg atgagtgtga aagaaaaag   360
agggaagact atgaaagtca aagcaatcct gttttaggga gatacttaaa taagatttta  420
attgaagctg gaaagcttgg acttcctgat gaaaacaaag gcgatatgca ttatgatgct  480
g                                                                481
```

<210> SEQ ID NO 27
<211> LENGTH: 765
<212> TYPE: DNA
<213> ORGANISM: Canis familiaris
<220> FEATURE:
<221> NAME/KEY: misc_feature
<223> OTHER INFORMATION: Incyte ID No: 703711491J1

<400> SEQUENCE: 27

```
aaagctgtct aacctattgt gattttccaa aaagcctgct gctaaaatcc ttgatttaa   60
taataaatat gggctggaca ataaacaatt ctattcgaat tatgaactgg ccttgatctg  120
ctcagtctgc tttattgtct tccctaaatt gctgtcaaca gcagcagtgt gttgccctgc  180
tagctctcaa agtggactgc atccccaac ggttatctgt aataaaagaa gacaaagagg  240
agatttttact taattttta cagattcatt ctcggataaa aagcagtcga gttcaaacag  300
cattaactcc actctcacag ctccaggctg tcacctgaga cagtcactgc tcttcagaat  360
ccagtcagct cagaggacag ctaccaccta aatgtctcag catattaact gattttccag  420
caccatagca gaaactcagg acagctaacg ccatgatgat gagcactgga atgtgaagga  480
atactgggag ctccttcatg aactctctaa taaattcacc agctccttc  ccgatgtgtt  540
tcaatggctc cgtgacagt ttggtgaatg taactgccag tgcctttgtt ggtgggacca   600
accaaatagg gttgactagt aagagctcat aatattttgg catggtcat  ccttataggt   660
ccatgaactt ctaaacaatt cccaaaggct tcaatccagt ccatcttctc ggcccacaca   720
ttgtttatgg gtccatcttg gcacctcagc tgatgctgtg cgaac                  765
```

```
<210> SEQ ID NO 28
<211> LENGTH: 2100
<212> TYPE: DNA
<213> ORGANISM: Mus musculus
<220> FEATURE:
<221> NAME/KEY: misc_feature
<223> OTHER INFORMATION: Incyte ID No: 060931_Mm.3

<400> SEQUENCE: 28
ctaatgtaaa aataagtgtt tattttgtgt ttacaatggt taagcattca acaattattc    60
    tgttttaaaa agtgctttaa caactaccta ccctgttctt ttcttaaaag ccagttacaa   120
    tgtgctttaa cctcagatag tcacactaat cacttgagac aagccgcttc tcttttctgc   180
    aataaactgg ccttgatatc gtcacctgtg ttaatcaagt cttccctgaa ttgctgtagt   240
    cactcaagaa cagcaggttg ctttgctagc tgtcaaggta gattccatcc ccaaatgggc   300
    atttcaaaga tggctggagc tgtggttgct ctgtgcattg ttcttttagcc acatgggctg   360
    ctgacaggtt cagtcccgtg tgctgccact gcagcttcct tgctgggtgg gcagcctcct   420
    ggtgggctgc actcggagtc tgtcttcagc tgggccttgt ccactgtggg tgagcttttg   480
    ccagcgctgg gaacttggcc agagacatcc ttggcagact ggctgtattc tgtcggggtg   540
    cttcctctg ggagttcacc agtctcaagg tttgtgttca taatgggtga tttatgggct   600
    gggaccactt ctggatgttc ttgtgcctct gtgtcaggta agtcaaatgc ccggagcact   660
    tcagggctct tgttgccaga gtgaaatctc tgtctcaaag catctctctt actcgcatgc   720
    attttgtcat aagggccttg ctcgatggag ccagctgggc ccctgtaaga gaaatctgca   780
    tcacctgctc caccatggag tctatagtca agtcccttct gtcgtcttct gtcatctggc   840
    tcaagtgctc ggggaagttc tctgtcagga ccaccgaagt actcttggca tgggtcatcc   900
    cttccagcac catagcagaa gctcaggaca gccagcgcca ggatcgccag caccggaatc   960
    tgaagtaaca ctggaatctc cttcatgagc gctttaatga attcacctgc tcctttttcca  1020
    atgtgcttta atggttccgt tacaaagtta gtgaatgtaa tcgccagagc ctttgttggt  1080
    ggaaccaacc aaataggggt gactattagg agctcatagt acttttggca tgggtcatcc  1140
    ttataggtcc atgaacttgt aaaccattcc cagagacttc cagtccaatc catcttctta  1200
    gcacataaat tgtcgaaagg ctccatccca gcaatgttag cctgatgctg agcaaaagcc  1260
    atcttataca gatatatcca attccatgct aaactcaaga gaaagctgat gatgaaaatc  1320
    cgtttcatct gtgtgtacca gcgaacataa gtccacagct cgtagccac cagcaccaca  1380
    aggcagagca gacacaagag aaccataaac acattatatg gatctactcc aaaataatct  1440
    tcaaactgcc acttccatgc ttctgaatca tggcacttaa aattgattaa aatgtcactt  1500
    agtgcgtcgt ccagggctcc gggcttccac tcctctccgc tgaggaactt ctgaatctcc  1560
    aacagtgtct gtctgctcag gagaatctca gcatcgtaac gcatctctac tttgttctca  1620
    tcagggagtc caagcttgcc agcttcaatt aaaatcttat ttagatatct cctgaaaaca  1680
    ggattacttt gactttcata atctttcatt ttcttctttt cacaactatc aaccttgtga  1740
    gttaaagaat ccagtctgtg caaacagtct gacagttcct cggcttctga cgagtcaggg  1800
    ctcacttcct tcttctctga tgttccagac ctcacctgag atttcctcat cgttcctgaa  1860
    gcagcgtcat agttaagcat atctgttggg tcaatccagt cgtcatcatg agcataaccc  1920
    gttatcagca acagacattc acaaaggagc agccgacaca gcatcctgaa taaggcgttg  1980
    aggttcctcc ctgttttttc agagggaccc gggccagccc ggccgcggaa gacgccgaac  2040
    cgcttacctc aaacacggtg cattaggaat ggaatcccga gcggacttca ttgacttcca  2100

<210> SEQ ID NO 29
<211> LENGTH: 253
<212> TYPE: DNA
<213> ORGANISM: Rattus norvegicus
<220> FEATURE:
<221> NAME/KEY: misc_feature
<223> OTHER INFORMATION: Incyte ID No: 701926832H1

<400> SEQUENCE: 29
atataaggta gcttttgctc agcatcaggc taatgttgcc aagatggcgc cgttaaacga    60
    tgtgtgtgct aagaagatgg attggactga aaacctctgg gaatggttta gaatttcatg   120
    gacctataag gatgacccat gccaaaagta ctatgagctc ttaatcgtca accctatttg   180
    gttggttccg ccaacaaagg ctctggcagt tacattcact aactttgtaa cggtaccatt   240
    aaagtacatt gga                                                      253

<210> SEQ ID NO 30
<211> LENGTH: 253
<212> TYPE: DNA
<213> ORGANISM: Rattus norvegicus
<220> FEATURE:
<221> NAME/KEY: misc_feature
<223> OTHER INFORMATION: Incyte ID No: 317017_Rn.1

<400> SEQUENCE: 30
atataaggta gcttttgctc agcatcaggc taatgttgcc aagatggcgc cgttaaacga    60
    tgtgtgtgct aagaagatgg attggactga aaacctctgg gaatggttta gaatttcatg   120
    gacctataag gatgacccat gccaaaagta ctatgagctc ttaatcgtca accctatttg   180
    gttggttccg ccaacaaagg ctctggcagt tacattcact aactttgtaa cggtaccatt   240
    aaagtacatt gga                                                      253
```

<210> SEQ ID NO 31
<211> LENGTH: 354
<212> TYPE: DNA
<213> ORGANISM: Homo sapiens
<220> FEATURE:
<221> NAME/KEY: misc_feature
<223> OTHER INFORMATION: Incyte ID No: 1899132F6

<400> SEQUENCE: 31

```
ggatttgaag atccactcca cttctgctca tgcgggcca gggcctgccc ctgcacgtgg   60
ccacactgct gactgggctg ctggaatgcc tgggctttgc tgcgtcctc tttggctggc  120
cttcactagt gtttgtcttc aagaatgaag attactttaa ggatctgtgt ggaccagatg  180
ctgggccgat tggcaatgcc acagggcagg ctgactgcaa agcccaggat gagaggttct  240
cactcatctt caccctgggg tccttcatga caaacttcat gacattcccc actggctaca  300
tctttgaccg gttcaagacc accgtggcac gcctcatagc catattttc taca          354
```

<210> SEQ ID NO 32
<211> LENGTH: 1225
<212> TYPE: DNA
<213> ORGANISM: Mus musculus
<220> FEATURE:
<221> NAME/KEY: misc_feature
<223> OTHER INFORMATION: Incyte ID No: 026438_Mm.1

<400> SEQUENCE: 32

```
gcagagccga gccgggcaaa gctcgacagg gaggctctgg gcggagggta gtggaaggcg    60
gtagcctggt ggcggcgagg ctgcggcgac agagatccgg gagagagttg ctgccggctg   120
gagcgcgacc tcttgcctgg tggaagctcc atggttattc catgcgcttt cttgctcaac   180
ccagagacag ctggaacaag agggctcatt gaagtcgaga gcttgccaaa ggaatttccc   240
acacatcact accagtggtc ctctctgaag ctcaggacag gatttgtgga ctcacttcac   300
ctcagaccat ggcaagcaag ggcttgcccc tttacttggc caccttgttg actggactct   360
tggaatgcat cggttttgct ggtgtcctct ttggcttgca ttcactgttg ttttgtgttca  420
aagcagaaaa ctactttca gagccctgtg aacaggactg cttgctccag agcaatgtaa   480
cagggccttc tgatttaaaa gcgcaggatg agaagttctc actcatcttt accctggcat   540
ccttcatgaa taacttcatg acctttccca ctggctacat cttgaccgc ttcaagacta   600
ctgtggcccg cctgatagcc atattttct acacctgcgc cacgatcatc attgccttca   660
cctctgcaaa cactgccatg ctgctcttcc tagccatgcc catgctcgca gtgggaggaa   720
tcctgttcct tatcaccaac ctacagattg gaacctctt tgggaaacac cgttcaacca   780
tcatcaccct ctacaatgga gcatttgact cctcctcagc agtgttcctc gtcattaagc   840
tgctttacga gcagggcatc agcctcaggt cttccttcat cttcatgtct gtctgcagtg   900
tctggcacat tgcgcgtact ttccttctga tgcccaaggg acatatcccc tacccactgc   960
ctcccaacta cagctatggc ttgtgctcca ggtttggtgc tagcaagaaa gagaataaag  1020
cagctgaaca ctgaaaccaa ggagctgcgg tcaaaggaat gtctgccacc caaggaagag  1080
aactctggac cagaaacagca tgcagcagga gcaacacgag caacactctt ttcgacgctg  1140
ctgcgctctc tcgtctgatt catcttgcac gtggtgtggc ttgtctatca tacagtttgt  1200
ggcattacct cttcattggt actct                                        1225
```

<210> SEQ ID NO 33
<211> LENGTH: 624
<212> TYPE: DNA
<213> ORGANISM: Rattus norvegicus
<220> FEATURE:
<221> NAME/KEY: misc_feature
<223> OTHER INFORMATION: Incyte ID No: 702989441H1

<400> SEQUENCE: 33

```
aaatttccta cacaccacta ccagtagtct ctgaagttca ggataggatt tgtggaccca    60
cttcacctca gaccatggcg agccagctgc cctttactt ggccaccttc ttgactgggc   120
tgctggaatg catcggtttt gctggtgtcc tctttggctg gacctcactg ttgtttgtgt   180
tcaaagcaga aaactacttt ttaaagccct gtgaacagga ctgcgtgctc gggggcaatg   240
caacaggcct ccctgacctc aaagctcagg atgagaagtt ctccctcatc ttcactctgg   300
cgtccttcat gaacaacttt atgaccttcc ccactggcta catctttgac cgcttcaaga   360
ctgctgtggc cgcgcctgtt agccatattt tctacacct gcgccacact catcattgcg   420
ttcacctctg cagacactgc catgttgctc ttcctgccca tcctatgct tgcagtggga   480
ggaatcctgt tcctcatcac caaacctaca gcttctttat gagcagggaa tcagcctcag   540
gcactccttt catcttcctg tctgtctgca gtgccttgca tgtttggcgc gtacttcct   600
tctgatgcct cggggaacat attc                                          624
```

<210> SEQ ID NO 34
<211> LENGTH: 764
<212> TYPE: DNA

```
<213> ORGANISM: Rattus norvegicus
<220> FEATURE:
<221> NAME/KEY: misc_feature
<223> OTHER INFORMATION: Incyte ID No: 286037_Rn.1

<400> SEQUENCE: 34
aaatttccta cacaccacta ccagtagtct ctgaagttca ggataggatt tgtggaccca    60
    cttcacctca gaccatggcg agccagctgc cccttttactt ggccaccttc ttgactgggc   120
    tgctggaatg catcggtttt gctggtgtcc tctttggctg gacctcactg ttgtttgtgt   180
    tcaaagcaga aaactacttt ttaaagccct gtgaacagga ctgcgtgctc ggggggcaatg  240
    caacaggcct ccctgacctc aaagctcagg atgagaagtt ctccctcatc ttcactctgg   300
    cgtccttcat gaacaacttt atgaccttcc ccactggcta catctttgac cgcttcaaga   360
    ctgctgtggc cgcgcctgtt agccatattt tctacacct gcgccacact catcattgcg    420
    ttcacctctg cagacactgc catgttgctc ttcctggcca tgcctatgct tgcagtggga   480
    ggaatcctgt tcctcatcac caaacctaca gcttctttat gagcagggaa tcagcctcag   540
    gcactccttc atcttcctgt ctgtctgcag tgcctggcat gttgggcgta ctttccttct   600
    gatgcctcgg gacatatcc cctaccact gcctccaac tatagctatg cttctgctc     660
    caggttctgt accaggaagg aagagaatga ggcagctgaa catgagacca aggagttgca   720
    gtcaagggaa tgtcagtcac caaaggaaga gaactctgga ccag                    764

<210> SEQ ID NO 35
<211> LENGTH: 490
<212> TYPE: DNA
<213> ORGANISM: Homo sapiens
<220> FEATURE:
<221> NAME/KEY: misc_feature
<223> OTHER INFORMATION: Incyte ID No: 2487050F6

<400> SEQUENCE: 35
ctcaggaagc agagcctgga gcatctccac tatggcctgg gctccactac ttctcaccct    60
    cctcgctcac tgcacaggtt cttgggccaa ttttatgctg actcagccgc actctgtgtc   120
    ggagtctccg gggaagacgg taaccatctc ctgcacccgc agcagtggca gcattgccag   180
    caactatgtg cagtggtacc agcagcgccc gggcagtgcc cccaccacta ttatctatga   240
    ggataatcaa agaccctctg gggtccctga gcggttctct ggctccatcg acaggtcctc   300
    caactctgcc tccctcacca tctctggact gaagactgag gacgaggctg actactactg   360
    tcagtcttat gatagccatc aattccattt gggtgttcgg cggagggacc aagctgaccg   420
    tcctaggtca gcccaaggct gccccctcgg tcactctgtt cccgccctcc tctgaggagc   480
    ttcaagccaa                                                          490

<210> SEQ ID NO 36
<211> LENGTH: 611
<212> TYPE: DNA
<213> ORGANISM: Macaca fascicularis
<220> FEATURE:
<221> NAME/KEY: misc_feature
<223> OTHER INFORMATION: Incyte ID No: 703200737J1

<400> SEQUENCE: 36
tttattgagt gcagggagaa gggctggatg ccttggggtg ggaggagaga cccctcccct    60
    gggatcctgc agctccaggc ccccgtgggt ggggtgaggg ttggaacct atgaacattc    120
    tgcaggggcc actgtcttct ccacggtgct cccttcgtgc gtgacctggc agctgtagct   180
    cttgtgggac ttccactggt cggacgtcag gctcaggtag ctgctggccg cgtacttgtt   240
    gttgctctgt ttggagggtt tggtggtctc cactcccgcg ttgacagcgc tgccatctgc   300
    cttccaggcc acttccacgg ctcccgggta gaagtcactg atcagacaca ctagtgtggc   360
    cttgttggct tgaagctcct cagaggaggg cgggaagaga gtgacggagg gggcagcctt   420
    gggctgaccc aggacggtca gccgggtccc tcctccgaat aagcgagcac tcaggctggt   480
    atcccatgct ccgcagtaat aatcagcctc atcccaggc tggagcccag tgatggtcag   540
    gcaggctgag gtaccagact tggagccaga gaatcggtca gaaacccgta ggtcgcttat   600
    tatctgatag a                                                        611

<210> SEQ ID NO 37
<211> LENGTH: 611
<212> TYPE: DNA
<213> ORGANISM: Macaca fascicularis
<220> FEATURE:
<221> NAME/KEY: misc_feature
<223> OTHER INFORMATION: Incyte ID No: 017816_MF.2

<400> SEQUENCE: 37
tctatcagat aataagcgac tcagggtttt ctgaccgatt ctctggctcc aagtctggta    60
    cctcagcctg cctgaccatc actgggctcc agcctgggga tgaggctgat tattactgcg   120
    gagcatggga taccagcctg agtgctcgct tattcggagg agggaccegg ctgaccgtcc   180
```

-continued

```
tgggtcagcc caaggctgcc ccctccgtca ctctcttccc gccctcctct gaggagcttc    240
aagccaacaa ggccacacta gtgtgtctga tcagtgactt ctacccggga gccgtggaag    300
tggcctggaa ggcagatggc agcgctgtca acgcgggagt ggagaccacc aaaccctcca    360
aacagagcaa caacaagtac gcggccagca gctacctgag cctgacgtcc gaccagtgga    420
agtcccacaa gagctacagc tgccaggtca cgcacgaagg gagcaccgtg gagaagacag    480
tggcccctgc agaatgttca taggttccca accctcaccc cacccacggg ggcctggagc    540
tgcaggatcc caggggaggg gtctctcctc ccaccccaag gcatccagcc cttctccctg    600
cactcaataa a                                                         611
```

<210> SEQ ID NO 38
<211> LENGTH: 619
<212> TYPE: DNA
<213> ORGANISM: Canis familiaris
<220> FEATURE:
<221> NAME/KEY: misc_feature
<223> OTHER INFORMATION: Incyte ID No: 008837_CF.1
<221> NAME/KEY: unsure
<222> LOCATION: 566
<223> OTHER INFORMATION: a, t, c, g, or other

<400> SEQUENCE: 38

```
gtcagaatca ggtatgacct ccaccatggc ctggttccct ctcctcctga ccctccttgc     60
tctctacaca gggtcctggg ccctgcctat actgactcag ccggcctcag tgtctgggtc    120
cctgggccag gtaatcacca tgtcgtgcac tggaaggagg tccaacattg gagataataa    180
tgtgggttgg taccaacaac tcccaggaag aggccccaga accgtcatct ttgctaccga    240
tagtcgaccc tcgggggtgc ccgatcgatt ctctggctcc aagtctggca gaacagccac    300
cctgaccatc tctgggctcc aggctgagga tgaggctgat tattactgct caacctggga    360
tgatagtctc aatatagctg tgttcggcgg aggcacccac ctgaccgtct tcggtcagcc    420
caaggcctcc ccctcggtca cactcttccc gccctcctct gaggagctcg gcgccaacaa    480
ggccacccctg gtgtgcctca tcagcgactt ctaccccagc ggcgtgacgg tggcctggaa    540
ggcagacggc agcccgtcac ccaggncgtg gagaccacca agccctccaa gcagagcaac    600
aacaagtacg cggcagcag                                                 619
```

<210> SEQ ID NO 39
<211> LENGTH: 295
<212> TYPE: DNA
<213> ORGANISM: Rattus norvegicus
<220> FEATURE:
<221> NAME/KEY: misc_feature
<223> OTHER INFORMATION: Incyte ID No: 700298833H1

<400> SEQUENCE: 39

```
gccaggccag gcccctgtgc tggtcctcta tgatgacacc gaccggccct cagggatccc     60
tgaccgattc tctggctcca actctgggaa cacggccacc ctgaccatca ccacagtcga    120
agccggggat gaggccgact attactgtca ggtgtggcat agtagtggtg atcagtgggt    180
attcggcgga gggaccaagc tgaccgtcct aggtcagccc aagctgcccc ctcggatcat    240
ctgttcccgc cctcctctga ggagcttcaa gccaacaagg ccacactggt gtgtc         295
```

<210> SEQ ID NO 40
<211> LENGTH: 670
<212> TYPE: DNA
<213> ORGANISM: Rattus norvegicus
<220> FEATURE:
<221> NAME/KEY: misc_feature
<223> OTHER INFORMATION: Incyte ID No: 274060_Rn.1

<400> SEQUENCE: 40

```
gccaggccag gcccctgtgc tggtcctcta tgatgacacc gaccggccct cagggatccc     60
tgaccgattc tctggctcca actctgggaa cacggccacc ctgaccatca ccacagtcga    120
agccggggat gaggccgact attactgtca ggtgtggcat agtagtggtg atcagtgggt    180
attcggcgga gggaccaagc tgaccgtcct aggtcagccc aagctgcccc ctcggatcat    240
ctgttcccgc cctcctctga ggagcttcaa gccaacaagg ccacactggt gtgtctcata    300
agtgacttct acccgggagc cgtgacagtg gcctgaaagg cagatagcag ccccgtcaag    360
gcgggagtgg agaccaccac accctccaaa caaagcaaca acaagtacg ggccagcagc    420
tacctgagcc tgacgcctga gcagtggaag tccacacgtg gctacagctg ccaggtcacg    480
catgaaggga gcaccgtgga agacagtg gccccctacag aatgttcata ggttctcatc    540
cctcaccccc caccacggga gactagagct gcaggatccc aggggagggg tctctcctcc    600
caccccaagg catcaagccc ttctccctgc actcaataaa ccctcaataa atattctcat    660
tgtcaatcag                                                           670
```

<210> SEQ ID NO 41
<211> LENGTH: 439

<212> TYPE: DNA
<213> ORGANISM: Homo sapiens
<220> FEATURE:
<221> NAME/KEY: misc_feature
<223> OTHER INFORMATION: Incyte ID No: 1414964F6

<400> SEQUENCE: 41

```
atggtacgcc gtgtcgtctg catcctggtg tggctgctgg ccttctgcgt gtctctgcct   60
gacacctact acctgaagac cgtcacgtct gcgtccaaca atgagaccta ctgccggtcc  120
ttctacgccg agcacagcat caaggagtgg ctgatcggca tggagctggt ctccgttgtc  180
ttgggctttg ccgttccctt ctccattatc gctgtcttct acttcctgct ggccagagcc  240
atctcggcgt ccagtgacca ggagaagcac agcagccgca agatcatctt ctcctacgtg  300
gtggtcttcc ttgtctgctg gctgccctac cacgtggcgg tgctgctgga catcttctcc  360
atcctgcact acatcccttt cacctgccgg ctggagcacg ccctcttcag gccctgcatg  420
tcacacagtg cctgtcgct                                                439
```

<210> SEQ ID NO 42
<211> LENGTH: 2015
<212> TYPE: DNA
<213> ORGANISM: Mus musculus
<220> FEATURE:
<221> NAME/KEY: misc_feature
<223> OTHER INFORMATION: Incyte ID No: 031166_Mm.1

<400> SEQUENCE: 42

```
tttttaggaa acaaaatctt tattaaaaaa ataacttaca aatcaacaga acgctctgtt   60
tcccttgttc acgggtttgc agcccgaagt gtaactctac aatatggttc atgtaacaaa  120
ctgcattgct gggcagtgtt gtttcatatg ctgtgccagc attaaacatt gcacagatat  180
aaaactattg taaataaaac ctttcagccg agactggcat aaatttatat atatttttat  240
atttatatat ataatttcaa atcagctaac aattaatgtc atccttagtc aaaactcaag  300
tccagctaat ctgaggccta catggtctga atacaacagc cttacacctc ccatacaata  360
tttaaaatat atttagcttt caaatacatt tataaggtac atccatagtg agaaaataaa  420
gtcttaaaac ttaaatacaa aaagtcacca agtaaaaact tgaagaaaca cagaagattc  480
tactgtacac atgtccataa gagcctgtcc tggtgctgag tttgatacgc agctctggct  540
gcacagcaca gcacagcgca gcacagcaca gcacagcaca gccctgcctg ctgccagctg  600
ccagctgcca gctgccagct gtcaggatgg gcatccaggc ggcagccatc ttggctggag  660
aatgagagac aggaagcatg gtcacatgcc ttctcctctt cataccactc aagcaaccag  720
acccaaagct acattgcttt cttgaagaaa ccacaggacc tcgccgcccc atttgcaaca  780
tgcacgtgtc ccccgacct ctgcagaatg atggatcact tggtgttctg ttccagggca  840
gagtactctg tctctgacac tctggaggca tcaatgagct tggtgagacc tgttttggcc  900
gagtacttga agatgaaggc cttcatcagc tcgtacctgt agttgcggtt gatgaagcta  960
tagagcacgg ggttgacaca gcagtgcacc aaggacaggc actgggtgac atgcaacgct 1020
gtaaagagca cattctccag ctgacaggta aacgggatgt agtgtaagat ggagaagatg 1080
tccagcagaa ccacaaaatg gtacggcagc caacatacca ggaagaccac cacgtaggag 1140
aagatgatct tccggctact gtgcttctcc tggtcgcctg atgctgacat gctctagcga 1200
gcaggaagta gaagatcgca atgatagtga aggggacagc aaagcccaag atgacagaga 1260
ccagctccat gccgatcagc cactccttga tgctgtgtcg ggggtagaag gacctgcagt 1320
aggtctcatt gttggaagca gatgtgaccg tcttgcagta gttagtatca ggccagggac 1380
acaagaaggc cagcagccac accagatgca tacaaccggc gtaccatctt cttcttatag 1440
ctggaggtgc cggtgaagta ggtgatggag agatagcggt ccacgctcat gcaggcgagg 1500
aagaagatgc tcccaagagg ttgatggaga aaatgaggtg tgtgatctgt catgtgagct 1560
cccccatggg ccactggtta tgctgcacga gactgaccac ccagacgggg atggtgatga 1620
cgacccacag gtctgcaatg gccaggttca agatgtagca gtgcgtgtcg tagcctgtgg 1680
tcttagcctg gatattcacc cagaccacca cagagttggc aatcatgccg atcacgaaga 1740
tgaaaatgta gatgaaggag agggtataca gaagcacgtt cttgttaggc atggtgggac 1800
actgcacagt gtccaccaca atgcagtcgc tgctgttaca tggccagttg atgtcagagt 1860
agttgccagg ctctgcatag tcaaacaagt gcacatccat ggtcttgagg agagcgacca 1920
agtgacctcc agggcttcct gggctgtggt tgccttcct gacggtgagc gctgcaggct 1980
ccttcagtgc tgagcagttt gtagcaactg agatc                             2015
```

<210> SEQ ID NO 43
<211> LENGTH: 1256
<212> TYPE: DNA
<213> ORGANISM: Rattus norvegicus
<220> FEATURE:
<221> NAME/KEY: misc_feature
<223> OTHER INFORMATION: Incyte ID No: 203462_Rn.3

<400> SEQUENCE: 43

```
ccccgagcac agcatcaagg agtggctcta ttggcatgga gctggtctcc gtcatcttgg   60
gttttgctgt ccccttcacc atcattgcta tcttctactt gcgctgctcg ccagagccat  120
gtcagctatc cggtgtacca ggagataaca cagcagccgg aagatcatct tctcctacg  180
tggtggtctt cctggtgtgt tggctgccgt accatttgt ggttctgctg gacatcttct  240
ctatccttgca ctacatcccg ttcacctgcc aactggagaa tgtgctcttt acagcgctgc  300
```

```
                    acgtcacgca gtgcctgtcc ctggtgcact gctgtgtcaa ccctgtgctc tacagcttca  360
                    tcaaccgaaa ctacaggtac gagctgatga aggccttcat cttcaagtac tcagccaaaa  420
                    caggactcac caaactcatc gatgcctcca gagtgtcaga gacagagtac tctgccctgg  480
                    agcagaaaca caagtgaccg tgctatagag gcatgggaac atgtgcatgt tgcaaatgga  540
                    gcagctgggc cctgcgtttt cttcaagaaa gcactgtagc tttgggtctg gttgcttgag  600
                    tggtatgaag aggagaagga ccatgcttcc tgtctctcat tctccagcca agatggctgt  660
                    cacctggaca ctcatcctga cagcttgcag cagacaggct gccctgcgct gtgcagccag  720
                    agctgtgtgt caaagccagc atcaggacag actcttctgg cacgtgtac aatagaatct   780
                    tttgtgtttc ttcaagtttt tacttggtga ctttttgtatt taagttttaa gactttattt  840
                    tctcactatg gatgtacctt ataaatgcat ttgaaagcta aatatatttt aaatattgta  900
                    tgggaggtgt aaggctgttg tatttggacc atgtaggcct cagattagca ggactctgag  960
                    ttttgactaa ggatgacatt cattgttagc tgattcgaac tgatataaat atatatataaa 1020
                    tataaatata tatataaatt tatgccagtc ctggctgaaa tgtttatttt acaatagttt 1080
                    tatatctgtg tggtgtttaa tgctggcaca gcatatgaaa cggaaactgc ccagcaatgc 1140
                    agtttgtgac acgaaccgta ttgtagagtt acgtttcggg ctgcaaaccc gtgaacagag 1200
                    gaaacagcat tctccttgatt tgtaagttat ttttttaata aagatttttg tttcct      1256

<210> SEQ ID NO 44
<211> LENGTH: 450
<212> TYPE: DNA
<213> ORGANISM: Homo sapiens
<220> FEATURE:
<221> NAME/KEY: misc_feature
<223> OTHER INFORMATION: Incyte ID No: 1976095F6

<400> SEQUENCE: 44
gccatggaca tcctggtccc actcctgcag ctgctggtgc tgcttcttac cctgccccctg  60
                    cacctcatgg ctctgctggg ctgctggcag cccctgtgca aaagctactt cccctacctg 120
                    atggccgtgc tgactcccaa gagcaaccgc aagatggaga gcaagaaacg ggagctcttc 180
                    agccagataa aggggcttac aggagcctcc gggaaagtgg ccctactgga gctgggctgc 240
                    ggaaccggag ccaacttcta gttctaccca ccgggctgaa gggtcacctg cctagaccca 300
                    aatccccact ttgagaagtt cctgacaaag agcatggctg agaacaggca ctccaatatg 360
                    agcggtttgt ggtgctcct ggagaggaca tgagacagct ggctgatggc tccatggatg  420
                    tggtggtctg cactctggtg tgtgctctgt                                     450

<210> SEQ ID NO 45
<211> LENGTH: 540
<212> TYPE: DNA
<213> ORGANISM: Macaca fascicularis
<220> FEATURE:
<221> NAME/KEY: misc_feature
<223> OTHER INFORMATION: Incyte ID No: 005653_Mf.1

<400> SEQUENCE: 45
gctctgtgca gagcccgaga aggtccttgc aggaggtccc agagagtact gagccgggag  60
                    tgtgctcttt ttctggggag catgtgacgg aaccacatgg aactgggcct tcatgtggca 120
                    agcaagtttt tagagcccac ttggaaacac attggggacg gctgctgcct caccagagag 180
                    acctggaagg atcttgagaa tgcccagttc tccgaagtcc aaatggaacg cagcccccct 240
                    cccttcaagt ggctacctgt tgggccccac atcatgggaa aggctgtcaa ataacttttc 300
                    ccaagcccaa aggcactcat ttgctccttc cccagcctac aattagaaca agtcacccac 360
                    cagcctacgt atcttccact gagagggaac tagcagaatg agaaaagcca ttcctgtccc 420
                    atctcctagt ccctgtctcc ccaacctctg ccagggcaat ctctaacttc aatccctcct 480
                    tcgacagtga taaagtctac ttctaccctg accacaggga gtaaacatct gtaccctgtt 540

<210> SEQ ID NO 46
<211> LENGTH: 1225
<212> TYPE: DNA
<213> ORGANISM: Canis familiaris
<220> FEATURE:
<221> NAME/KEY: misc_feature
<223> OTHER INFORMATION: Incyte ID No: 007876_Cf.1

<400> SEQUENCE: 46
ccctgacacc tgatggctct actgggctgc tggcagcccc tgtgcaaagc ctacttcccc  60
                    tacctaatgg ctgtgctgac ggccaagggc aaccgcaaga tggagcgtaa gaaacaggag 120
                    ctctttggcc agataaacag gcttacagga gcctccggga aggtggcctt gctggagctg 180
                    ggctgtggca ccgggggcaa cttccagttc tacccagcgg gctgcaggat cacctgcctg 240
                    gacccaaatc cccacttcga gaagttcttg acaaagagca tggctgaaa caggcatctc 300
                    caatatgaac agtttgtggt ggcttccgga gaggacatga gacaagtggc tgcagctcc 360
                    atggatgtgg tggtcagcac cctggtgctg tgctctgtgc agagtccgag gagggtcctg 420
                    caggaggtca agagagtgct gaggccggga ggactgttcc ttttctggga gcatgtggct 480
                    gagccacgtg gaagctgggc cttcctgtgg cagcaagttg tagagcccac ctggaaacac 540
                    atcggggatg gctgctgcct caccaggag acttggaagg atctcgagag tgcccagttc 600
```

-continued

```
      tcccacctcc agatggaaca caaccccct cccttcaagt ggttgcctgt tgggcccac   660
      atcatgggga aggctgtgaa ataactcttg cccaagtcca gcctccggcc gggccgagca  720
      atcccgccta ccggcggagt ctgtcttcta ctgagaggga tccaggcaga gaagccacgc  780
      tccccatcac cccctcttct cccttctcct atctctgcca caggtctcac ttcaatcctt  840
      ccttccaagg tggaaaagct ctatttccta tctggctgca ggaaggaaag tgcatcctg   900
      tcctatccct gactgcgaat tcctaggctg ggtctcccac ttttttgccca cccactgcta  960
      gagcagttcc ctgtcgcttt cccttgttcc cctagtaaag cctccccctc gtctttgcct 1020
      gagaccacat ccatgtgcct ccaggagctc atcacgaaag tcatcatacg tgcaccctg  1080
      cgtggccccc agccctccct gtcgcgtacc acctctgccc tgagccctgg gggtgcaaag 1140
      aagcagccgt ctcctgggga ccctggacga ggaggagcag gactcaacaa gaagccagag 1200
      gttttatcct gaaatatttt ttaat                                       1225
```

<210> SEQ ID NO 47
<211> LENGTH: 1314
<212> TYPE: DNA
<213> ORGANISM: Mus musculus
<220> FEATURE:
<221> NAME/KEY: misc_feature
<223> OTHER INFORMATION: Incyte ID No: 003508_Mm.1

<400> SEQUENCE: 47

```
      aaagtcctat ccgaggagga ggggagactt acatctgcca gcctggggca gaggcaaaac   60
      tctagtgttc cacgagacg tccaccagga gctggtatca tggatgccct ggttctattt   120
      ctgcagctgc tggtgctgct cctgaatcta cctctacacc tactggctct gctgggctgc  180
      tggcagccta tatgcaaaaa ctacttccct tacttcatgg ccatgctaac agccaggtcc  240
      tacaaaaaga tggaaagcaa gaaacgggaa ctatttagcc agataaaaga tctcaagggg  300
      acttccggca acgtggccct gctggagctg gtgctgcggc accggtgcca acttgccagt  360
      tctacccaca gggctgcaag gtcacctgtg tggacccaaa ccccaacttc gagaagttcc  420
      tgacaaagag catggctgag aacaggcacc tccaatatga gcgcttcatt gtggcttacg  480
      gagagaacat gaaacaactg gctgacagct ccatggatgt ggtggtctgt accctggtgc  540
      tatgttctgt ggcagagccc cagaaaggtc ctgcaggaag tccagagagt ccgaggccg   600
      ggaggcctac tgttcttctg ggagcacgtg gctgagcctc agggaagccg ggccttcctg  660
      tggcagcgag ttttagagcc tacctggaaa cacacatcgg agatggttgc cacctcacca  720
      gagagacctg gaaagacatt gagagggcac agttccgga gtccagctg gaatggcagc  780
      ccctcccctt caggtggtta cctgttgggc cccacatcat gggaaaagct gtgaaataaa  840
      ctctcccaa ggatgccatc tgatctcccc atctgcagcc agaagtcacc ccaatacagt  900
      acttctaagg aggggtcagg taaagcatga gagagactct cagcgccgcc gctgccgctg  960
      ccagggtgat cattcatcag tttcggccac tagagacaga aaactacact gctaagccct 1020
      ggactttgcc caaccccttt ctaggaccgt tttctccctc tctcttgtcc ctatggtaaa 1080
      gttctccctg gcgtccttct gaaactacac catgtggccc cttggaacta atccaagtc  1140
      aatgcgtgta tcccctgcca ggctgcctca gctccctcc ccattccca ctctgtcccc  1200
      ggggttcgga ggaatgggcg agcagaaaaa ccttaggatg agagagcggc actcaataaa 1260
      gcagccagag attttattgt caaatacttt ttaataaata gacaaaaacc actg        1314
```

<210> SEQ ID NO 48
<211> LENGTH: 1314
<212> TYPE: DNA
<213> ORGANISM: Rattus norvegicus
<220> FEATURE:
<221> NAME/KEY: misc_feature
<223> OTHER INFORMATION: Incyte ID No: 205363_Rn.4
<221> NAME/KEY: unsure
<222> LOCATION: 1045-1115
<223> OTHER INFORMATION: a, t, c, g, or other

<400> SEQUENCE: 48

```
      cgggggactt acatctgcca gcctgggcag aggcaaaaat ccagtgttcc acaagacgcg   60
      ccatcagaag ctaacggcat ggatgtcctg gttccattgc tgcagctgct ggtgctgctc  120
      ctgactctgc ctttacacct gctggctctg ctgggctgct ggcagcccat atgcaaaaacc  180
      tacttcccct acctaatggc cacactaaca gccaggtcct acaaaaagat ggagagcaag  240
      aagcgagaac tatttagcca gataaaagat cttaagggga cctccaacga agtgaccctg  300
      ctggagctgg gctgtggcac cggtgccaac ttccagttct acccgcctgg ctgcaaggtc  360
      acctgtgtgg acccaaaccc caactttgag aagtttctga ccaagagcat ggctgagaac  420
      aggcacctcc aatatgagcg cttcattgtg gcatacggag aaaacatgaa acagctggct  480
      gacagttcca tggatgtggt ggtctgtacc ctggtgctgt gttctgtgca gagccccaga  540
      aaagtccttc aggaagtcca gagagtcctg aagccgggag gctgctgtt cttctgggag  600
      catgtgtctg agcctcaggg aagcaggcc ctcctgtgcc aggagttt agaacctacc  660
      tggaaacaca tcggagatgg ctgccacctc accagagaga cctgaaaga cattgagaag  720
      gcacagttct ctgaagtcca actggaatgg cagccccctc ccttcaagtg gttacctgtt  780
      gggcccccaca tcatgggaa agctgtgaaa taactctccc caagaaggc catctgatct  840
      cccatctgc agccagaagc caccccagta cttctaagga ggggtcaggt aaagcagaga  900
      ctctcagcac cgctgccacg gccgggtga tcattaatca gcttcagcct ttctccacag  960
      tgaggctttc ttcctgctct cttgaggcag aaaactagac tgcaaggccc tggacttacc 1020
      caacccaacc cttttaggac ccctnnnnnn nnnnnnnnnn nnnnnnnnnn nnnnnnnnn  1080
      nnnnnnnnnn nnnnnnnnn nnnnnnnnn nnnntgtgt gtccttccag ccatgcccca  1140
```

-continued

```
       tgtctcacag cattgtaacg ttctccctgg tgccccttg gcatgtatcc cttgcttggc 1200
       cacctcagcc tccctcccca ccatacactc tatcctgaac tacagaggaa cagagagcag 1260
       acaaacgtca gaatgagagc agcactcaat aaagcagcca gagttcttat tgtc       1314
```

<210> SEQ ID NO 49
<211> LENGTH: 550
<212> TYPE: DNA
<213> ORGANISM: Homo sapiens
<220> FEATURE:
<221> NAME/KEY: misc_feature
<223> OTHER INFORMATION: Incyte ID No: 2890678F6

<400> SEQUENCE: 49

```
       aggaatttcc cttatctcct tcgcagtgca gctccttcaa cctcgccatg gcctctgccg  60
       gaatgcagat cctgggagtc gtcctgacac tgctgggctg ggtgaatggc ctggtctcct 120
       gtgccctgcc catgtggaag gtgactgctt tcatcggcaa cagcatcgtg gtggcccagg 180
       tggtgtggga gggcctgtgg atgtcctgcg tggtgcagag cacggccaga tgcagtgcaa 240
       ggtgtacgac tcactgctgg cgctgccaca ggacctgcag gctgcacgtg ccctctgtgt 300
       catcgccctc cttgtggccc tgttcggctt gctggtctac cttgctgggg ccaagtgtac 360
       cacctgtgtg gaggagaagg attccaaggc ccgcctggtg ctcacctctg ggattgtctt 420
       tgtcatctca gggtcctga cgctaatccc cgtgtgctgg acgtcgcatg catcatccgg 480
       gacttctata accccctggt gggctgaggc ccaaaagcgg gaactggggg gcctccctct 540
       acttggggct                                                         550
```

<210> SEQ ID NO 50
<211> LENGTH: 827
<212> TYPE: DNA
<213> ORGANISM: Canis familiaris
<220> FEATURE:
<221> NAME/KEY: misc_feature
<223> OTHER INFORMATION: Incyte ID No: 008780_Cf.1

<400> SEQUENCE: 50

```
       ggtccgctca cctggcttgt ccttctgact gcggagagct ggggagctga tccaagcgcc  60
       tctgcctctg gactccaagt gaaagtcttc cctgtggacg cagagtgtct gtcctcaccg 120
       cttggatcct acagcccttt gggtcggacc cgcacaggct tccaggtcgt agaccccagc 180
       ggacggcgag ccatggcctc catggggctg caggtgatgg catcgcgctg ggccgtgctg 240
       ggctggctgg gcgccatcct gagctgcgcg ctgcccatgt ggcgcgtgac ggccttcatc 300
       ggcagcaaca tcgtcacgtc gcagaccatc tgggagggcc tgtgatgaa ctgcgtggtg 360
       cagagcaccg gccagatgca gtgcaaggtg tacgactcgc tgctggcgct gccgcaggac 420
       ctgcaggcgg cgcgcgccct catggtcgtc agcatcatcg tggccgcgct gggcgtgctg 480
       ctgtccgtgg tgggtggcaa gtgcaccaac tgcgtggagg atgagagcgc caaggccaag 540
       accatgatcg tggcaggcgt ggtgttcctg ctggccggcc tgctggtcat ggtgccggcg 600
       tcctggacgg ccaacaatat catccgggac ttctacaacc cgctggtggt ctccggccag 660
       aagcgggaga tgggcgcctc tctctacgtg ggctgggccg cctcgggctt gctgctgctc 720
       ggcgggcgcc tcctctgctg caactgcccct cccccgcgcgg acaagcccta ctcggccaag 780
       tactcggccg cagcccgctc cgccccagcc agcaactacg tgtaggg              827
```

<210> SEQ ID NO 51
<211> LENGTH: 1491
<212> TYPE: DNA
<213> ORGANISM: Mus musculus
<220> FEATURE:
<221> NAME/KEY: misc_feature
<223> OTHER INFORMATION: Incyte ID No: 013606_Mm.1

<400> SEQUENCE: 51

```
       cgtaagaaaa aaaaatcatg ttttatttag taaagcattg tgtgagcagg gaagtgtgca   60
       aggtgtgggg gaggagggtc tacagcacag ctgggacctt ttgtaggag agtacacagt  120
       aaccttggcg atgggattca ggggccaaag gttggaagtc tcaggagtaga aaattccttg  180
       gtaacttatc acctgccctt ccagggctgg agagaagtct gaccaggaag gggtgcgtct  240
       gtcctgtgag ttaccctccg ccacagcagg aactcttggg actgggacag gatatttga   300
       gaaaaacaaa ggccaggcag ccttagaaca ctgcacagaa gatccccaga atgaataatg  360
       acgcagaaac tcaagtgtcc catcctccca gcctcagtag gctaaaagtg agaaatgcca  420
       gcagcagaga gagaggtgga gctggagctg aggttggag aggaaaaact ggagctggag  480
       gtcgatcaga gctccatgag aagagcttgt ctcaaaaaca ggtgaacaa accctaggga  540
       cagacagggc accacatgac tcactggtga gtgcttgcct accaaatgcg tgggccccca  600
       ggttcaatac ccagtagtac aaaagaaaaa caagaaataa gacagcccce aaactactcc  660
       gtaaccttc ttgatgctca agctcaggtt ccctgcctag cagagcctca ctccccagtg  720
       agcatcacac ataattcttg gtgggatatt cggagggtcc ccgagaatgt gggacagatg  780
       tagaatagca ggccatgtaa tgtctgggtc cctgggtccc tccagaagag caggcgcagc  840
       atagtagccc tccacccagc agcaaaaggc ctgaggctgc ccagcccagg tagagggagg  900
       ccctccagct cccgcttttg agcatcagcc accaagggt tgtagaagtc ctggatgata  960
```

-continued

```
      gagtgggcag tccagcagac aggaatgagc gtcaggaccc cagaaatgac aaagatgatg 1020
      ccagagatga gcaccagacg agacttggag ttcctatctt ccacacaggt agtgcacttg 1080
      gctccagcca ggtacacgag caggccaagc aggacaatga ggagggtgac aacacagagg 1140
      gctctggcag cctgcaggtc ctggggcagc gccaacagtg agtcatacac cttgcactgc 1200
      atctggccag tgctctgaac cacacaggac atccacagcc cctcccacac catctgggcc 1260
      acgacgatgc tgttgccgat gaaggcggtc accttccaca tgggcagggc acaggacacc 1320
      agggcgttga cccagccaag cagggtcagg acgatcccca agatttgcag accagtagag 1380
      gccatgatga ggtttagggg gcgagtgctc ggtcagcttt gtctgcggac gtccagtccg 1440
      gttcggccac ccctgatatc cgagcctgca aaagagactg ctaagatttc c           1491
```

<210> SEQ ID NO 52
<211> LENGTH: 701
<212> TYPE: DNA
<213> ORGANISM: Rattus norvegicus
<220> FEATURE:
<221> NAME/KEY: misc_feature
<223> OTHER INFORMATION: Incyte ID No: 248462_Rn.1

<400> SEQUENCE: 52

```
      tggcacctca cagttccctg ttttgagaca agctgtatac cggctgagag aagacttcaa  60
      ccaagaaaga acgtgagcag ccagcagaga gggacgcggc tgttcctagt ccgtggcgga 120
      tctggagggg ttgtgatggg ctgaaggctt ccaagaagac acaagcaata cagctgagcg 180
      ggacctaagg acttcttcgt attcagtgag tatcagatgt gtagaggcc cgcagatgtg 240
      aggtctggcc tggcctgaaa tcaacagctt ccctactga gcagtgagaa ccaccccgaac 300
      tccaacacgg tgctcccaac cctgttgagt gattcaggct gagagctgtg aagaccggag 360
      gagcagatag atggcttcca ctggccttga actcctcggc atgaccctgg ctgtgctagg 420
      ctggctagga accctggtgt cctgtgccct gccacatgcc aaggtgaccg ccttcattgg 480
      caacagcatc gttgtggccc aagtggtatg ggaggggctg tggatgtcct gtgtggtcca 540
      gagcactggg cagatgcagt gcaaggcgta cgactcgctg ctggcgctgc cccaggacct 600
      gcaggctgcc agagccctct gtgtcgtggc cctcctgctg gctttgctgg gcctgctggt 660
      ggctatcacg ggcgcccagt gcaccacatg tgtggaggac g                       701
```

<210> SEQ ID NO 53
<211> LENGTH: 404
<212> TYPE: DNA
<213> ORGANISM: Homo sapiens
<220> FEATURE:
<221> NAME/KEY: misc_feature
<223> OTHER INFORMATION: Incyte ID No: 2183094F6
<221> NAME/KEY: unsure
<222> LOCATION: 394
<223> OTHER INFORMATION: a, t, c, g, or other

<400> SEQUENCE: 53

```
      gaggacagga tgaggcccgg cctctcattt ctcctagccc ttctgttctt ccttggccaa  60
      gctgcagggg atttggggga tgtgggacct ccaattccca gccccggctt cagctcttc 120
      ccaggtgttg actccagctc cagcttcagc tccagctcca ggtcgggctc cagctccagc 180
      cgcagcttag gcagcggagg ttctgtgtcc cagttgtttt ccaatttcac cggctccgtg 240
      gatgaccgtg ggacctgcca gtgctctgtt tccctgccag acaccacctt tcccgtggac 300
      agagtggaac gttggaattc acagctcatg ttctttctca gaagtttgag aagaactttt 360
      ctaaagtgag ggaatatgtc caattaatta gtgngtatga aaag                    404
```

<210> SEQ ID NO 54
<211> LENGTH: 629
<212> TYPE: DNA
<213> ORGANISM: Canis familiaris
<220> FEATURE:
<221> NAME/KEY: misc_feature
<223> OTHER INFORMATION: Incyte ID No: 001680_Cf.1

<400> SEQUENCE: 54

```
      ggctccggcc ccagccccag cccagccgc agctccagct ccagctccgg ccctagctcc  60
      agccccagct ccagcccag ctccagctcc agccccagcc ccagcccag ccccggcgcc 120
      cgcccttccc cgggcctggg agcgggcgtg gggggcgcgc tcaggctccc ccgggccacc 180
      ggcgcggcgc cccgctgcaa ggtcccgcgg aaggtgcggg gggcggaacc gtgagccggg 240
      gcggcgcgga gctcgctgcc cccgaggacc tcccggggcg ccggggccgct gacctgctgt 300
      gcgtaaacac cccagccttc cgctcccgcc gctcggcccc ggcgggctg cagctaggct 360
      ttccccggct cccccccag gtggcgggct ggaaggtgcg ccctgatgcg ggcgcgggc 420
      gcctactgtg tgccggtggt aggcggcgtc tcgagacgta gttttctagc agccctcggc 480
      ccgactctgt gcgggatgga tgaggagccc catttcaccg attgggaaac tggaggcgct 540
      gcgaactgga aacccaagat caggctcgtg tctgaggcgc acgattaact gcggtctcag 600
      aactttgtcc aactagttgc tgccccgtg                                    629
```

```
<210> SEQ ID NO 55
<211> LENGTH: 518
<212> TYPE: DNA
<213> ORGANISM: Mus musculus
<220> FEATURE:
<221> NAME/KEY: misc_feature
<223> OTHER INFORMATION: Incyte ID No: 021581_Mm.1

<400> SEQUENCE: 55
gagccagcat cttaacttag aaggcacgat gagttacagc cttctctttc tcctggccct   60
      tcagttctgc cttggctctg cctcccggac aactctgacc tctgcacatt cccgggaatt  120
      gaccacacct ccaacatcac cccaggctac agctgcctgg ttgcctccgg gaggcacttc  180
      ttgggcagaa ggtgggactg tgtctcagcc actttccaat ttcactgggt ctgtggacag  240
      ccatgggacc tgccagtgtt ctgtttccct gccggatacc gcctttcccg ctgacagagt  300
      ggagcgctta gagtacacag ctcacatcct ttctcagaaa ttcgagagag agttttctaa  360
      ggtgaaggag tatgtccagc taataagtgt gtatgagaag aggctcctga acctgacggt  420
      ccgagtagag gtcatggaga aggacagcat ctcttacaca gaactggact ttgagttgat  480
      caagctggaa gtgaaggaga tgcaaaaact ggtcttac                          518

<210> SEQ ID NO 56
<211> LENGTH: 292
<212> TYPE: DNA
<213> ORGANISM: Rattus norvegicus
<220> FEATURE:
<221> NAME/KEY: misc_feature
<223> OTHER INFORMATION: Incyte ID No: 283960_Rn.1

<400> SEQUENCE: 56
aagatgtgtt acagccgtct tctcctcctg tcccttctgt tctgccttgg ctctgcctct   60
      gggagttcga gagctctgag ctctacacat tccctggaat tgaccactcc aacattacct  120
      gagactacat tacccgagac tacgactgcc tggctgcctt cgggaggcac gtcgtggaca  180
      gaaggtggta ctctgtctca gtcactttcc aatttcactg ggtctgtgga cagccatggg  240
      acctgccagt gttctgtttc cctgccggac accactttc ctgctgacag ag           292

<210> SEQ ID NO 57
<211> LENGTH: 491
<212> TYPE: DNA
<213> ORGANISM: Homo sapiens
<220> FEATURE:
<221> NAME/KEY: misc_feature
<223> OTHER INFORMATION: Incyte ID No: 2182042F6
<221> NAME/KEY: unsure
<222> LOCATION: 322-323, 330, 332
<223> OTHER INFORMATION: a, t, c, g, or other

<400> SEQUENCE: 57
agcggattgg gggtggccca ggggatgctg ctgatgtgca gagacatccc ttttccggc    60
      acatgaattg ggacgacctt ctggcctggc gtgtggaccc cccttcagg ccctgtctgc   120
      agtcagagga ggacgtgagc cagtttgata cccgcttcac acggcagacg ccggtggaca  180
      gtcctgatga cacagccctc agcgagagtg ccaaccaggc cttcctgggc ttcacatacg  240
      tggcgccgtc tgtcctggac agcatcaagg agggcttctc cttccagccc aagctgcgct  300
      cacccaggcg cctcaacagt annccccggn anccccgttt gggagggtt tcggcccagc   360
      ttgaggggtt tcggcccagc cccagcctgc cggagccac ggagctacct ctacctccac   420
      tcctgccacc gccgccgccc tcgaccaccg cccctctccc caatccgtcc ccctcaggg   480
      aacaagaagt c                                                       491

<210> SEQ ID NO 58
<211> LENGTH: 1058
<212> TYPE: DNA
<213> ORGANISM: Mus musculus
<220> FEATURE:
<221> NAME/KEY: misc_feature
<223> OTHER INFORMATION: Incyte ID No: 037196_Mm.1

<400> SEQUENCE: 58
gacgtaggca cagcccggtg ctgtcagtca gagttctgcc tggtccgggc caagggtccc   60
      gcgggaccgg gggggccatg gcgccgtat ttgatttaga cttggagacc gaggaaggga  120
      gcgagggcga gggcgaaccg gagttcagcc ctgcggacgt gtgtcccctt ggcgaattaa  180
      gggctgctgg cctgagaca tgggacact atgaagacagt agagctgaca gagagcagcg  240
      tgaacctggg tcctgagcgc atcgggcccc actgctttga gctactgagt gtactgggca  300
      agggggcta tgcaaggtg ttccaggtga gaaagtgca aggcaccaac tgggaaaaa   360
```

```
            tatatgccat gaaggtctta aggaaggcca agattgtatg cagtgccaag gacacagccc    420
            atacccgggc tgagaggaac attctagaat ctgtgaagca tcccttcatt gtagaactgg    480
            cctatgcttt ccagacaggt ggcaaactct acctcatcct ggagtgcctc agtggtggtg    540
            agctcttcac acatcttgag cgagaaggca tcttcctgga agacacagcc tgcttctacc    600
            tggcagagat cacactagcc ctgggccatc tccattcccc ggcatcatct accgggacct    660
            caagcctgag aacatcatgc tcagcagcca gggccacatc aaactgacag acttttggact   720
            ttgcaaggag tccattcatg agggtgctat cactcacacc ttctgtggca ccattgagta    780
            catgccccca gagatttcta gtgcgcactg gtcacaaccg ggcagtggac tggtggagcc    840
            tgggagccct gatgtacgac atgctcactg gatcggcaag tccagcttcc ttgggcgcag    900
            ggtgggtgtt ggggagatcc cttccagatt ggggcaggac tgggtgggag gaccccctagg   960
            ctgccctcac cttctgcctt tccagccgc ccttcactgc agagaaccgg aagaaaacta    1020
            tggataaaat cattaaaggg aagctgctgc tgcaccccc                            1058

<210> SEQ ID NO 59
<211> LENGTH: 535
<212> TYPE: DNA
<213> ORGANISM: Rattus norvegicus
<220> FEATURE:
<221> NAME/KEY: misc_feature
<223> OTHER INFORMATION: Incyte ID No: 215631_Rn.1

<400> SEQUENCE: 59
gacgtagagc acaagcctag ggctgtcagt cagagcgctg cctggtccgg gccaagggtc     60
            ccgcgggacc ggcggggcca tggcggccgt gtttgattta gacttggaga ccgaggaagg   120
            aagtgagggc gagggcgagc cggagttcaa ccctgcggac gtgtgtcccc ttggcgagtt   180
            aagggctgct ggcctggaga cagtgggaca ctatgaggag gtggaactga cagagagcag   240
            cgtcaacctg ggtcctgagc gcatcggacc ccactgcttt gagctactga gtgttctggg   300
            caaggggggt tatggcaagg tgttccaggt gagaaaagtg caaggcacca acttgggcaa   360
            aatatatgcc atgaaagtct tgagaaaggc caagattgta tgcagtgcca aggacacagc   420
            acatacccgg gctgagcgga acattctaga atcggtgaag caccccttca ttgtagaact   480
            ggcctatgct ttccagacag gtggcaaact ctacctcatc ctggagtgcc tcagt        535

<210> SEQ ID NO 60
<211> LENGTH: 298
<212> TYPE: DNA
<213> ORGANISM: Homo sapiens
<220> FEATURE:
<221> NAME/KEY: misc_feature
<223> OTHER INFORMATION: Incyte ID No: 1880692F6

<400> SEQUENCE: 60
ggcgaggcgg cggtggtggc tgagtccgtg gtggcagagg cgaaggcgac agctctaggg    60
            gttggcaccg gccccgagag gaggatgcgg gtccggatag ggctgacgct gctgctgtgt   120
            gcggtgctgc tgagcttggc ctcggcgtcc tcggatgaag aaggcagcca ggatgaatcc   180
            ttagattcca agactacttt gacatcagat gagtcagtaa aggaccatac tactgcaggc   240
            agagtagttg ctggtcaaat atttcttgat tcagaagaat ctgaattaga atcctcta     298

<210> SEQ ID NO 61
<211> LENGTH: 341
<212> TYPE: DNA
<213> ORGANISM: Canis familiaris
<220> FEATURE:
<221> NAME/KEY: misc_feature
<223> OTHER INFORMATION: Incyte ID No: 023463_Cf.1

<400> SEQUENCE: 61
gtgcctgatt cggtgttgtc atgaggcgaa ggcgacagct ccaatggggt ggggggcgcac    60
            gcgtcgagca ggatgcgggt ccgagttggt gctgacgctg tctgctctgt cggtgctgct   120
            gggctcggcc tcggcgtcct cggatgaaga aggcagtcag gatgaatcct agattccaa    180
            gactcctttg ccatcagatg agtcggtaaa ggaccacagc acagcgggca gagtagttgc   240
            tgggcaaata tttcttgatt cagaagaatc agaattagaa tcacctattc aagaaggga    300
            agatagcctc aggagccaag aagggggaaag tgtcacagaa g                        341

<210> SEQ ID NO 62
<211> LENGTH: 634
<212> TYPE: DNA
<213> ORGANISM: Mus musculus
<220> FEATURE:
<221> NAME/KEY: misc_feature
<223> OTHER INFORMATION: Incyte ID No: 017863_Mm.1

<400> SEQUENCE: 62
```

```
gcggcggcac tagaggcagc ggctgagttg gtcgcggcga cggcgacggc gacggcgagg    60
gctctcgacc ttcgagagca ggatgcaggt ccgcgtcagg ctgtcgttgc tgctgctctg   120
cgcggtgctc ctgggctcgg cagccgcgac ctcggatgac aaaactaacc aggatgactc   180
cttagattcc aagagttctt tgcccacaga tgagtcagtg aaggaccaca ccaccacggg   240
caaagtagtt gctgccagaa tatttgttga ttctgaagaa gcagaagtgg aatcccttct   300
tcaggacgag gaagatagct ccaagaccca ggaggaagag atcagctttt tagaatctcc   360
gaatccaagc agcaagacct acgaagaact aaagagagtg cggaagccag tcttgactgc   420
cattgaaggt acggcgcacg gggagccctg ccacttccct ttccttttcc tggataagga   480
gtatgatgag tgcacctcag acgggaggga agatggcaga ctgtggtgtg ccacaaccta   540
tgactacaag acagatgaga agtggggctt ctgcgaaact gaagaagatg ctgccaggac   600
agacagaaag cttcagtaaa cagactccaa atgc                              634
```

<210> SEQ ID NO 63
<211> LENGTH: 669
<212> TYPE: DNA
<213> ORGANISM: Rattus norvegicus
<220> FEATURE:
<221> NAME/KEY: misc_feature
<223> OTHER INFORMATION: Incyte ID No: 300968_Rn.1

<400> SEQUENCE: 63

```
ggaacctgag caggaaaagc gactgcgagg cggcggcgcg agaggcagcg gctgagttgg    60
tcgcggcgac ggcgacagcg agggctctcg accttcgaga gcaggatgca ggtccgcgtc   120
agactgttgt tgctgctctg cgcggtgctc ctgggctcgg ccgccgcgtc ctcagtatgt   180
aggaaactaa ccaggatgaa tccttagatt ccaaggggtgc tttacccaca gatgggtcgg   240
tgaaggacca caccactggc aaagtagttg ctggccagaa atttgttgat tctgaggact   300
cagaggtgga atcccttctt caggacgagg aagagagctc caagagccaa gaggaagtca   360
gtgtcacgga agacatcagc tttttagact ctccaaatcc aagcagcaag acctacgaag   420
aactaaagag agtgcggaag ccagttttga ctgccattga aggtacggcg cacggggtag   480
ccctgccact tccctttcct tttcctggat ataggttata tgatgagtgc acatcagacg   540
ggagggaaga tggcagactg tggtgtgcca caacctatga ctacaagaca gatgagaagt   600
ggggcttctg cgaaaccgaa gaagatgctg ccaaaaggcg acagatgcag gaagcagaag   660
ccatctatc                                                          669
```

<210> SEQ ID NO 64
<211> LENGTH: 541
<212> TYPE: DNA
<213> ORGANISM: Homo sapiens
<220> FEATURE:
<221> NAME/KEY: misc_feature
<223> OTHER INFORMATION: Incyte ID No: 1266985F6
<221> NAME/KEY: unsure
<222> LOCATION: 215
<223> OTHER INFORMATION: a, t, c, g, or other

<400> SEQUENCE: 64

```
ggaagctgtg tggaaggaga agctggtggc cacagcagag tcctgctctg gggacgcctg    60
cttcatttac aagcctcaag atggctctgt gtagggcctg agcttgctgc ccaacgggag   120
gatgccttca cagcagagcc agcatggaggg gtggggcttg cttgagccaa               180
actgcaaagg ctgtggtggc tgtgaggaca ctgcngggt tggggggggg cgtctgtacc   240
tcaggggatg cccgctgtgt gtcacccaga gaatcaccct tcctggtcta cagatggaag   300
ctgcaggttg gtgactttgc aaatgcactt cctacagatg aactattaaa agacctgcaa   360
cattgaaaaa actcattttt tcccaccaaa accttggcca ggtaacctac cttaggcacc   420
tgcaaagaac aggaagtgat ggctgtctcg caacagagcc tgggctgctc ctcctgctct   480
ggggagtcta ggccgtgggg actgttctgg gggaggtcat gctgtctcca tgacgtctgt   540
g                                                                 541
```

<210> SEQ ID NO 65
<211> LENGTH: 403
<212> TYPE: DNA
<213> ORGANISM: Homo sapiens
<220> FEATURE:
<221> NAME/KEY: misc_feature
<223> OTHER INFORMATION: Incyte ID No: 396450R6
<221> NAME/KEY: unsure
<222> LOCATION: 27, 69, 88, 123, 131, 170, 213, 233, 296, 312, 364, 396-397
<223> OTHER INFORMATION: a, t, c, g, or other

<400> SEQUENCE: 65

```
ggggaagaag agccgcgacc gagagangcc gccgagcgtc cccgccctca gagagcagcc    60
tcccgagana ggcacttgct ggattctnca aaagtatctg cagtggcgtg tccaccagga   120
ganccctcagc ntgcctggaa gatgccgaga tcgtgctgca gccgctcggn ggcctgtttg   180
```

```
ctggccttgc tgcttcaggc ctccatggaa gtncgtggct ggtgcctgga gancagccag   240
tgtcaggacc tcaccacgga aagcaacctg ctggagtgca tccgggcctg caagcncgac   300
ctctcggccg anactcccat gttcccggga aatggcgacg agcagcctct gaccgagaac   360
cccnggaagt acgtcatggg ccacttccgc tgggannnat tcg                      403
```

<210> SEQ ID NO 66
<211> LENGTH: 411
<212> TYPE: DNA
<213> ORGANISM: Mus musculus
<220> FEATURE:
<221> NAME/KEY: misc_feature
<223> OTHER INFORMATION: Incyte ID No: 019409_Mm.2

<400> SEQUENCE: 66

```
gggaagagaa aagaggttaa gagcagtgac taagagaggc cactgaacat ctttgtcccc    60
agagagctgc ctttccgcga cagagactag gcctgacacg tggaagatgc cgagattctg   120
ctacagtcgc tcaggggccc tgttgctggc cctcctgctt cagacctcca tagatgtgtg   180
gagctggtgc ctggagagca gccagtgcca ggacctcacc acggagagca acctgctggc   240
ttgcatccgg gcttgcaaac tcgacctctc gctggagacg cccgtgtttc ctggcaacgg   300
agatgaacag cccctgactg aaaaccccg gaagtacgtc atgggtcact tccgctggga   360
ccgcttcggc cccaggaaca gcagcagtgc tggcagcgcg gcgcagaggc g              411
```

<210> SEQ ID NO 67
<211> LENGTH: 445
<212> TYPE: DNA
<213> ORGANISM: Rattus norvegicus
<220> FEATURE:
<221> NAME/KEY: misc_feature
<223> OTHER INFORMATION: Incyte ID No: 216194_Rn.7

<400> SEQUENCE: 67

```
cgacggagga gaaaagaggt taaggagcag tgactaagag aggccactga acatcttcgt    60
cctcagaga ctgcctttcc gcgacagcca cacgcatctc ccatcttctg agccctgctc   120
ctgtcctcag aaagccttgg actgtaaaga gcctcagcca cctggaagat gccgagattc   180
tgctacagtc gctcagggcc cctgctgctg gcctcctgc ttcagacctc catagacgtg   240
tggagctggt gcctggagag cagccagtgc caggacctca ccacggaaag caacctgctg   300
gcttgcatcc gggcctgcag acttgacctc tcggcggaga cgcccgtgtt tccaggcaac   360
ggagatgaac agcccttgac tgaaaatccc cggaagtacg tcatgggtca cttccgctgg   420
gaccgcttcg gccccagaaa cagca                                         445
```

<210> SEQ ID NO 68
<211> LENGTH: 546
<212> TYPE: DNA
<213> ORGANISM: Homo sapiens
<220> FEATURE:
<221> NAME/KEY: misc_feature
<223> OTHER INFORMATION: Incyte ID No: 506333T6

<400> SEQUENCE: 68

```
aacaaacaaa aaagcatagc attttacaga agataagcat tttacagaag aggctaagag    60
aagatagcag cttggccaag gttggggccg agacgtgaag cccagggggct gccctcactc   120
acccccctggc tgaaggcaat gatgatgagg gccacgcagg cagtggcggc caccagcagg   180
agcgtgagca gcagcggccc atgctggctg gtgagctggt acttctcgta gagcgcatct   240
tggtcaggc cctcctcgcc ctcgttgagg aagtagcgcc ccttggctgg catcctccac   300
ccttggcacg cgtgtcgtta agggccgtt aaggaggccc cagggcctgg agggcatctg   360
tctgccaaca cctcccccg tgggcctagg cctctgtcct ctccgggca ggcaagcagg   420
gctggggaga gggcctctgg gcctgctgct ccatggccaa caagggtcc gcacagctct   480
ggcaccaggc ctcactcact gtgccgccag catcctcctg tgcatccaga ctgggcttac   540
tccaca                                                              546
```

<210> SEQ ID NO 69
<211> LENGTH: 479
<212> TYPE: DNA
<213> ORGANISM: Homo sapiens
<220> FEATURE:
<221> NAME/KEY: misc_feature
<223> OTHER INFORMATION: Incyte ID No: 764465R6

<400> SEQUENCE: 69

```
cgggaagcca tgcaggatga agatggatac atcaccttaa atattaaaac tcggaaacca    60
gctctcgtct ccgttggctc tgcatcctcc tcctggtggc gtgtgatggc tttgattctg   120
```

```
ctgatcctgt gcgtgggat ggttgtcggg ctggtggctc tgggatttg gtctgtcatg   180
cagcgcaatt acctacaaga tgagaatgaa aatcgcacag gaactctgca acaattagca   240
aagcgcttct gtcaatatgt ggtaaaacaa tcagaactaa agggcacttt caaaggtcat   300
aaatgcagcc cctgtgacac aaactggaga tattatggag atagctgcta tgggttcttc   360
aggcacaact taacatggga agagagtaag cagtactgca ctgacatgaa tgctactctc   420
ctgaagattg acaaccggaa cattgtggag tacatcaaag ccaggactca tttaattcg    479
```

<210> SEQ ID NO 70
<211> LENGTH: 534
<212> TYPE: DNA
<213> ORGANISM: Mus musculus
<220> FEATURE:
<221> NAME/KEY: misc_feature
<223> OTHER INFORMATION: Incyte ID No: 028681_Mm.2

<400> SEQUENCE: 70

```
ctccctcagg acggaacatc ccttcactca gagctgaaga taagagagca ggaaacgagc    60
cccgcatcta ctctttcacc acaagttatt attattttg ttttaggtt caagcccacg    120
tatctctgaa catccaagaa agggcttcct ggaaaacaaa acaaagcaaa acaaacccca   180
agtgtcctgg tgcatatggc cccacaccac cgggagagaa ggagcccaca ctggcaggca   240
ctgagactct aagggtggac attgggtgag ttctgcagag tcactgagct ctgagctctt   300
tgctgttcaa ggggagccat gcaggatgaa gatgggtata tcactttaaa catcaagccc   360
cggaaacaag ctctcagctc agcggaacct gcctcttctt ggtggcgtgt gatggcttta   420
gttctgctga tctcatccat ggggctggtt gttggactga tggctctggg gatcatgtcg   480
gtcacacagc aaaagtatct actggcggag aaggaaaatc tctcagcgac tctg          534
```

<210> SEQ ID NO 71
<211> LENGTH: 732
<212> TYPE: DNA
<213> ORGANISM: Rattus norvegicus
<220> FEATURE:
<221> NAME/KEY: misc_feature
<223> OTHER INFORMATION: Incyte ID No: 211274_Rn.1

<400> SEQUENCE: 71

```
ggttcaagtc cacgtatctc tgaacatcca tgaaagggct tcctggaaaa caagacgaag    60
caaaacaaaa cccaagtgtt ctgatgcgca tggctccaga gcagcaagag acaaggatcc   120
caggctgaaa tcctaagagg ggacgctggg tgagttctgc aaaagtcact gagctttgac   180
ctcctggcag ttcaaggga accatgcagg atgaagatgg atatatcacc ttaaacatca    240
agccccggaa acaagctctc agctcagaaa tacatcacag acaggattac ttcagtccgt   300
tggattggat tatcacgcca gaactctaag aaagactgga tgtgggaaga cagctcagtt   360
cttcacaata attcgattga tctttctagg aatacagaag aaaacatgaa ttgtgcttat   420
cttcataatg gaaaaatcca cccagcttcc tgtacagaga gacattactt aatatgtgag   480
agaaatgctg ccctgacaag agtggaacaa ctgctttaat gcagaaggac cggcaggatg   540
tcagagaagt gcttgaccat gcaataaaag atctggacaa agcacccata aaactgcttg   600
ttttggtttt tatgtcatcc ttatacaata ggtctgatct tttctctgta gattaagaaa   660
ctagcatgtg aacagttctc tagctttccc aataactttc ttttttttcat ccattcttca   720
tttttcttagc tt                                                      732
```

<210> SEQ ID NO 72
<211> LENGTH: 450
<212> TYPE: DNA
<213> ORGANISM: Homo sapiens
<220> FEATURE:
<221> NAME/KEY: misc_feature
<223> OTHER INFORMATION: Incyte ID No: 2741185T6
<221> NAME/KEY: unsure
<222> LOCATION: 399
<223> OTHER INFORMATION: a, t, c, g, or other

<400> SEQUENCE: 72

```
catcattcat atgtatccaa gcaaaaggca gagcagtttt acctttaaat gctaaaagta    60
ctggttggct ctgtaggacc ctcagaatca aaaggaaact cctccacact ttgtctctgt   120
cttctccagg acccatattt cttggccact ttcataacgt agttttgaaa gatgctccca   180
taaaaacata aaggattggg ttgaggcagc tgtgaaagag tgcgatgctt tctgtgactt   240
ggatggcgat gtccatgcgt ttgctcatgt tgcagctggt gatcagggag tagatgatgt   300
ctatggctcg gcagaacttg acaatgttat aaggcagttg agtgacaatg aaaactataa   360
cgactgtgag cagaactttt agggtcgag atattttant gtttggcatc ttcatgagtg   420
tcttgctgtg ataaagtagc acaccccat                                     450
```

<210> SEQ ID NO 73
<211> LENGTH: 469

```
<212> TYPE: DNA
<213> ORGANISM: Homo sapiens
<220> FEATURE:
<221> NAME/KEY: misc_feature
<223> OTHER INFORMATION: Incyte ID No: 2741185F6.comp
<221> NAME/KEY: unsure
<222> LOCATION: 66
<223> OTHER INFORMATION: a, t, c, g, or other

<400> SEQUENCE: 73
cagttgagtg acaatgaaaa ctataacgac tgtgagcaga acttttaggg gtcgagatat    60
    tctatngttt ggcatcttca tgagtgtcct tgctgtgata aagcactcct gattggctgg   120
    ggactttagt tactgccaca tatctgtcta tgctgataca agccagaaac tgctagcaca   180
    cccccataat aagaaagggt actacaaatc caatgcagat ctctagcatt tgaatcaatg   240
    cttttcattga tgttcctagg tagcgggga aaatgggaat gcacctagca ttgtcattta   300
    ctgtataaaa aaaccagctg gggtatgctc agcaagatgg cagccatcca gacacagaaa   360
    cagatgatcc agcatggttt tccattccag agacaaagtt tagtgtgtac aaggctgaag   420
    ttattttgca cattattttc cctaaaaccc acccatgaac tgcattaac                469

<210> SEQ ID NO 74
<211> LENGTH: 241
<212> TYPE: DNA
<213> ORGANISM: Homo sapiens
<220> FEATURE:
<221> NAME/KEY: misc_feature
<223> OTHER INFORMATION: Incyte ID No: 2741185H1.comp

<400> SEQUENCE: 74
tactgtataa aaaaaccagc tggggtatgc tcagcaagat ggcagccatc cagacacaga    60
    aacagatgat ccagcatggt tttcccactc ctgattggct ggggacttta gttactgcca   120
    catatctgtc tatgctgata caagccagaa actgcattcc agagacaaag tttagtgtgt   180
    acaaggctga agttattttg cacattattt ccctaaaaac ccacccatga actgcattaa   240
    c                                                                   241

<210> SEQ ID NO 75
<211> LENGTH: 404
<212> TYPE: DNA
<213> ORGANISM: Homo sapiens
<220> FEATURE:
<221> NAME/KEY: misc_feature
<223> OTHER INFORMATION: Incyte ID No: 2547002F6

<400> SEQUENCE: 75
cagaaactgc attccagaga caaagtttag tgtgtacaag gctgaagtta ttttgcacat    60
    tattttccct aaaacccacc catgaactgc attaacagcc caaaaggca gagtgaatag   120
    aaggagtaaa tctgctacag ccaaattcag gatgtacaca tctgttttgg ttctctgttt   180
    cttgtaatag gcataaattg ccactaccat ggaattgcct gcaagtccaa tgacgaaagc   240
    tattgtgagg aatacaggga ggaaaacttt tgcaaattct ctgacatctt ctttgataca   300
    gatcaattca tattgactgt agtcataagt gccatcattc atttcctcat aataataatc   360
    tgttgactgg ttctgttcca aagccatggc tcccaatctc agat                    404

<210> SEQ ID NO 76
<211> LENGTH: 258
<212> TYPE: DNA
<213> ORGANISM: Homo sapiens
<220> FEATURE:
<221> NAME/KEY: misc_feature
<223> OTHER INFORMATION: Incyte ID No: 2547002H1

<400> SEQUENCE: 76
cagaaactgc attccagaga caaagtttag tgtgtacaag gctgcagtta ttttgcacat    60
    tattttccct aaaacccacc catgaactgc attaacagcc caaaaggca gagtgaatag   120
    aaggagtaaa tctgctacag ccaaattcag gatgtacaca tctgttttgg ttctctgttt   180
    cttgtaatag gcataaattg ccactaccat ggcattgcct gcaagtccaa tgacgaaagc   240
    tattgtgagg aatacagg                                                 258

<210> SEQ ID NO 77
<211> LENGTH: 326
<212> TYPE: DNA
<213> ORGANISM: Mus musculus
<220> FEATURE:
```

<221> NAME/KEY: misc_feature
<223> OTHER INFORMATION: Incyte ID No: 000569_Mm.1

<400> SEQUENCE: 77

```
gccctataac gttgttaagt tctgccaagc catagatgcc atctacctgc tgatcaccag   60
ctgcgatatg agcaaacgca tggatgtcgc catccaactc acagagagca tcgcgctctt  120
ccacagctgc ctcaaccccca tcctgtatgt cttcatggggg gcctccttca aaaactatat  180
catgaaagtg gccaagaaat atggatcctg gagaagacag agacagaacg tggaagaaat  240
tcctttgat tctgagggtc ctacagagcc aaccagttct tttaccattt aaatataaaa   300
ctgctctctg cctctgcttt ttgctt                                        326
```

<210> SEQ ID NO 78
<211> LENGTH: 1216
<212> TYPE: DNA
<213> ORGANISM: Rattus norvegicus
<220> FEATURE:
<221> NAME/KEY: misc_feature
<223> OTHER INFORMATION: Incyte ID No: 251020_Rn.1

<400> SEQUENCE: 78

```
gtgatctgca taaaagaaga ggtcaggcag tttgcgaaag tcttcctgcc tgccttcttc   60
acggtcgcct ttgtcattgg acttgcaggg aactccatag ttgtggcgat ttatgcctat  120
tacaagaaac agaggaccaa gaccgatgtg tacatcctga atctggctgt agcagacttg  180
ttgcttctgg tcacgctgcc tttctgggca gttaacgcag ttcatggggtg gattctaggc  240
aaaatgatgt gcaaagtaac ttcggccctg tacacggtaa actttgtctc cgggatgcag  300
ttcctggctt gtatcagcat tgacagatac tgggcaatca ctaaggcccc cagccaatca  360
ggagtgggga aaccctgctg gatcatctgt tgctgtgtgt ggacagccgc catcttgctg  420
agcatccccc agctggtttt ctacaccgtg aatgagaatg ctagatcac gcccgtcttt  480
ccccaccacc taggaacatc cctgaaagca tccattcaga tgctggaaat cttcatcggt  540
tttgtgttc cctttctcat catgggcgtg tgctatgcca tgactgctag gaagctcatc  600
aagatgccca acattaaaaa gtcccgcccc ctcagggttc tgctcgcggt ggttgttgtt  660
ttcattgtca ctcagctgcc ctacaacgtt gtcaagttct gccaagccat agatgactca  720
gtacgcttgg taaaacatta aaattgctct atgaaaactg ggaagcttgt ggatgttaat  780
attattacat cgcagtgggg aatggcttgt ttttggcggt ggtgtgtctg aaaattaaac  840
ataaaccctg aactgaaacc ttacttttca gtgactggat ggatgggcag ctgagtgaac  900
cccaaagctc agtcagttat tccacggcag ccacggagtt cagaaggttt gtgcttatag  960
acatgagctc ctgcctttga agagactcca gcatctcata gcagaacctg ctaggagtgg 1020
gagaacgctg ttgtattgcc ttgatttctg tctctctgcc tctgtctctc tcttctttct 1080
ttcattcaaa tccaaaccga cagtggattg tgatgggtc atttgcttgg acctgggggct 1140
ctgtaaaatt aaaactataa agtaaatgtt agttgtcatg aggcgtggtg gcgacatctt 1200
taagtccagc acttag                                                 1216
```

<210> SEQ ID NO 79
<211> LENGTH: 350
<212> TYPE: PRT
<213> ORGANISM: Bos taurus
<220> FEATURE:
<221> NAME/KEY: misc_feature
<223> OTHER INFORMATION: GenBank No: g399711

<400> SEQUENCE: 79

```
Met Ala Val Glu Tyr Asn Gln Ser Thr Asp Tyr Tyr Glu Glu
  1               5                  10                  15
Asn Glu Met Asn Asp Thr His Asp Tyr Ser Gln Tyr Glu Val Ile
             20                  25                  30
Cys Ile Lys Glu Glu Val Arg Lys Phe Ala Lys Val Phe Leu Pro
             35                  40                  45
Ala Phe Phe Thr Ile Ala Phe Ile Ile Gly Leu Ala Gly Asn Ser
             50                  55                  60
Thr Val Val Ala Ile Tyr Ala Tyr Tyr Lys Lys Arg Arg Thr Lys
             65                  70                  75
Thr Asp Val Tyr Ile Leu Asn Leu Ala Val Ala Asp Leu Phe Leu
             80                  85                  90
Leu Phe Thr Leu Pro Phe Trp Ala Val Asn Ala Val His Gly Trp
             95                 100                 105
Val Leu Gly Lys Ile Met Cys Lys Val Thr Ser Ala Leu Tyr Thr
            110                 115                 120
Val Asn Phe Val Ser Gly Met Gln Phe Leu Ala Cys Ile Ser Thr
            125                 130                 135
Asp Arg Tyr Trp Ala Val Thr Lys Ala Pro Ser Gln Ser Gly Val
            140                 145                 150
Gly Lys Pro Cys Trp Val Ile Cys Phe Cys Val Trp Val Ala Ala
            155                 160                 165
Ile Leu Leu Ser Ile Pro Gln Leu Val Phe Tyr Thr Val Asn His
```

|  |  |  |  | 170 |  |  |  |  | 175 |  |  |  |  | 180 |
|--|--|--|--|--|--|--|--|--|--|--|--|--|--|--|
| Lys | Ala | Arg | Cys | Val | Pro | Ile | Phe | Pro | Tyr | His | Leu | Gly | Thr | Ser |
|  |  |  |  | 185 |  |  |  |  | 190 |  |  |  |  | 195 |
| Met | Lys | Ala | Ser | Ile | Gln | Ile | Leu | Glu | Ile | Cys | Ile | Gly | Phe | Ile |
|  |  |  |  | 200 |  |  |  |  | 205 |  |  |  |  | 210 |
| Ile | Pro | Phe | Leu | Ile | Met | Ala | Val | Cys | Tyr | Phe | Ile | Thr | Ala | Lys |
|  |  |  |  | 215 |  |  |  |  | 220 |  |  |  |  | 225 |
| Thr | Leu | Ile | Lys | Met | Pro | Asn | Ile | Lys | Lys | Ser | Gln | Pro | Leu | Lys |
|  |  |  |  | 230 |  |  |  |  | 235 |  |  |  |  | 240 |
| Val | Leu | Phe | Thr | Val | Val | Ile | Val | Phe | Ile | Val | Thr | Gln | Leu | Pro |
|  |  |  |  | 245 |  |  |  |  | 250 |  |  |  |  | 255 |
| Tyr | Asn | Ile | Val | Lys | Phe | Cys | Gln | Ala | Ile | Asp | Ile | Ile | Tyr | Ser |
|  |  |  |  | 260 |  |  |  |  | 265 |  |  |  |  | 270 |
| Leu | Ile | Thr | Asp | Cys | Asp | Met | Ser | Lys | Arg | Met | Asp | Val | Ala | Ile |
|  |  |  |  | 275 |  |  |  |  | 280 |  |  |  |  | 285 |
| Gln | Ile | Thr | Glu | Ser | Ile | Ala | Leu | Phe | His | Ser | Cys | Leu | Asn | Pro |
|  |  |  |  | 290 |  |  |  |  | 295 |  |  |  |  | 300 |
| Val | Leu | Tyr | Val | Phe | Met | Gly | Thr | Ser | Phe | Lys | Asn | Tyr | Ile | Met |
|  |  |  |  | 305 |  |  |  |  | 310 |  |  |  |  | 315 |
| Lys | Val | Ala | Lys | Lys | Tyr | Gly | Ser | Trp | Arg | Arg | Gln | Arg | Gln | Asn |
|  |  |  |  | 320 |  |  |  |  | 325 |  |  |  |  | 330 |
| Val | Glu | Glu | Ile | Pro | Phe | Glu | Ser | Glu | Asp | Ala | Thr | Glu | Pro | Thr |
|  |  |  |  | 335 |  |  |  |  | 340 |  |  |  |  | 345 |
| Ser | Thr | Phe | Ser | Ile |  |  |  |  |  |  |  |  |  |  |
|  |  |  |  | 350 |  |  |  |  |  |  |  |  |  |  |